(12) United States Patent
Turchi et al.

(10) Patent No.: US 11,207,296 B2
(45) Date of Patent: Dec. 28, 2021

(54) XPA INHIBITOR COMPOUNDS AND THEIR USE

(71) Applicant: INDIANA UNIVERSITY RESEARCH AND TECHNOLOGY CORPORATION, Indianapolis, IN (US)

(72) Inventors: John J. Turchi, Indianapolis, IN (US); Navnath Gavande, Indianapolis, IN (US); Pamela S. Vandervere-Carozza, Zionsville, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 16/647,746

(22) PCT Filed: Sep. 18, 2018

(86) PCT No.: PCT/US2018/051416
§ 371 (c)(1),
(2) Date: Mar. 16, 2020

(87) PCT Pub. No.: WO2019/060260
PCT Pub. Date: Mar. 28, 2019

(65) Prior Publication Data
US 2020/0222367 A1 Jul. 16, 2020

Related U.S. Application Data

(60) Provisional application No. 62/560,561, filed on Sep. 19, 2017.

(51) Int. Cl.
*A61K 31/4155* (2006.01)

(52) U.S. Cl.
CPC .............................. *A61K 31/4155* (2013.01)

(58) Field of Classification Search
CPC .......................... A61K 31/4155; C07D 405/14
See application file for complete search history.

(56) References Cited

U.S. PATENT DOCUMENTS

| 2010/0216853 A1 | 8/2010 | Marmorstein et al. |
| 2013/0142887 A1 | 6/2013 | Alani et al. |

FOREIGN PATENT DOCUMENTS

| WO | 2015028929 A1 | 3/2015 |
| WO | 2017/205503 | 11/2017 |
| WO | WO2017/205503 A1 | 11/2017 |

OTHER PUBLICATIONS

PCT International Search Report and Written Opinion completed Dec. 12, 2019 and issued in connection with PCT/US2018/051416.
Neher, T.M., et al. "Identification of Novel Small Molecule Inhibitors of the XPA Protein Using in Silico Based Screening", ACS Chemical Biology, vol. 5, No. 10,Oct. 15, 2010 (Oct. 15, 2010), pp. 953-965, XP055159629, ISSN: 1554-8929.
Bowers, E.M., et al. "Virtual Ligand Screening of the p300/CBP HistoneAcetyltransferase: Identification of a Selective Small Molecule Inhibitor", Chemistry & Biology, vol. 17, No. 5, May 1, 2010 (May 1, 2010), pp. 471-482, XP055575681, GB ISSN: 1074-5521.
Moreau, F., et al.: "Discovery of new Gram-negative antivirulence drugs: Structure and properties of novel E. coli WaaC inhibitors", BIORGANIC & Medicinal Chemistry Letters, Elsevier, Amsterdam , NL, vol. 18, No. 14, Jul. 15, 2008 (2008-07-15), pp. 4022-4026 XP022852889, Issn: 0960-894X,.
Gavande, N. S. et al.: "Design and Structure-Guided Development of Novel Inhibitors of the Xeroderma Pigmentosum Group A (XPA) Protein-DNA Interaction", Journal of Medicinal Chemistry, vol. 60, No. 19, Sep. 21, 2017 (Sep. 21, 2017), pp. 8055-8070, XP055796870, US ISSN: 0022-2623.
Sugitani, N., et al. "XPA: A key scaffold for human nucleotide excision repair." DNA Repair (Amst). Aug. 2016, 44:123-135. doi: 10.1016/j.dnarep.2016.05.018. Epub May 20, 2016. PMID: 27247238; PMCID: PMC4958585.
Fadda E. "Role of the XPA protein in the NER pathway: A perspective on the function of structural disorder in macromolecular assembly." Comput Struct Biotechnol J. Dec. 8, 2015;14:78-85. doi: 10.1016/j.csbj.2015.11.007. PMID: 26865925; PMCID: PMC4710682.
Ikegami, T., et al. "Solution structure of the DNA- and RPA-binding domain of the human repair factor XPA" Nat. Struct. Bio., vol. 5, No. Aug. 8, 1998 (pp. 701-706).
Buchko, G.W., et al. "Structural features of the minimal DNA binding domain (M98-F219) of human nucleotide excision repair protein XPA" Nucleic Acids Research, 1998, vol. 26, (pp. 2779-2788).
Sugitani, N., et al. "Redefining the DNA-Binding Domain of Human XPA" Journal of the American Chemical Society, 2014, 136, 10830-10833.
Hilton, B., et al. "A new structural insight into XPA-DNA interactions" Biosci. Rep. 34(6), 831-40 (2014).
Saijo, M., et al. "Nucleotide Excision Repair by Mutant Xeroderma Pigmentosum Group A (XPA) Proteins with Deficiency in Interaction with RPA" J. Biol. Chem, v. 286, No. 7, pp. 5476-5483, Feb. 18, 2011.
Patrick, S.M., et al. "Xeroderma Pigmentosum Complementation Group A Protein (XPA) Modulates RPA-DNA Interactions via Enhanced Complex Stability and Inhibition of Strand Separation Activity" J. Biol. Chem. v. 277, No. 18, pp. 16096-16101, May 3, 2002.
Koch, S.C., et al. "Structural insights into the recognition of cisplatin and AAF-dG lesion by Rad14 (XPA)" Proc. Natl. Acad. Sci. U. S. A. 2015, 112, 8272-8277.
Yang, Z. "Specific and Efficient Binding of Xeroderma Pigmentosum Complementation Group A to Double-Strand/Single-Strand DNA Junctions with 3' and/or 5'-ssDNA Branches" Biochemistry 2006, 45, 15921-15930.
Tracy M. Neher et al.: "Identification of Novel Small Molecule Inhibitors of the XPA Protein Using in Silico Based Screening", ACS Chemical Biology, vol. 5, No. 10,Oct. 15, 2010 (Oct. 15, 2010), pp. 953-965, XP055159629, ISSN: 1554-8929, DOI: 10.1021 /cb1000444.

(Continued)

*Primary Examiner* — Kamal A Saeed
(74) *Attorney, Agent, or Firm* — Barnes & Thornburg LLP

(57) ABSTRACT

The present disclosure relates to certain compounds having binding affinity for XPA, and uses thereof. Specifically, the present disclosure relates to the use of XPA inhibitors as described herein in in methods of treating cancer.

23 Claims, 8 Drawing Sheets

(56) References Cited

OTHER PUBLICATIONS

Erin M. Bowers et al.: "Virtual Ligand Screening of the p300/CBP HistoneAcetyltransferase: Identification of a Selective Small Molecule Inhibitor", Chemistry & Biology, vol. 17, No. 5, May 1, 2010 (May 1, 2010), pp. 471-482, XP055575681, GB ISSN: 1074-5521, DOI: 10.1016/j.chembiol.2010.03.006.

Moreau F et al.: "Discovery of new Gram-negative antivirulence drugs: Structure and properties of novel *E. coli* WaaC inhibitors", Biorganic & Medicinal Chemistry Letters, Elsevier, Amsterdam , NL, vol. 18, No. 14, Jul. 15, 2008 (Jul. 15, 2008), pp. 4022-4026 XP022852889, ISSN: 0960-894X, DOI: 10.1016/J.BMCL.2008.05. 117 [retrieved on Jun. 5, 2008].

Gavande Navnath S. et al.: "Design and Structure-Guided Development of Novel Inhibitors of the Xeroderma Pigmentosum Group A (XPA) Protein-DNA Interaction", Journal of Medicinal Chemistry, vol. 60, No. 19, Sep. 21, 2017 (Sep. 21, 2017), pp. 8055-8070, XP055796870, US ISSN: 0022-2623, DOI: 10.1021/acs.jmedchem. 7b00780 Retrieved from the Internet: URL:https://pubs.acs.org/doi/pdf/10.1021/acs.jmedchem.7b00780.

Norie Sugitani, et al., XPA: A key scaffold for human nucleotide excision repair; 2016 Elsevier V.B.; http://dx.doe.org/10.106/j.dnarep.2016.05.08 (pp. 123-135).

Elisa Fadda; Role of the XPA protein in the NER pathway: A perspective on the function of structural disorder in macromolecular assembly; http://dx.doi.org/10.1016/j.csbj.2015.11.007 2001-0370/© 2015 Fadda. Published by Elsevier B.V. on behalf of the Research Network of Computational and Structural Biotechnology. This is an open access article under the CC By license (http://creativecommons.org/licenses/by/4.0/).

Solution structure of the DNA- and RPA-binding domain of the human repair factor XPA; Natural Structural Biology, vol. 5 No. 8 Aug. 1998 (pp. 701-706).

Garry W. Buchko, et al. Structural features of the minimal DNA binding domain (M98-F219) of human nucleotide excision repair protein XPA; Neucleic Acids Research, 1998, vol. 26, (pp. 2779-2788).

Norie Sugitani, et al., Redefining the DNA-Binding Domain of Human XPA; Journal of the American Chemical Society, 2014; dx.doi.org/10.1021/ja503020f | J. Am. Chem. Soc. 2014, 136, 10830-10833.

Benjamin Hilton, et al., A new structural insight into XPA-DNA interactions; Biosci. Rep. 34(6), art:e00162.doi:10.1042/BSR20140158.

Masafumi Saijo, et al., Nucleotide Excision Repair by Mutant Xeroderma Pigmentosum Group A (XPA) Proteins with Deficiency in Interaction with RPA; The Journal of Biological Chemistry vol. 286, No. 7, pp. 5476-5483, Feb. 18, 2011 © 2011 by The American Society for Biochemistry and Molecular Biology, Inc.

Steve M. Patrick and John J. Turchi; Xeroderma Pigmentosum Complementation Group A Protein (XPA) Modulates RPA-DNA Interactions via Enhanced Complex Stability and Inhibition of Strand Separation Activity; The Journal of Biological Chemistry vol. 277, No. 18, Issue of May 3, p. 16096-16101, 2002.

Sandra C. Koch, et al., Structural insights into the recognition of cisplatin and AAF-dG lesion by Rad14 (XPA); PNAS, Jul. 7, 2015, vol. 112, No. 27, pp. 8272-8277.

Zhengguan Yang, Specific and Efficient Binding of Xeroderma Pigmentosum Complementation Group A to Double-Strand/Single-Strand DNA Junctions with 3' and/or 5'-ssDNA Branches; Biochemistry 2006, 45, 15921-15930.

1 (X80)
$IC_{50}$ = 50-100 μM

XPA INHIBITOR COMPOUNDS AND THEIR USE

CROSS-REFERENCE TO RELATED APPLICATION

This application is a national stage entry under 35 U.S.C. § 371 of PCT International Application No. PCT/US2018/051416, filed Sep. 18, 2018, which claims priority to U.S. Provisional Patent Application No. 62/560,561, filed Sep. 19, 2017, the disclosures of which are expressly incorporated by reference in their entireties.

STATEMENT OF GOVERNMENT RIGHTS

This invention was made with government support under CA180710, CA195926 and TR000006 awarded by the National Institutes of Health. The government has certain rights in the invention.

FIELD

The present disclosure relates to certain compounds having binding affinity for XPA, and uses thereof. Specifically, the present disclosure relates to the use of XPA inhibitors as described herein in in methods of treating cancer.

BACKGROUND

Targeting DNA repair and the DNA damage response for cancer therapy has gained increasing attention with the recent US FDA (December 2014) approval of the poly-ADP ribose polymerase (PARP) inhibitor olaparib (Lynparza™, AstraZeneca) as the first DNA repair targeting agent for cancer treatment. While olaparib is approved as a single agent, the full utility of DNA repair targeted inhibitors can be expanded by their use in combination treatment regimens with DNA damaging chemotherapeutics including the platinum (Pt)-based agents cisplatin, carboplatin and oxaliplatin. However, this utility requires knowledge of the relevant repair pathways involved in repairing and tolerating platinum-induced DNA damage.

Approximately half of all cancer patients who receive anti-cancer chemotherapy are treated with a platinum drug at some point within their treatment regimen with widely varied outcomes. Most cancers display a good initial response, but unfortunately treatment failure ensues due to development of intrinsic or extrinsic drug resistance. There are multiple factors involved in platinum resistance, among them increased capacity of DNA damage repair is of potential concerns. Several studies have revealed that the overexpression of NER proteins (mainly XPA, RPA, ERCC1, XPC and XPF) and repair of DNA damage by these proteins are directly linked to platinum resistance which ultimately hamper the efficacy of platinum-based therapy. The suppression of NER activity has been potentially recognized as a highly effective adjuvant therapy with DNA damaging agents such as platinum drugs and radiotherapy towards maximizing efficacy, overcoming resistance and reducing the toxicities associated with the current regimen. The DNA damage recognition process is the limiting step in NER pathway.

The XPA (Xeroderma Pigmentosum Group A) protein has been shown to bind to the damaged duplex DNA in the DNA damage identification and verification process. XPA does not possess any enzymatic activity, but is an integral component for which there is no redundant or compensatory protein. In addition, XPA has been shown to have a greater affinity for damaged DNA over undamaged DNA and is required for the removal of all types of DNA lesions repaired by NER. In fact, as there are no redundant proteins that can compensate for the loss of XPA activity, decreased expression of XPA has been observed in testicular cancers where 95% of patients are cured by a platinum-based therapy.

Human XPA is a relatively small 273 residue protein (39 kDa) that contains multiple domains and interaction motifs that support binding to DNA and other DNA repair proteins (FIG. 1). (See, Sugitani, N.; Sivley, R. M.; Perry, K. E.; Capra, J. A.; Chazin, W. J. XPA: A key scaffold for human nucleotide excision repair. *DNA Repair* 2016, 44, 123-135; Fadda, E. Role of the XPA protein in the NER pathway: A perspective on the function of structural disorder in macromolecular assembly. *Comput. Struct. Biotechnol. J.* 2016, 14, 78-85; Ikegami, T.; Kuraoka, I.; Saijo, M. et. al. Solution structure of the DNA- and RPA-binding domain of the human repair factor XPA. *Nat. Struct. Biol.* 1998, 5, 701-706; Buchko, G. W.; Ni, S.; Thrall, B. D.; Kennedy, M. A. Structural features of the minimal DNA binding domain (M98-F219) of human nucleotide excision repair protein XPA. *Nucleic Acids Res.* 1998, 26, 2779-2788). The recently refined structural analysis of human XPA revealed that DNA binding activity resides in a 142 amino acid ($XPA_{98-239}$) minimal DNA binding domain (MBD/DBD) spanning from the C4 zinc finger through the α-helix basic motif (Sugitani, N.; Shell, S. M.; Soss, S. E.; Chazin, W. J. Redefining the DNA-binding domain of human XPA. *J. Am. Chem. Soc.* 2014, 136, 10830-10833; Hilton, B.; Shkriabai, N.; Musich, P. R.; Kvaratskhelia, M.; Shell, S.; Zou, Y. A new structural insight into XPA-DNA interactions. *Biosci. Rep.* 2014, 34, 831-840). The zinc containing globular core of XPA is responsible for binding both the ssDNA to dsDNA junction (Y junction) and the RPA70 domain (Saijo, M.; Takedachi, A. Tanaka, K. Nucleotide excision repair by mutant Xeroderma Pigmentosum Group A (XPA) proteins with deficiency in interaction with RPA. *J. Biol. Chem.* 2011, 286, 5476-5483; Patrick, S. M.; Turchi, J. J. Xeroderma pigmentosum complementation group A protein (XPA) modulates RPA-DNA interactions via enhanced complex stability and inhibition of strand separation activity. *J. Biol. Chem.* 2002, 277, 16096-16101). More recently, Koch et. al. reported the first high-resolution X-ray crystal structures of the MBD of the yeast XPA homolog Rad14 bound to damage containing duplex DNA with either a cisplatin lesion (1,2-GG) or an acetylaminofluorene adduct (AAF-dG). (See, Koch, S. C.; Kuper, J.; Gasteiger, K. L.; Simon, N.; Strasser, R.; Eisen, D.; Geiger, S.; Schneider, S.; Kisker, C.; Carell, T. Structural insights into the recognition of cisplatin and AAF-dG lesion by Rad14 (XPA). *Proc. Natl. Acad. Sci. U.S.A* 2015, 112, 8272-8277) The interaction of XPA homolog Rad14 with the ss-dsDNA junction is consistent with previous studies indicating that human XPA also preferentially binds to the DNA junction (Yang, Z.; Roginskaya, M.; Colis, L. C.; Basu, A. K.; Shell, S. M.; Liu, Y.; Musich, P. R.; Harris, C. M.; Harris, T. M.; Zou, Y. Specific and efficient binding of xeroderma pigmentosum complementation group A to double-strand/single-strand DNA junctions with 3'- and/or 5'-ssDNA branches. *Biochemistry* 2006, 45, 15921-15930).

Surprisingly, despite the potential physiological significance and extensive scientific progress on XPA protein, very little progress has been made to date to develop small molecule inhibitors targeting XPA. In our previous studies, a 3-D structure of the XPA MBD revealed a cleft that includes a number of conserved basic amino acids which has direct contact with the DNA in conjunction with surrounding residues and it also has an impact on binding to kinked DNA substrates. (See, Neher, T. M.; Shuck, S. C.; Liu, J. Y; Zhang, J. T.; Turchi, J. J. Identification of novel small molecule inhibitors of the XPA protein using in silico based screening. *ACS Chem. Biol.* 2010, 5, 953-965) With further structure-based in silico screening of a virtual small molecule library targeting this cleft, we identified 5-(5-((1-(3-carboxyphenyl)-3-methyl-5-oxo-1,5-dihydro-4H-pyrazol-4-ylidene)methyl)furan-2-yl)-2-chlorobenzoic acid (X80) as an XPA-DNA interaction inhibitor.

Inhibitors targeting XPA-DNA interfaces hold great potential to enhance the efficiency of treatment with DNA damaging agents and reverse platinum drug resistance by reducing NER activity, and there exists a great unmet need for the development of XPA inhibitors that provide advantageous properties, such as enhanced solubility and metabolic stability, while also showing good potency when adminstered either alone or in combination with another therapeutic agent.

SUMMARY

It has been discovered that certain aryl-pyrazone compounds show activity against XPA and can be applied in methods of treating cancer. In one aspect, the present disclosure provides for a method of treating cancer in a patient comprising a. administering a therapeutically effective amount of and XPA inhibitor, such as a compound of the formula II, or a pharmaceutically acceptable salt thereof,

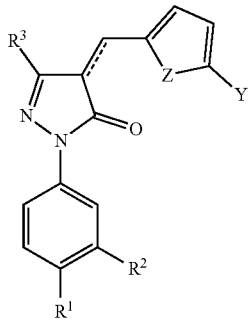

II wherein $R^1$, $R^2$, $R^3$, Y and Z are as defined herein, and the compound is not of the formula

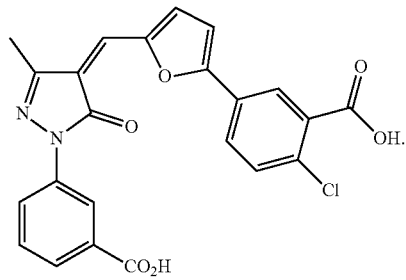 [SMILES: CC1=NN(c2cccc(C(=O)O)c2)C(=O)/C1=C\c1ccc(-c2ccc(Cl)c(C(=O)O)c2)o1]

In some embodiments, the method further comprises (b) administering at least one additional cancer therapy.

In another aspect, the present disclosure provides for a method of treating cancer in a patient comprising a. administering a therapeutically effective amount of an XPA inhibitor, such as a compound of the formula II, or a pharmaceutically acceptable salt thereof,

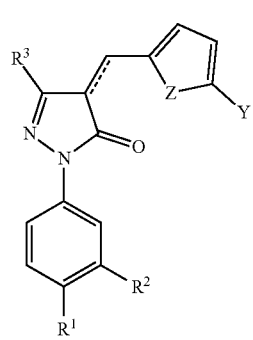

II wherein $R^1$, $R^2$, $R^3$, Y and Z are as defined herein, and the compound is not of the formula

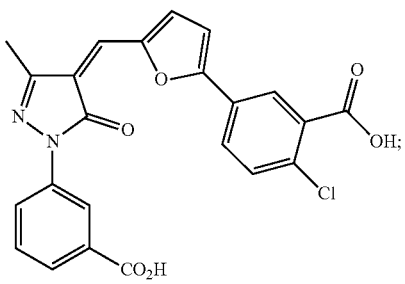 [SMILES: CC1=NN(c2cccc(C(=O)O)c2)C(=O)/C1=C\c1ccc(-c2ccc(Cl)c(C(=O)O)c2)o1]

and b. administering a therapeutically effective amount of an additional cancer therapy.

In another aspect, the present disclosure provides a method of treating cancer in a patient comprising a. administering a therapeutically effective amount of an XPA inhibitor, such as a compound of the formula II, or a pharmaceutically acceptable salt thereof,

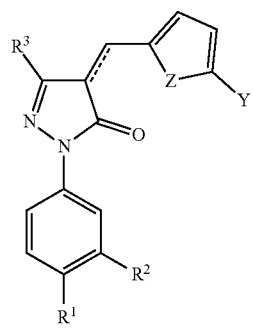

II wherein $R^1$, $R^2$, $R^3$, Y and Z are as defined herein, and the compound is not of the formula

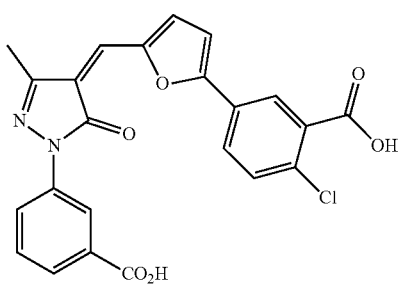 [SMILES: CC1=NN(c2cccc(C(=O)O)c2)C(=O)/C1=C\c1ccc(-c2ccc(Cl)c(C(=O)O)c2)o1]

to a patient that was previously administered an additional additional cancer therapy.

In another aspect, the disclosure is directed to an XPA inhibitor compound of the formula II, or a pharmaceutically acceptable salt thereof,

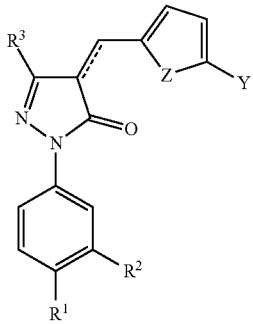

wherein $R^1$, $R^2$, $R^3$, Y and Z are as defined herein, and the compound is not of the formula

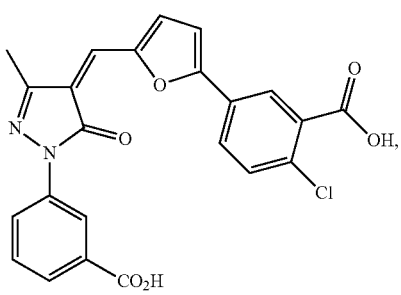

for use in the treatment of cancer in a patient.

In another aspect, the disclosure is directed to an XPA inhibitor compound of the formula II, or a pharmaceutically acceptable salt thereof,

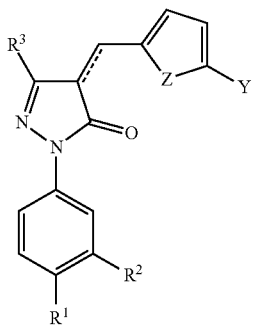

wherein $R^1$, $R^2$, $R^3$, Y and Z are as defined herein, and the compound is not of the formula

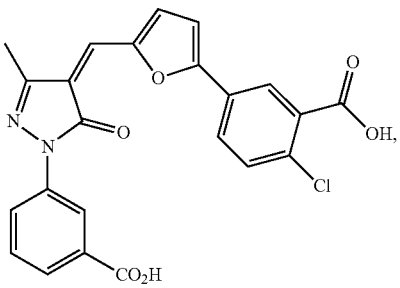 [SMILES: CC1=NN(c2cccc(C(=O)O)c2)C(=O)/C1=C\c1ccc(-c2ccc(Cl)c(C(=O)O)c2)o1]

in combination with a therapeutically effective amount of at least one additional cancer therapy, for use in the treatment of cancer in a patient.

In another aspect, the disclosure is directed to use of an XPA inhibitor, such as a compound of the formula II, or a pharmaceutically acceptable salt thereof,

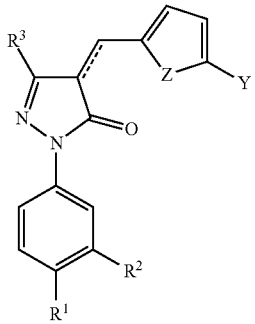

wherein $R^1$, $R^2$, $R^3$, Y and Z are as defined herein, and the compound is not of the formula

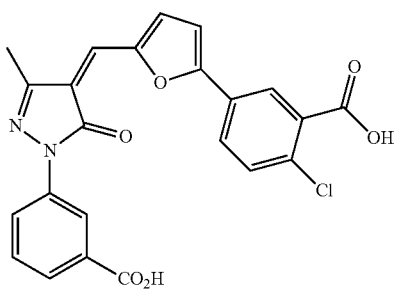 [SMILES: CC1=NN(c2cccc(C(=O)O)c2)C(=O)/C1=C\c1ccc(-c2ccc(Cl)c(C(=O)O)c2)o1]

for use in the treatment of cancer in a patient. In some embodiments of this aspect, the compound is administered in combination with a therapeutically effective amount of at least one additional cancer therapy.

In another aspect, the disclosure is directed to use of an XPA inhibitor, such as a compound of the formula II, or a pharmaceutically acceptable salt thereof,

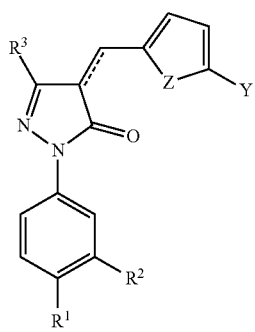

II wherein $R^1$, $R^2$, $R^3$, Y and Z are as defined herein, and the compound is not of the formula

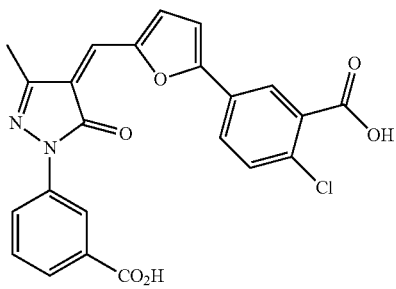

in the preparation of a medicament for the treatment of cancer in a patient. In some embodiments of this aspect, the compound is administered in combination with a therapeutically effective amount of at least one additional cancer therapy.

In another aspect, the disclosure is directed to a composition comprising an XPA inhibitor, such as a compound of the formula II, or a pharmaceutically acceptable salt thereof,

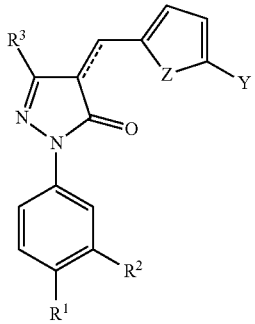

II wherein $R^1$, $R^2$, $R^3$, Y and Z are as defined herein, and the compound is not of the formula

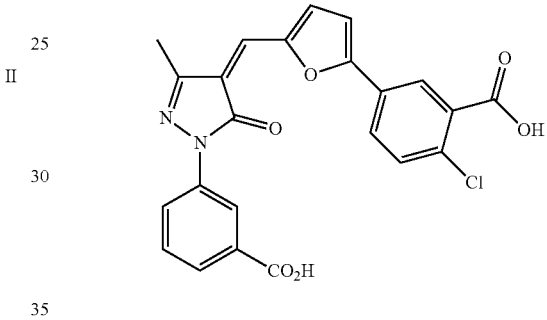

in a therapeutically effective amount, for use in the treatment of cancer in a patient. In some embodiments of this aspect, the composition is administered in combination with a therapeutically effective amount of at least one additional cancer therapy.

In yet another aspect, the disclosure relates to a synergistic composition of an XPA inhibitor, such as a compound of the formula II, or a pharmaceutically acceptable salt thereof,

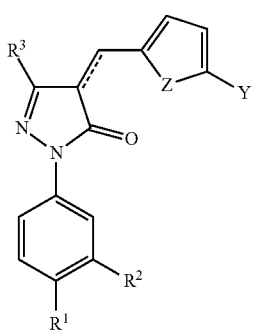

II wherein $R^1$, $R^2$, $R^3$, Y and Z are as defined herein, and the compound is not of the formula

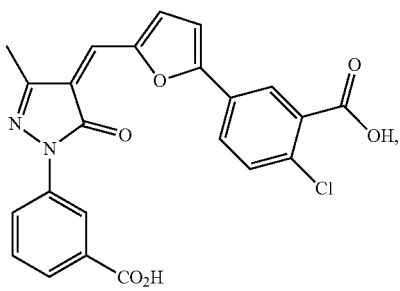 [SMILES: CC1=NN(c2cccc(C(=O)O)c2)C(=O)/C1=C\c1ccc(-c2ccc(Cl)c(C(=O)O)c2)o1]

and
an additional cancer therapy, where the two components come into contact with each other at a locus.

In some embodiments of these aspects, the XPA inhibitor is a compound is of the formula Ia, Ia

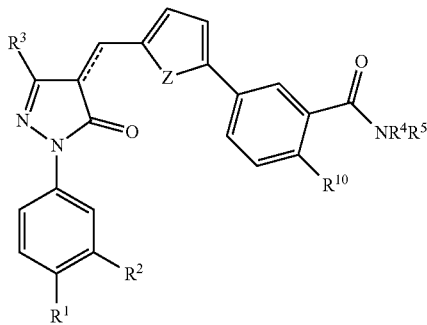

or a pharmaceutically acceptable salt thereof, wherein $R^1$, $R^2$, $R^3$, $R^4$, $R^5$, $R^{10}$ and Z are as defined herein.

In some embodiments of these aspects, the XPA inhibitor is a compound is of the formula Ib Ib

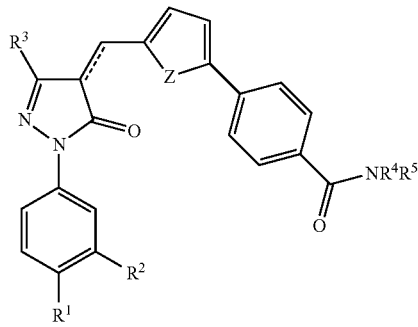

or a pharmaceutically acceptable salt thereof, wherein $R^1$, $R^2$, $R^3$, $R^4$, $R^5$, X and Z are as defined herein.

In some embodiments of these aspects, the additional cancer therapy is a platinum drug. In some embodiments, the additional cancer therapy is selected from the group consisting of cisplatin, carboplatin, oxaliplatin, nedaplatin, triplatin tetranitrate, phenanthriplatin, picoplatin, and satraplatin.

Additional embodiments, features, and advantages of the disclosure will be apparent from the following detailed description and through practice of the disclosure. The aspects of the present disclosure can be described as embodiments in any of the following enumerated clauses. It will be understood that any of the embodiments described herein can be used in connection with any other embodiments described herein to the extent that the embodiments do not contradict one another. For example, each of the aspects described above defining a method, compound, use or synergistic composition may be combined with the following enumerated clauses to provide additional embodiments of the disclosure.

1. A method of treating cancer in a patient comprising
   a. administering a therapeutically effective amount of an XPA inhibitor, such as a compound of the formula II, or a pharmaceutically acceptable salt thereof,

II

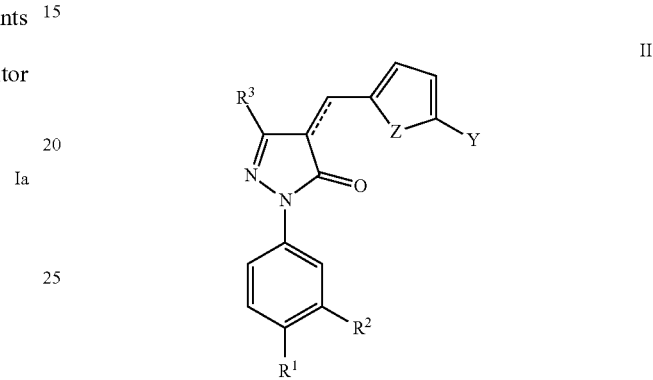

wherein
Z is O or S;
$R^1$ and $R^2$ are independently selected from the group consisting of H, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^6$, —CN, —$NO_2$, —C(O)$R^6$, —$CO_2R^6$, —C(O)$NR^6R^7$, —OS(O)$R^6$, —OS(O)$_2R^6$, —$SR^6$, —S(O)$R^6$, —S(O)$_2R^6$, —S(O)$NR^6R^7$, —S(O)$_2NR^6R^7$, —OS(O)$NR^6R^7$, —OS(O)$_2NR^6R^7$, and —$NR^6R^7$; wherein each hydrogen atom in $C_1$-$C_6$ alkyl, $C_2$-$C_6$ alkenyl, $C_2$-$C_6$ alkynyl or $C_3$-$C_6$ cycloalkyl is independently optionally substituted with halogen;

$R^3$ is H, halogen, or $C_1$-$C_6$ alkyl, wherein each hydrogen atom in $C_1$-$C_6$ alkyl, $C_2$-$C_6$ alkenyl, $C_2$-$C_6$ alkynyl or $C_3$-$C_6$ cycloalkyl is independently optionally substituted with halogen;

Y is —C(O)$NR^4R^5$ or phenyl, wherein each hydrogen atom in phenyl is optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^4$, —CN, —$NO_2$, —C(O)$R^4$, —$CO_2R^4$, —C(O)$NR^4R^5$, —OS(O)$R^4$, —OS(O)$_2R^4$, —$SR^4$, —S(O)$R^4$, —S(O)$_2R^4$, —S(O)$NR^4R^5$, —S(O)$_2NR^4R^5$, —OS(O)$NR^4R^5$, —OS(O)$_2NR^4R^5$, and —$NR^4R^5$, or two adjacent hydrogen atoms on phenyl are optionally substituted with a group that combines with the carbon atoms to which they are attached to form a 5- to 7-membered heterocycloalkyl ring;

$R^4$ and $R^5$ are each independently selected from the group consisting of H, $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl), —$C_1$-$C_6$ alkyl-($C_6$-$C_{10}$ aryl), 3- to 7-membered heterocycloalkyl, $C_6$-$C_{10}$ aryl and 5- to 7-membered heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl) or —$C_1$-$C_6$ alkyl-($C_6$-$C_{10}$ aryl) is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —OR⁸, —CN, —NO₂, —C(O)R⁸, —CO₂R⁸, —C(O)NR⁸R⁹, —OS(O)R⁸, —OS(O)₂R⁸, —SR⁸, —S(O)R⁸, —S(O)₂R⁸, —S(O)NR⁸R⁹, —S(O)₂NR⁸R⁹, —OS(O)NR⁸R⁹, —OS(O)₂NR⁸R⁹, and —NR⁸R⁹;

each $R^6$, $R^7$, $R^8$ and $R^9$ is independently selected from the group consisting of H, $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl), —$C_1$-$C_6$ alkyl-($C_6$-$C_{10}$ aryl), 3- to 7-membered heterocycloalkyl and $C_6$-$C_{10}$ aryl; $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl) or —$C_1$-$C_6$ alkyl-($C_6$-$C_{10}$ aryl) is independently optionally substituted with halogen, and ===== is either a single bond or a pi-bond; and the compound is not of the formula

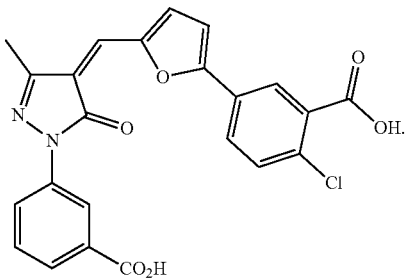 [SMILES: CC1=NN(c2cccc(C(=O)O)c2)C(=O)/C1=C\c1ccc(-c2ccc(Cl)c(C(=O)O)c2)o1]

2. The method of clause 1, wherein the XPA inhibitor is a compound is of the formula I, or a pharmaceutically acceptable salt thereof,

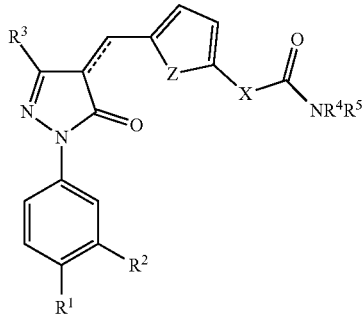

wherein

X is absent or $C_6$-$C_{10}$ aryl, wherein each hydrogen in $C_6$-$C_{10}$ aryl is optionally substituted with an $R^{10}$;

Z is O or S;

$R^1$ and $R^2$ are independently selected from the group consisting of H, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —OR⁶, —CN, —NO₂, —C(O)R⁶, —CO₂R⁶, —C(O)NR⁶R⁷, —OS(O)R⁶, —OS(O)₂R⁶, —SR⁶, —S(O)R⁶, —S(O)₂R⁶, —S(O)NR⁶R⁷, —S(O)₂NR⁶R⁷, —OS(O)NR⁶R⁷, —OS(O)₂NR⁶R⁷, and —NR⁶R⁷; wherein each hydrogen atom in $C_1$-$C_6$ alkyl, $C_2$-$C_6$ alkenyl, $C_2$-$C_6$ alkynyl or $C_3$-$C_6$ cycloalkyl is independently optionally substituted with halogen;

$R^3$ is H, halogen, or $C_1$-$C_6$ alkyl, wherein each hydrogen atom in $C_1$-$C_6$ alkyl, $C_2$-$C_6$ alkenyl, $C_2$-$C_6$ alkynyl or $C_3$-$C_6$ cycloalkyl is independently optionally substituted with halogen;

$R^4$ and $R^5$ are each independently selected from the group consisting of H, $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl), —$C_1$-$C_6$ alkyl-($C_6$-$C_{10}$ aryl), 3- to 7-membered heterocycloalkyl, $C_6$-$C_{10}$ aryl and 5- to 7-membered heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl), —$C_1$-$C_6$ alkyl-($C_6$-$C_{10}$ aryl) or $C_6$-$C_{10}$ aryl is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —OR⁸, —CN, —NO₂, —C(O)R⁸, —CO₂R⁸, —C(O)NR⁸R⁹, —OS(O)R⁸, —OS(O)₂R⁸, —SR⁸, —S(O)R⁸, —S(O)₂R⁸, —S(O)NR⁸R⁹, —S(O)₂NR⁸R⁹, —OS(O)NR⁸R⁹, —OS(O)₂NR⁸R⁹, and —NR⁸R⁹, provided that one of $R^4$ or $R^5$ is not H;

$R^6$, $R^7$, $R^8$, $R^9$, $R^{11}$ and $R^{12}$ are each independently selected from the group consisting of H, $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl), —$C_1$-$C_6$ alkyl-($C_6$-$C_{10}$ aryl), 3- to 7-membered heterocycloalkyl and $C_6$-$C_{10}$ aryl; and $R^{10}$ is selected from the group consisting of halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —OR¹¹, —CN, —NO₂, —C(O)R¹¹, —CO₂R¹¹, —C(O)NR¹¹R¹², —OS(O)R¹¹, —OS(O)₂R¹¹, —SR¹¹, —S(O)R¹¹, —S(O)₂R¹¹, —S(O)NR¹¹R¹², —S(O)₂NR¹¹R¹², —OS(O)NR¹¹R¹², —OS(O)₂NR¹¹R¹², and —NR¹¹R¹²;

===== is either a single bond or a pi-bond.

3. The method of clause 1 or 2, wherein the XPA inhibitor is a compound is of the formula Ia,

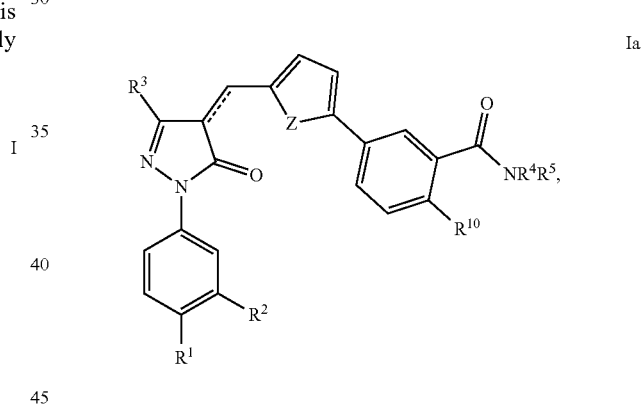

or a pharmaceutically acceptable salt thereof.

4. The method of any one of the preceding clauses, wherein $R^{10}$ is chloro.

5. The method of clause 1 or 2, wherein the XPA inhibitor is a compound is of formula Ib

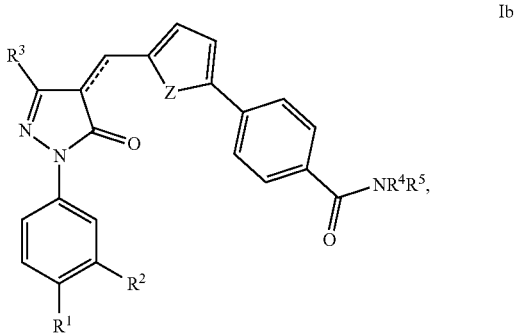

or a pharmaceutically acceptable salt thereof.

6. The method of any one of the preceding clauses, wherein Z is O.

7. The method of any one of clauses 1 to 5, wherein Z is S.

8. The method of any one of the preceding clauses, wherein $R^4$ is $C_6$-$C_{10}$ aryl, wherein each hydrogen atom in $C_6$-$C_{10}$ aryl is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —$C(O)R^8$, —$CO_2R^8$, —$C(O)NR^8R^9$, —$OS(O)R^8$, —$OS(O)_2R^8$, —$SR^8$, —$S(O)R^8$, —$S(O)_2R^8$, —$S(O)NR^8R^9$, —$S(O)_2NR^8R^9$, —$OS(O)NR^8R^9$, —$OS(O)_2NR^8R^9$, or —$NR^8R^9$.

9. The method of any one of the preceding clauses, wherein $R^4$ is $C_6$-$C_{10}$ aryl, wherein $C_6$-$C_{10}$ aryl is substituted with at least one halogen or —$OR^8$.

10. The method of any one of the preceding clauses, wherein $R^4$ is phenyl, wherein each hydrogen atom in phenyl is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —$C(O)R^8$, —$CO_2R^8$, —$C(O)NR^8R^9$, —$OS(O)R^8$, —$OS(O)_2R^8$, —$SR^8$, —$S(O)R^8$, —$S(O)_2R^8$, —$S(O)NR^8R^9$, —$S(O)_2NR^8R^9$, —$OS(O)NR^8R^9$, —$OS(O)_2NR^8R^9$, or —$NR^8R^9$.

11. The method of any one of the preceding clauses, wherein $R^4$ is phenyl substituted with at least one halogen or —$OR^8$.

12. The method of any one of clauses 1 to 7, wherein $R^4$ is —$C_1$-$C_6$ alkyl-($C_3$-$C_6$ cycloalkyl).

13. The method of any one of clauses 1 to 7, wherein $R^4$ is —$C_1$-$C_6$ alkyl-($C_6$-$C_{10}$ aryl), and each hydrogen atom in $C_6$-$C_{10}$ aryl is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —$C(O)R^8$, —$CO_2R^8$, —$C(O)NR^8R^9$, —$OS(O)R^8$, —$OS(O)_2R^8$, —$SR^8$, —$S(O)R^8$, —$S(O)_2R^8$, —$S(O)NR^8R^9$, —$S(O)_2NR^8R^9$, —$OS(O)NR^8R^9$, —$OS(O)_2NR^8R^9$, or —$NR^8R^9$.

14. The method of any one of clauses 1 to 7 or 13, wherein $R^4$ is —$C_1$-$C_6$ alkyl-($C_6$-$C_{10}$ aryl), wherein $C_6$-$C_{10}$ aryl is substituted with at least one halogen or —$OR^8$.

15. The method of any one of clauses 1 to 7, 13 or 14, wherein $R^4$ is benzyl, wherein each hydrogen atom in benzyl is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —$C(O)R^8$, —$CO_2R^8$, —$C(O)NR^8R^9$, —$OS(O)R^8$, —$OS(O)_2R^8$, —$SR^8$, —$S(O)R^8$, —$S(O)_2R^8$, —$S(O)NR^8R^9$, —$S(O)_2NR^8R^9$, —$OS(O)NR^8R^9$, —$OS(O)_2NR^8R^9$, or —$NR^8R^9$.

16. The method of any one of clauses 1 to 7 or 13 to 15, wherein $R^4$ is benzyl substituted with at least one halogen or —$OR^8$.

17. The method of any one of clauses 1 to 7, wherein $R^4$ selected from the group consisting of

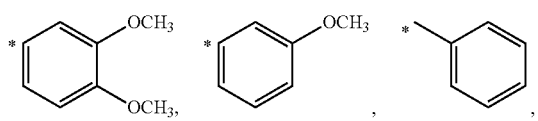

-continued

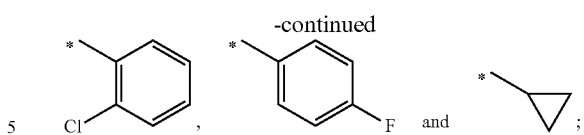

wherein * represent the point of attachment of $R^4$ to the amide nitrogen.

18. The method of any one of the preceding clauses, wherein $R^5$ is H.

19. The method of any one of the preceding clauses, wherein $R^3$ is $C_1$-$C_6$ alkyl.

20. The method of any one of the preceding clauses, wherein $R^3$ is methyl.

21. The method of any one of the preceding clauses, wherein $R^1$ and $R^2$ are each independently H, 5- to 7-membered heteroaryl, —CN, —$CO_2R^6$ or —$S(O)_2NR^6R^7$, provided that at least one of $R^1$ and $R^2$ is not H.

22. The method of any one of the preceding clauses, wherein $R^1$ is H and $R^2$ is —$CO_2R^6$.

23. The method of any one of clauses 1 to 21, wherein $R^1$ is —$CO_2R^6$, and $R^2$ is H.

24. The method of any one of clauses 1 to 21, wherein $R^2$ is —$CO_2R^6$, and $R^6$ is H.

25. The method of any one of clauses 1 to 21, wherein $R^2$ is —$CO_2R^6$, and $R^6$ is ethyl.

26. The method of any one of clauses 1 to 21 or 23, wherein $R^1$ is —$CO_2R^6$, and $R^6$ is H.

27. The method of any one of clauses 1 to 21 or 23, wherein $R^1$ is —$CO_2R^6$, and $R^6$ is ethyl.

28. The method of any one of the preceding clauses, wherein ===== is a single bond.

29. The method of any one of clauses 1 to 29, wherein ===== is a pi-bond.

30. The method of any one of the preceding clauses, wherein the compound is of a formula selected from the group consisting of

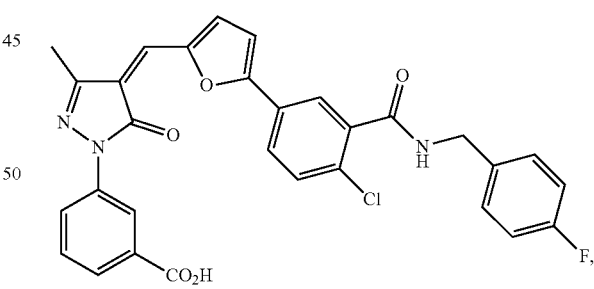

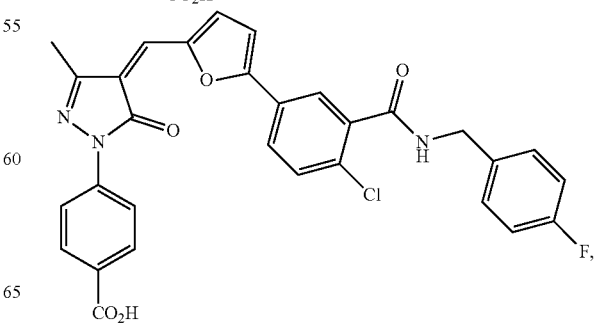

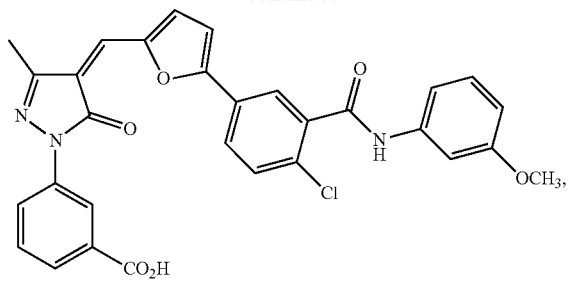
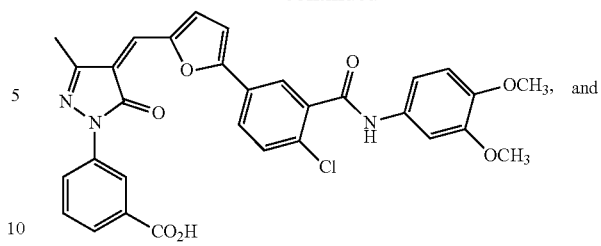
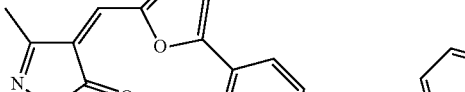
or a pharmaceutically acceptable salt thereof.
31. The method of any one of the preceding clauses, wherein the compound is of a formula selected from the group consisting of
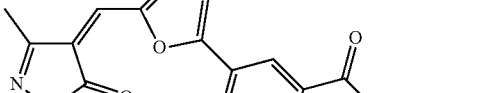

17
-continued

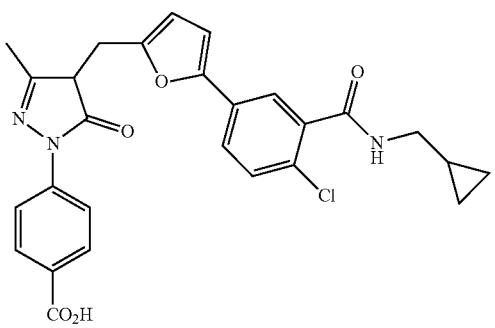

and

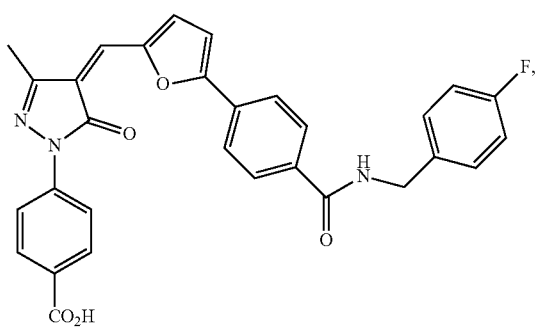

or a pharmaceutically acceptable salt thereof.

32. The method of any one of the preceding clauses further comprising (b) administering at least one additional cancer therapy.

33. The method of any one of the preceding clauses further comprising (b) administering at least one additional cancer therapy that is a platinum drug.

34. The method of any one of the preceding clauses further comprising (b) administering at least one additional cancer therapy that is selected from the group consisting of cisplatin, carboplatin, oxaliplatin, nedaplatin, triplatin tetranitrate, phenanthriplatin, picoplatin, and satraplatin.

35. A method of treating cancer in a patient comprising
    a. administering a therapeutically effective amount of a compound of the formula II, or a pharmaceutically acceptable salt thereof,

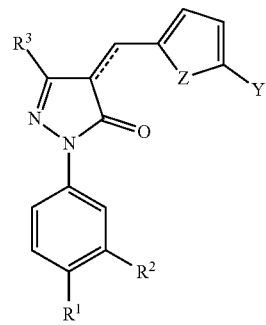

II wherein $R^1$, $R^2$, $R^3$, Y and Z are as defined herein, and the compound is not of the formula

18

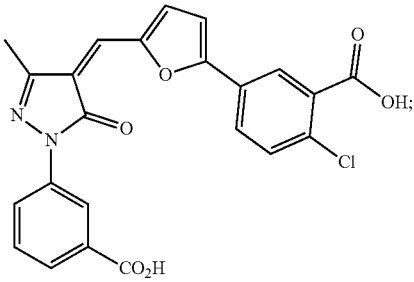 [SMILES: CC1=NN(c2cccc(C(=O)O)c2)C(=O)/C1=C\c1ccc(-c2ccc(Cl)c(C(=O)O)c2)o1]

and
    b. administering a therapeutically effective amount of an additional cancer therapy.

36. A method of treating cancer in a patient comprising
    a. administering a therapeutically effective amount of a compound of the formula II, or a pharmaceutically acceptable salt thereof,

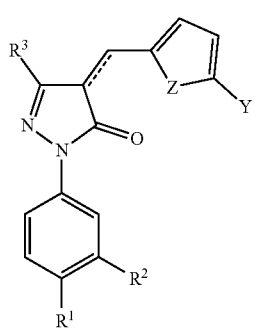

II wherein $R^1$, $R^2$, $R^3$, Y and Z are as defined herein, and the compound is not of the formula

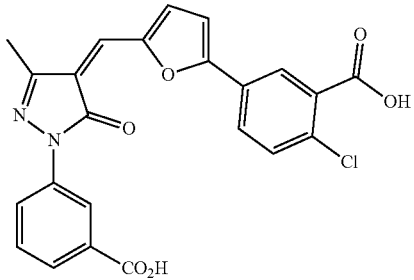 [SMILES: CC1=NN(c2cccc(C(=O)O)c2)C(=O)/C1=C\c1ccc(-c2ccc(Cl)c(C(=O)O)c2)o1]

to a patient that was previously administered an additional cancer therapy.

37. A compound of the formula II, or a pharmaceutically acceptable salt thereof,

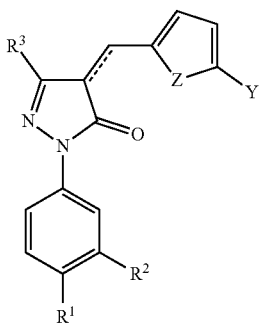

wherein $R^1$, $R^2$, $R^3$, Y and Z are as defined herein, and the compound is not of the formula

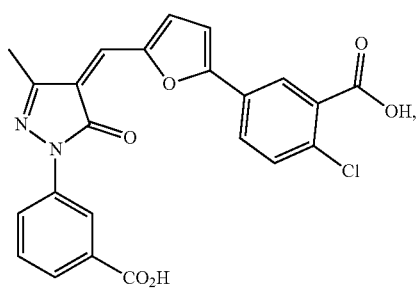 [SMILES: CC1=NN(c2cccc(C(=O)O)c2)C(=O)/C1=C\c1ccc(-c2ccc(Cl)c(C(=O)O)c2)o1]

for use in the treatment of cancer in a patient.

38. A compound of the formula II, or a pharmaceutically acceptable salt thereof,

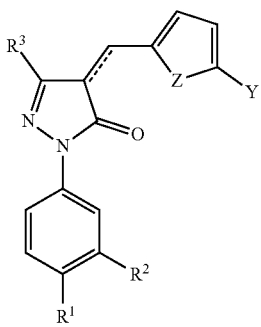

wherein $R^1$, $R^2$, $R^3$, Y and Z are as defined herein, and the compound is not of the formula

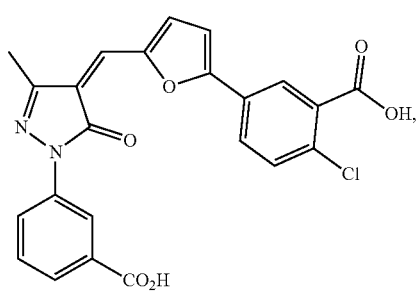 [SMILES: CC1=NN(c2cccc(C(=O)O)c2)C(=O)/C1=C\c1ccc(-c2ccc(Cl)c(C(=O)O)c2)o1]

in combination with a therapeutically effective amount of at least one additional cancer therapy, for use in the treatment of cancer in a patient.

39. A compound of the formula II, or a pharmaceutically acceptable salt thereof,

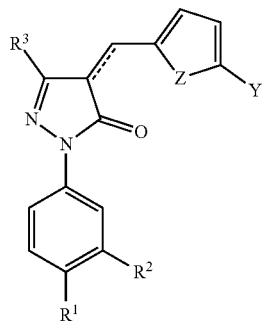

wherein $R^1$, $R^2$, $R^3$, Y and Z are as defined herein, and the compound is not of the formula

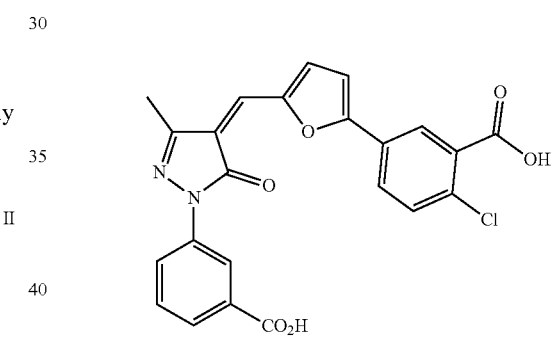

for use in the treatment of cancer in a patient in combination with a therapeutically effective amount of at least one additional cancer therapy.

40. A composition comprising a compound of the formula II, or a pharmaceutically acceptable salt thereof,

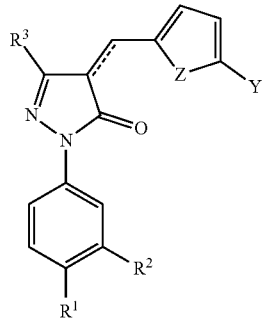

wherein $R^1$, $R^2$, $R^3$, Y and Z are as defined herein, and the compound is not of the formula

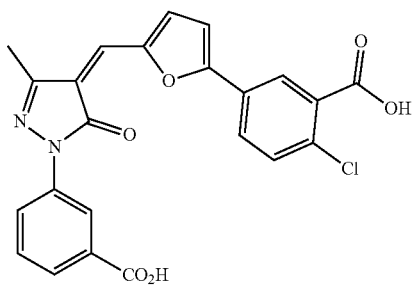 [SMILES: CC1=NN(c2cccc(C(=O)O)c2)C(=O)/C1=C\c1ccc(-c2ccc(Cl)c(C(=O)O)c2)o1]

in a therapeutically effective amount, for use in the treatment of cancer in a patient in combination with a therapeutically effective amount of at least one additional cancer therapy.

41. Use of a compound of the formula II, or a pharmaceutically acceptable salt thereof,

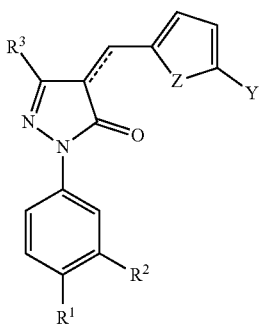

II wherein $R^1$, $R^2$, $R^3$, Y and Z are as defined herein, and the compound is not of the formula

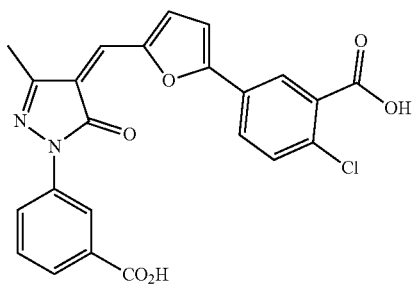 [SMILES: CC1=NN(c2cccc(C(=O)O)c2)C(=O)/C1=C\c1ccc(-c2ccc(Cl)c(C(=O)O)c2)o1]

in the preparation of a medicament for the treatment of cancer in a patient, in combination with a therapeutically effective amount of at least one additional cancer therapy.

42. A synergistic composition of a compound of the formula II, or a pharmaceutically acceptable salt thereof,

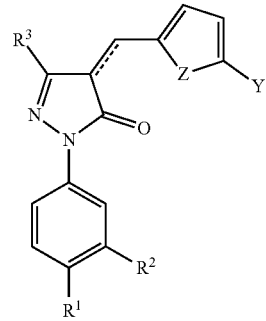

II wherein $R^1$, $R^2$, $R^3$, Y and Z are as defined herein, and the compound is not of the formula

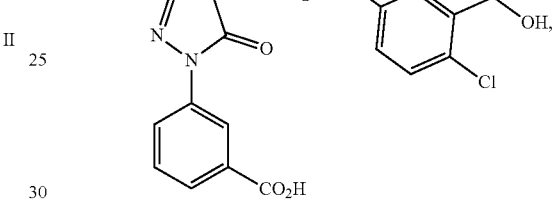

and
an additional cancer therapy, where the two components come into contact with each other at a locus.

BRIEF DESCRIPTION OF THE DRAWINGS

FIG. 4A shows EMSA with increasing concentration of compound 1 (X80) (12.5-100 µM) and 22 (1.6-25 µM) relative to DMSO control on full-length XPA (FL XPA) and XPA$_{98-239}$ DBD. FIG. 4B shows the quantification and concentration-dependent analysis of DNA-binding activity of compound 1 and 22 relative to DMSO control on full-length XPA and XPA$_{98-239}$ DBD.

FIG. 5A shows Molecular interactions of compound 22 Z-isomer with hXPA. FIG. 5B shows molecular interactions of compound 34i Z-isomer with hXPA. Interactions with amino acid side chains are indicated with the dashed lines, π-π stacking interactions are shown in solid dumbbell, cation-π interactions are shown in solid one sided arrow and salt-bridge interactions are shown in dashed two sided arrow. Distances indicated in Å.

DETAILED DESCRIPTION

Figure 1:
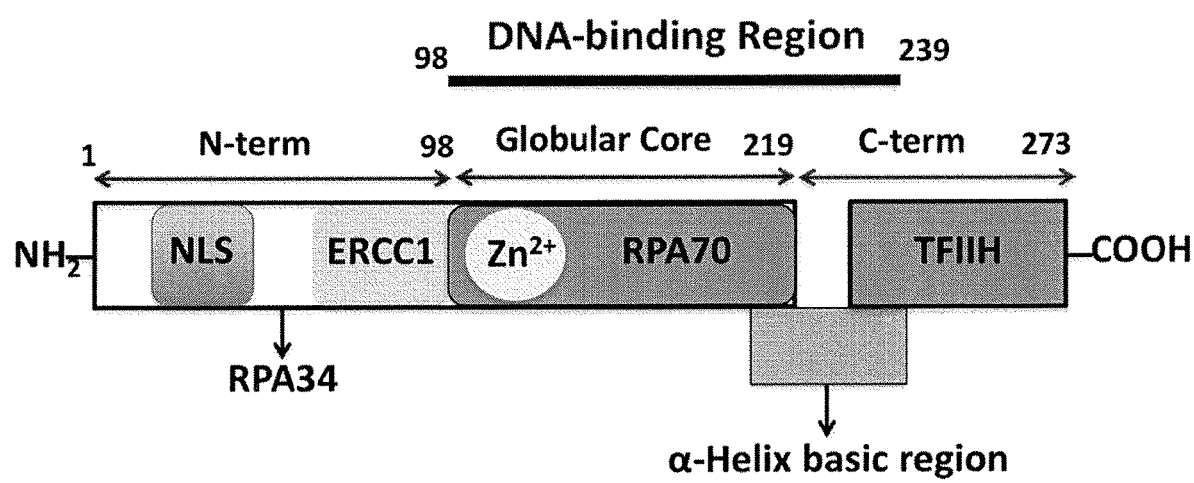
FIG. 1 shows a schematic representation of human XPA protein and XPA interaction partners, mainly NER proteins.

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Chemical nomenclature for compounds described herein has generally been derived using the commercially-available ACD/Name 2014 (ACD/Labs) or ChemBioDraw Ultra 13.0 (Perkin Elmer).

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination. All combinations of the embodiments pertaining to the chemical groups represented by the variables are specifically embraced by the present disclosure and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present disclosure and are disclosed herein just as if each and every such sub-combination of chemical groups was individually and explicitly disclosed herein.

Definitions

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{12}$, $C_1$-$C_{10}$, $C_1$-$C_9$, $C_1$-$C_8$, $C_1$-$C_7$, $C_1$-$C_6$, and $C_1$-$C_4$. Illustratively, such particularly limited length alkyl groups, including $C_1$-$C_8$, $C_1$-$C_7$, $C_1$-$C_6$, and $C_1$-$C_4$, and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, oxo, (═O), thiocarbonyl, O-carbamyl, N-carbamyl, O-thiocarbamyl, N-thiocarbamyl, C-amido, N-amido, C-carboxy, O-carboxy, nitro, and amino, or as described in the various embodiments provided herein. It will be understood that "alkyl" may be combined with other groups, such as those provided above, to form a functionalized alkyl. By way of example, the combination of an "alkyl" group, as described herein, with a "carboxy" group may be referred to as a "carboxyalkyl" group. Other non-limiting examples include hydroxyalkyl, aminoalkyl, and the like.

As used herein, the term "alkenyl" includes a chain of carbon atoms, which is optionally branched, and contains from 2 to 20 carbon atoms, and also includes at least one carbon-carbon double bond (i.e. C═C). It will be understood that in certain embodiments, alkenyl may be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkenyl groups, including $C_2$-$C_8$, $C_2$-$C_7$, $C_2$-$C_6$, and $C_2$-$C_4$ may be referred to as lower alkenyl. Alkenyl may be unsubstituted, or substituted as described for alkyl or as described in the various embodiments provided herein. Illustrative alkenyl groups include, but are not limited to, ethenyl, 1-propenyl, 2-propenyl, 1-, 2-, or 3-butenyl, and the like.

As used herein, the term "alkynyl" includes a chain of carbon atoms, which is optionally branched, and contains from 2 to 20 carbon atoms, and also includes at least one carbon-carbon triple bond (i.e. C≡C). It will be understood that in certain embodiments, alkynyl may each be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkynyl groups, including $C_2$-$C_8$, $C_2$-$C_7$, $C_2$-$C_6$, and $C_2$-$C_4$ may be referred to as lower alkynyl. Alkenyl may be unsubstituted, or substituted as described for alkyl or as described in the various embodiments provided herein. Illustrative alkenyl groups include, but are not limited to, ethynyl, 1-propynyl, 2-propynyl, 1-, 2-, or 3-butynyl, and the like.

As used herein, the term "aryl" refers to an all-carbon monocyclic or fused-ring polycyclic groups of 6 to 12 carbon atoms having a completely conjugated pi-electron system. It will be understood that in certain embodiments, aryl may be advantageously of limited size such as $C_6$-$C_{10}$ aryl. Illustrative aryl groups include, but are not limited to, phenyl, naphthalenyl and anthracenyl. The aryl group may be unsubstituted, or substituted as described for alkyl or as described in the various embodiments provided herein.

As used herein, the term "cycloalkyl" refers to a 3 to 15 member all-carbon monocyclic ring, including an all-carbon 5-member/6-member or 6-member/6-member fused bicyclic ring, or a multicyclic fused ring (a "fused" ring system means that each ring in the system shares an adjacent pair of carbon atoms with each other ring in the system) group, where one or more of the rings may contain one or more double bonds but the cycloalkyl does not contain a completely conjugated pi-electron system. It will be understood that in certain embodiments, cycloalkyl may be advantageously of limited size such as $C_3$-$C_{13}$, $C_3$-$C_9$, $C_3$-$C_6$ and $C_4$-$C_6$. Cycloalkyl may be unsubstituted, or substituted as described for alkyl or as described in the various embodiments provided herein. Illustrative cycloalkyl groups include, but are not limited to, cyclopropyl, cyclobutyl, cyclopentyl, cyclopentenyl, cyclopentadienyl, cyclohexyl, cyclohexenyl, cycloheptyl, adamantyl, norbornyl, norbornenyl, 9H-fluoren-9-yl, and the like. Illustrative examples of cycloalkyl groups shown in graphical representations include the following entities, in the form of properly bonded moieties:

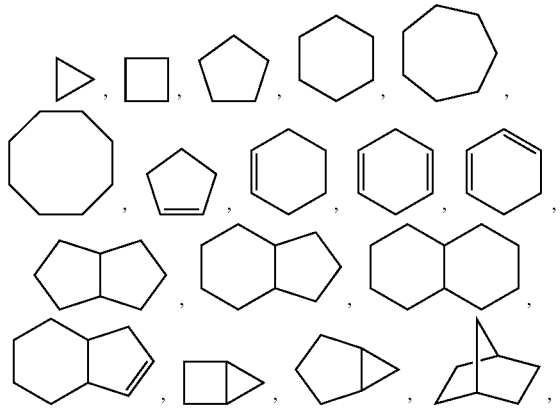

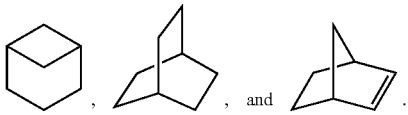

As used herein, the term "heterocycloalkyl" refers to a monocyclic or fused ring group having in the ring(s) from 3 to 12 ring atoms, in which at least one ring atom is a heteroatom, such as nitrogen, oxygen or sulfur, the remaining ring atoms being carbon atoms. Heterocycloalkyl may optionally contain 1, 2, 3 or 4 heteroatoms. Heterocycloalkyl may also have one of more double bonds, including double bonds to nitrogen (e.g. C=N or N=N) but does not contain a completely conjugated pi-electron system. It will be understood that in certain embodiments, heterocycloalkyl may be advantageously of limited size such as 3- to 7-membered heterocycloalkyl, 5- to 7-membered heterocycloalkyl, and the like. Heterocycloalkyl may be unsubstituted, or substituted as described for alkyl or as described in the various embodiments provided herein. Illustrative heterocycloalkyl groups include, but are not limited to, oxiranyl, thianaryl, azetidinyl, oxetanyl, tetrahydrofuranyl, pyrrolidinyl, tetrahydropyranyl, piperidinyl, 1,4-dioxanyl, morpholinyl, 1,4-dithianyl, piperazinyl, oxepanyl, 3,4-dihydro-2H-pyranyl, 5,6-dihydro-2H-pyranyl, 2H-pyranyl, 1, 2, 3, 4-tetrahydropyridinyl, and the like. Illustrative examples of heterocycloalkyl groups shown in graphical representations include the following entities, in the form of properly bonded moieties:

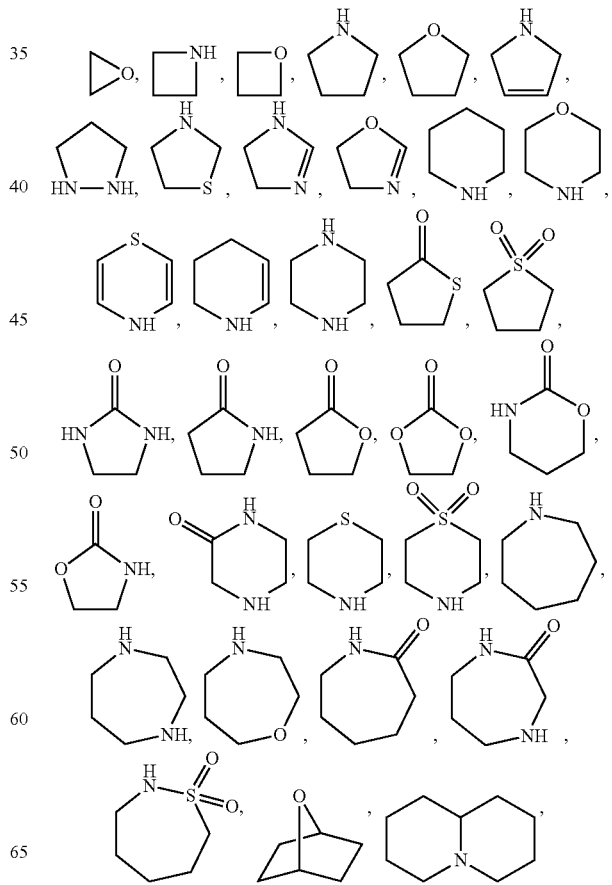

-continued

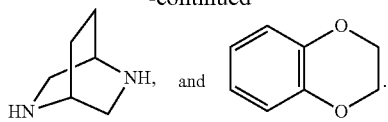

As used herein, the term "heteroaryl" refers to a monocyclic or fused ring group of 5 to 12 ring atoms containing one, two, three or four ring heteroatoms selected from nitrogen, oxygen and sulfur, the remaining ring atoms being carbon atoms, and also having a completely conjugated pi-electron system. It will be understood that in certain embodiments, heteroaryl may be advantageously of limited size such as 3- to 7-membered heteroaryl, 5- to 7-membered heteroaryl, and the like. Heteroaryl may be unsubstituted, or substituted as described for alkyl or as described in the various embodiments provided herein. Illustrative heteroaryl groups include, but are not limited to, pyrrolyl, furanyl, thiophenyl, imidazolyl, oxazolyl, thiazolyl, pyrazolyl, pyridinyl, pyrimidinyl, quinolinyl, isoquinolinyl, purinyl, tetrazolyl, triazinyl, pyrazinyl, tetrazinyl, quinazolinyl, quinoxalinyl, thienyl, isoxazolyl, isothiazolyl, oxadiazolyl, thiadiazolyl, triazolyl, benzimidazolyl, benzoxazolyl, benzthiazolyl, benzisoxazolyl, benzisothiazolyl and carbazoloyl, and the like. Illustrative examples of heteroaryl groups shown in graphical representations, include the following entities, in the form of properly bonded moieties:

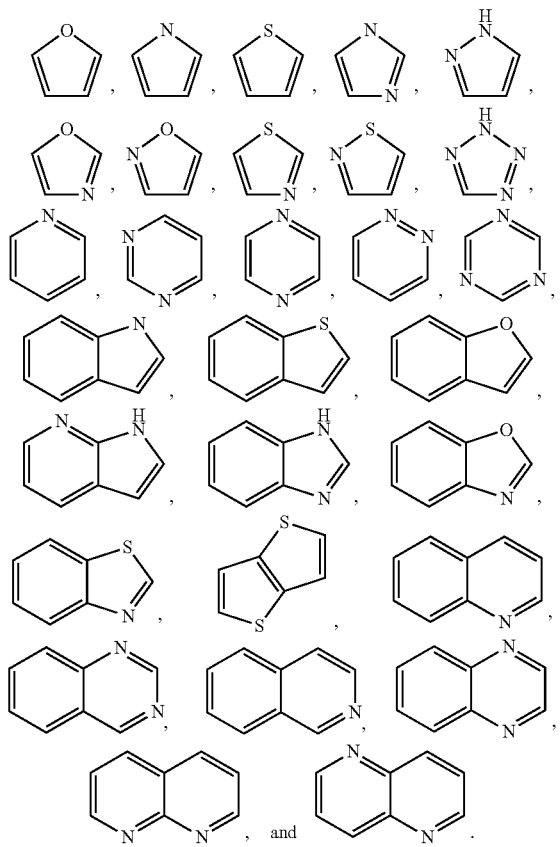

As used herein, "hydroxy" or "hydroxyl" refers to an —OH group.

As used herein, "alkoxy" refers to both an —O-(alkyl) or an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

As used herein, "aryloxy" refers to an —O-aryl or an —O-heteroaryl group. Representative examples include, but are not limited to, phenoxy, pyridinyloxy, furanyloxy, thienyloxy, pyrimidinyloxy, pyrazinyloxy, and the like, and the like.

As used herein, "mercapto" refers to an —SH group.

As used herein, "alkylthio" refers to an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

As used herein, "arylthio" refers to an —S-aryl or an —S-heteroaryl group. Representative examples include, but are not limited to, phenylthio, pyridinylthio, furanylthio, thienylthio, pyrimidinylthio, and the like.

As used herein, "halo" or "halogen" refers to fluorine, chlorine, bromine or iodine.

As used herein, "cyano" refers to a —CN group.

The term "oxo" represents a carbonyl oxygen. For example, a cyclopentyl substituted with oxo is cyclopentanone.

As used herein, "bond" refers to a covalent bond.

The term "substituted" means that the specified group or moiety bears one or more substituents. The term "unsubstituted" means that the specified group bears no substituents. Where the term "substituted" is used to describe a structural system, the substitution is meant to occur at any valency-allowed position on the system. In some embodiments, "substituted" means that the specified group or moiety bears one, two, or three substituents. In other embodiments, "substituted" means that the specified group or moiety bears one or two substituents. In still other embodiments, "substituted" means the specified group or moiety bears one substituent.

As used herein, "optional" or "optionally" means that the subsequently described event or circumstance may but need not occur, and that the description includes instances where the event or circumstance occurs and instances in which it does not. For example, "wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by $C_1$-$C_6$ alkyl" means that an alkyl may be but need not be present on any of the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$—$C_{10}$ aryl, or mono- or bicyclic heteroaryl by replacement of a hydrogen atom for each alkyl group, and the description includes situations where the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is substituted with an alkyl group and situations where the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is not substituted with the alkyl group.

As used herein, "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Or for example, where multiple groups exist all of which can be selected from a set of possibilities, the use of "independently" means that each of the groups can be selected from the set of possibilities separate from any other group, and the groups selected in the circumstance may be the same or different.

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof.

Representative Embodiments

In some embodiments, the present disclosure provides an XPA inhibitor compound of the formula

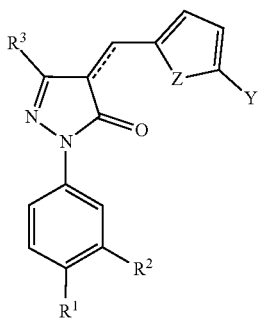

wherein
Z is O or S;
$R^1$ and $R^2$ are independently selected from the group consisting of H, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^6$, —CN, —$NO_2$, —C(O)$R^6$, —$CO_2R^6$, —C(O)$NR^6R^7$, —OS(O)$R^6$, —OS(O)$_2R^6$, —$SR^6$, —S(O)$R^6$, —S(O)$_2R^6$, —S(O)$NR^6R^7$, —S(O)$_2NR^6R^7$, —OS(O)$NR^6R^7$, —OS(O)$_2NR^6R^7$, and —$NR^6R^7$; wherein each hydrogen atom in $C_1$-$C_6$ alkyl, $C_2$-$C_6$ alkenyl, $C_2$-$C_6$ alkynyl or $C_3$-$C_6$ cycloalkyl is independently optionally substituted with halogen;
$R^3$ is H, halogen, or $C_1$-$C_6$ alkyl, wherein each hydrogen atom in $C_1$-$C_6$ alkyl, $C_2$-$C_6$ alkenyl, $C_2$-$C_6$ alkynyl or $C_3$-$C_6$ cycloalkyl is independently optionally substituted with halogen;
Y is —C(O)$NR^4R^5$ or phenyl, wherein each hydrogen atom in phenyl is optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^4$, —CN, —$NO_2$, —C(O)$R^4$, —$CO_2R^4$, —C(O)$NR^4R^5$, —OS(O)$R^4$, —OS(O)$_2R^4$, —$SR^4$, —S(O)$R^4$, —S(O)$_2R^4$, —S(O)$NR^4R^5$, —S(O)$_2NR^4R^5$, —OS(O)$NR^4R^5$, —OS(O)$_2NR^4R^5$, and —$NR^4R^5$, or two adjacent hydrogen atoms on phenyl are optionally substituted with a group that combines with the carbon atoms to which they are attached to form a 5- to 7-membered heterocycloalkyl ring;
$R^4$ and $R^5$ are each independently selected from the group consisting of H, $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl), —$C_1$-$C_6$ alkyl-($C_6$-$C_{10}$ aryl), 3- to 7-membered heterocycloalkyl, $C_6$-$C_{10}$ aryl and 5- to 7-membered heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl) or —$C_1$-$C_6$ alkyl-($C_6$-$C_{10}$ aryl) is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —C(O)$R^8$, —$CO_2R^8$, —C(O)$NR^8R^9$, —OS(O)$R^8$, —OS(O)$_2R^8$, —$SR^8$, —S(O)$R^8$, —S(O)$_2R^8$, —S(O)$NR^8R^9$, —S(O)$_2NR^8R^9$, —OS(O)$NR^8R^9$, —OS(O)$_2NR^8R^9$, and —$NR^8R^9$;
each $R^6$, $R^7$, $R^8$ and $R^9$ is independently selected from the group consisting of H, $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl), —$C_1$-$C_6$ alkyl-($C_6$-$C_{10}$ aryl), 3- to 7-membered heterocycloalkyl and $C_6$-$C_{10}$ aryl; $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl) or —$C_1$-$C_6$ alkyl-($C_6$-$C_{10}$ aryl) is independently optionally substituted with halogen, and
===== is either a single bond or a pi-bond.

In some embodiments, Y is —C(O)$NR^4R^5$ or phenyl. In some embodiments, phenyl is of the formula

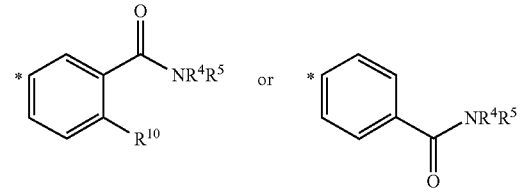

wherein $R^4$, $R^5$ and $R^{10}$ are as defined herein, and * represents a covalent bond to the compound of the formula II. In some embodiments, Y is —C(O)$NR^4R^5$ or phenyl, wherein each hydrogen atom in phenyl is optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^4$, —CN, —$NO_2$, —C(O)$R^4$, —$CO_2R^4$, —C(O)$NR^4R^5$, —OS(O)$R^4$, —OS(O)$_2R^4$, —$SR^4$, —S(O)$R^4$, —S(O)$_2R^4$, —S(O)$NR^4R^5$, —S(O)$_2NR^4R^5$, —OS(O)$NR^4R^5$, —OS(O)$_2NR^4R^5$, and —$NR^4R^5$, or two adjacent hydrogen atoms on phenyl are optionally substituted with a group that combines with the carbon atoms to which they are attached to form a 5- to 7-membered heterocycloalkyl ring. In some embodiments, Y is -C(O)$NR^4R^5$.

In some embodiments, the XPA inhibitor compounds described herein are of the formula Ia, Ia

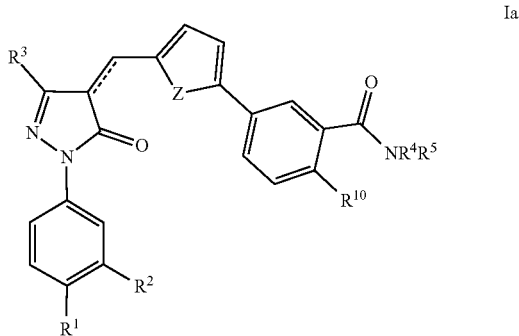

wherein each of Z, $R^1$, $R^2$, $R^3$, $R^4$, $R^5$ and $R^{10}$ are as defined herein.

In some embodiments, the XPA inhibitor compounds described herein are of the formula Ib

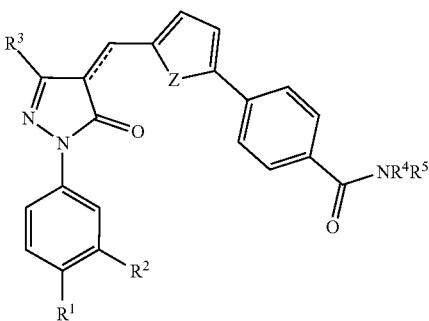

wherein each of Z, $R^1$, $R^2$, $R^3$, $R^4$ and $R^5$ are as defined herein.

In some embodiments, Z is O. In some embodiments, $R^4$ is $C_6$-$C_{10}$ aryl, wherein each hydrogen atom in $C_6$-$C_{10}$ aryl is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —C(O)$R^8$, —$CO_2R^8$, —C(O)NR$^8$R$^9$, —OS(O)R$^8$, —OS(O)$_2$R$^8$, —SR$^8$, —S(O)R$^8$, —S(O)$_2$R$^8$, —S(O)NR$^8$R$^9$, —S(O)$_2$NR$^8$R$^9$, —OS(O)NR$^8$R$^9$, —OS(O)$_2$NR$^8$R$^9$, and —NR$^8$R$^9$. In some embodiments, $R^4$ is $C_6$-$C_{10}$ aryl, substituted with one substituent selected from the group consisting of halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —OR$^8$, —CN, —NO$_2$, —C(O)R$^8$, —CO$_2$R$^8$, —C(O)NR$^8$R$^9$, —OS(O)R$^8$, —OS(O)$_2$R$^8$, —SR$^8$, —S(O)R$^8$, —S(O)$_2$R$^8$, —S(O)NR$^8$R$^9$, —S(O)$_2$NR$^8$R$^9$, —OS(O)NR$^8$R$^9$, —OS(O)$_2$NR$^8$R$^9$, and —NR$^8$R$^9$. In some embodiments, the one substituent is in the para-position. In some embodiments, the one substituent is in the meta-position. In some embodiments, $R^4$ is $C_6$-$C_{10}$ aryl, substituted with two substituents independently selected from the group consisting of halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —OR$^8$, —CN, —NO$_2$, —C(O)R$^8$, —CO$_2$R$^8$, —C(O)NR$^8$R$^9$, —OS(O)R$^8$, —OS(O)$_2$R$^8$, —SR$^8$, —S(O)R$^8$, —S(O)$_2$R$^8$, —S(O)NR$^8$R$^9$, —S(O)$_2$NR$^8$R$^9$, —OS(O)NR$^8$R$^9$, —OS(O)$_2$NR$^8$R$^9$, and —NR$^8$R$^9$.

In some embodiments, $R^4$ is $C_6$-$C_{10}$ aryl, wherein $C_6$-$C_{10}$ aryl is substituted with at least one halogen, or —OR$^8$. In some embodiments, $R^4$ is phenyl, wherein each hydrogen atom in phenyl is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —OR$^8$, —CN, —NO$_2$, —C(O)R$^8$, —CO$_2$R$^8$, —C(O)NR$^8$R$^9$, —OS(O)R$^8$, —OS(O)$_2$R$^8$, —SR$^8$, —S(O)R$^8$, —S(O)$_2$R$^8$, —S(O)NR$^8$R$^9$, —S(O)$_2$NR$^8$R$^9$, —OS(O)NR$^8$R$^9$, —OS(O)$_2$NR$^8$R$^9$, or —NR$^8$R$^9$. In some embodiments, $R^4$ is phenyl, substituted with on substituent selected from the groups consisting of halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —OR$^8$, —CN, —NO$_2$, —C(O)R$^8$, —CO$_2$R$^8$, —C(O)NR$^8$R$^9$, —OS(O)R$^8$, —OS(O)$_2$R$^8$, —SR$^8$, —S(O)R$^8$, —S(O)$_2$R$^8$, —S(O)NR$^8$R$^9$, —S(O)$_2$NR$^8$R$^9$, —OS(O)NR$^8$R$^9$, —OS(O)$_2$NR$^8$R$^9$, and —NR$^8$R$^9$. In some embodiments, the one substituent is in the para-position. In some embodiments, the one substituent is in the meta-position. In some embodiments, $R^4$ is phenyl, substituted with two substituents independently selected from the group consisting of halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —OR$^8$, —CN, —NO$_2$, —C(O)R$^8$, —CO$_2$R$^8$, —C(O)NR$^8$R$^9$, —OS(O)R$^8$, —OS(O)$_2$R$^8$, —SR$^8$, —S(O)R$^8$, —S(O)$_2$R$^8$, —S(O)NR$^8$R$^9$, —S(O)$_2$NR$^8$R$^9$, —OS(O)NR$^8$R$^9$, —OS(O)$_2$NR$^8$R$^9$, and —NR$^8$R$^9$.

In some embodiments, $R^4$ is phenyl substituted with at least one halogen, or —OR$^8$.

In some embodiments, $R^4$ is —$C_1$-$C_6$ alkyl-($C_3$-$C_6$ cycloalkyl). In some embodiments, $R^4$ is —$C_1$-$C_6$ alkyl-($C_6$-$C_{10}$ aryl), and each hydrogen atom in $C_6$-$C_{10}$ aryl is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —OR$^8$, —CN, —NO$_2$, —C(O)R$^8$, —CO$_2$R$^8$, —C(O)NR$^8$R$^9$, —OS(O)R$^8$, —OS(O)$_2$R$^8$, —SR$^8$, —S(O)R$^8$, —S(O)$_2$R$^8$, —S(O)NR$^8$R$^9$, —S(O)$_2$NR$^8$R$^9$, —OS(O)NR$^8$R$^9$, —OS(O)$_2$NR$^8$R$^9$, or —NR$^8$R$^9$. In some embodiments, $R^4$ is —$C_1$-$C_6$ alkyl-($C_6$-$C_{10}$ aryl), substituted one substituent selected from the groups consisting of halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —OR$^8$, —CN, —NO$_2$, —C(O)R$^8$, —CO$_2$R$^8$, —C(O)NR$^8$R$^9$, —OS(O)R$^8$, —OS(O)$_2$R$^8$, —SR$^8$, —S(O)R$^8$, —S(O)$_2$R$^8$, —S(O)NR$^8$R$^9$, —S(O)$_2$NR$^8$R$^9$, —OS(O)NR$^8$R$^9$, —OS(O)$_2$NR$^8$R$^9$, and —NR$^8$R$^9$. In some embodiments, the one substituent is in the para-position. In some embodiments, the one substituent is in the meta-position. In some embodiments, $R^4$ is —$C_1$-$C_6$ alkyl-($C_6$-$C_{10}$ aryl), substituted two substituents independently selected from the groups consisting of halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —OR$^8$, —CN, —NO$_2$, —C(O)R$^8$, —CO$_2$R$^8$, —C(O)NR$^8$R$^9$, —OS(O)R$^8$, —OS(O)$_2$R$^8$, —SR$^8$, —S(O)R$^8$, —S(O)$_2$R$^8$, —S(O)NR$^8$R$^9$, —S(O)$_2$NR$^8$R$^9$, —OS(O)NR$^8$R$^9$, —OS(O)$_2$NR$^8$R$^9$, and —NR$^8$R$^9$.

In some embodiments, $R^4$ is —$C_1$-$C_6$ alkyl-($C_6$-$C_{10}$ aryl), wherein $C_6$-$C_{10}$ aryl is substituted with at least one halogen, or —OR$^8$.

In some embodiments, $R^4$ is benzyl, wherein each hydrogen atom in benzyl is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —OR$^8$, —CN, —NO$_2$, —C(O)R$^8$, —CO$_2$R$^8$, —C(O)NR$^8$R$^9$, —OS(O)R$^8$, —OS(O)$_2$R$^8$, —SR$^8$, —S(O)R$^8$, —S(O)$_2$R$^8$, —S(O)NR$^8$R$^9$, —S(O)$_2$NR$^8$R$^9$, —OS(O)NR$^8$R$^9$, —OS(O)$_2$NR$^8$R$^9$, and —NR$^8$R$^9$. In some embodiments, $R^4$ is benzyl, substituted with one substituent selected from the group consisting of halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —OR$^8$, —CN, —NO$_2$, —C(O)R$^8$, —CO$_2$R$^8$, —C(O)NR$^8$R$^9$, —OS(O)R$^8$, —OS(O)$_2$R$^8$, —SR$^8$, —S(O)R$^8$, —S(O)$_2$R$^8$, —S(O)NR$^8$R$^9$, —S(O)$_2$NR$^8$R$^9$, —OS(O)NR$^8$R$^9$, —OS(O)$_2$NR$^8$R$^9$, and —NR$^8$R$^9$. In some embodiments, the one substituent is in the para-position. In some embodiments, the one substituent is in the meta-position. In some embodiments, $R^4$ is benzyl, substituted with two substituents independently selected from the group consisting of halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —OR$^8$, —CN, —NO$_2$, —C(O)R$^8$, —CO$_2$R$^8$, —C(O)NR$^8$R$^9$, —OS(O)R$^8$, —OS(O)$_2$R$^8$, —SR$^8$, —S(O)R$^8$, —S(O)$_2$R$^8$, —S(O)NR$^8$R$^9$, —S(O)$_2$NR$^8$R$^9$, —OS(O)NR$^8$R$^9$, —OS(O)$_2$NR$^8$R$^9$, and —NR$^8$R$^9$.

In some embodiments, R⁴ is benzyl substituted with at least one halogen, or —OR⁸.

In some embodiments, R⁴ selected from the group consisting of

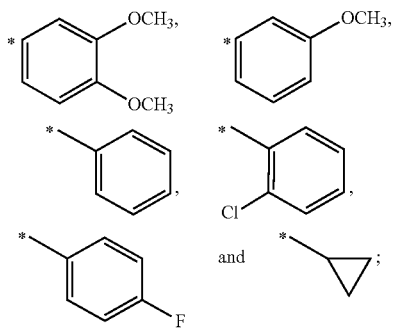

wherein * represent the point of attachment of R⁴.

In some embodiments, R⁵ is H. In some embodiments, R³ is $C_1$-$C_6$ alkyl. In some embodiments, R³ is methyl. In some embodiments, R¹ and R² are each independently H, 5- to 7-membered heteroaryl, —CN, —CO₂R⁶ or —S(O)₂NR⁶R⁷, provided that at least one of R¹ and R² is not H. In some embodiments, R¹ is H and R² is 5- to 7-membered heteroaryl, —CN or —CO₂R⁶. In some embodiments, R¹ is —CO₂R⁶, and R² is H. In some embodiments, R² is —CO₂R⁶, and R⁶ is H. In some embodiments, R² is —CO₂R⁶, and R⁶ is ethyl. In some embodiments, R¹ is —CO₂R⁶, and R⁶ is H. In some embodiments, R¹ is —CO₂R⁶, and R⁶ is ethyl. In some embodiments, R¹⁰ is chloro. In some embodiments, ===== is a single bond. In some embodiments, ===== is a pi-bond.

Pharmaceutical Compositions

For treatment purposes, pharmaceutical compositions comprising the compounds described herein may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the description are sterile compositions. Pharmaceutical compositions may be prepared using compounding techniques known or that become available to those skilled in the art.

Sterile compositions are also contemplated by the description, including compositions that are in accord with national and local regulations governing such compositions.

The pharmaceutical compositions and compounds described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the description may be administered by a suitable route of delivery, such as oral, parenteral, rectal, nasal, topical, or ocular routes, or by inhalation. Preferably, the compositions are formulated for intravenous or oral administration.

For oral administration, the compounds the description may be provided in a solid form, such as a tablet or capsule, or as a solution, emulsion, or suspension. To prepare the oral compositions, the compounds of the description may be formulated to yield a dosage of, e.g., from about 0.1 mg to 1 g daily, or about 1 mg to 50 mg daily, or about 50 to 250 mg daily, or about 250 mg to 1 g daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

For parenteral use, including intravenous, intramuscular, intraperitoneal, intranasal, or subcutaneous routes, the agents of the description may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 μg/kg/minute of agent admixed with a pharmaceutical carrier over a period ranging from several minutes to several days.

For nasal, inhaled, or oral administration, the inventive pharmaceutical compositions may be administered using, for example, a spray formulation also containing a suitable carrier. The inventive compositions may be formulated for rectal administration as a suppository.

For topical applications, the compounds of the present description are preferably formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the description may utilize a patch formulation to affect transdermal delivery.

Methods of Treatment

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying systemic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

The term "subject" refers to a mammalian patient in need of such treatment, such as a human. As used herein "cancer" includes any cancer known in the art, particularly those cancers where platinum drug treatments are useful. Examples of cancer types include, but are not limited to, carcinomas, sarcomas, lymphomas, Hodgekin's disease, melanomas, mesotheliomas, Burkitt's lymphoma, nasopharyngeal carcinomas, leukemias, and myelomas. Examples of specific cancers include, but are not limited to, oral cancer, thyroid cancer, endocrine cancer, skin cancer, gastric cancer, esophageal cancer, laryngeal cancer, pancreatic cancer, colon cancer, bladder cancer, bone cancer, ovarian cancer, cervical cancer, uterine cancer, breast cancer, testicular cancer, prostate cancer, renal cancer, rectal cancer, kidney cancer, liver cancer, glioblastoma, or head & neck cancer, and lung cancers, such as non-small cell lung cancer, small cell lung cancer, and the like.

In some embodiments, the disclosure is directed to an XPA inhibitor compound as described herein, or a pharmaceutically acceptable salt thereof, for use in the treatment of cancer in a patient. In some embodiments, the XPA inhibitor compound is of the Formula I, Ia, Ib or II.

In some embodiments, the disclosure is directed to use of an XPA inhibitor compound as described herein, or a pharmaceutically acceptable salt thereof, for use in the treatment of cancer in a patient. In some embodiments, the compound the XPA inhibitor compound is of the Formula I, Ia, Ib or II.

In some embodiments, the disclosure is directed to use of an XPA inhibitor compound as described herein, or a pharmaceutically acceptable salt thereof, in the preparation of a medicament for the treatment of cancer in a patient. In some embodiments, the XPA inhibitor compound the compound is of the Formula I, Ia, Ib or II.

In some embodiments, the disclosure is directed to a composition comprising an XPA inhibitor compound as described herein, or a pharmaceutically acceptable salt thereof, in a therapeutically effective amount, for use in the treatment of cancer in a patient. In some embodiments, the XPA inhibitor compound the compound is of the Formula I, Ia, Ib or II.

In the inhibitory methods of the description, an "effective amount" means an amount sufficient to inhibit the target. Measuring such target modulation may be performed by routine analytical methods such as those described below. Such modulation is useful in a variety of settings, including in vitro assays.

In treatment methods according to the description, an "effective amount" means an amount or dose sufficient to generally bring about the desired therapeutic benefit in subjects needing such treatment. Effective amounts or doses of the compounds of the description may be ascertained by routine methods, such as modeling, dose escalation, or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose is in the range of about from about 0.1 mg to 1 g daily, or about 1 mg to 50 mg daily, or about 50 to 250 mg daily, or about 250 mg to 1 g daily. The total dosage may be given in single or divided dosage units (e.g., BID, TID, QID).

Once improvement of the patient's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

Drug Combinations

The inventive compounds described herein may be used in pharmaceutical compositions or methods in combination with one or more additional cancer therapies. Further additional cancer therapies include other therapeutics or agents that mitigate adverse effects of therapies for the intended disease targets. Such combinations may serve to increase efficacy, ameliorate other disease symptoms, decrease one or more side effects, or decrease the required dose of an inventive compound. The additional cancer therapy may be administered in a separate pharmaceutical composition from a compound of the present description or may be included with a compound of the present description in a single pharmaceutical composition. The additional active ingredients may be administered simultaneously with, prior to, or after administration of a compound of the present description.

Combination agents include additional active ingredients are those that are known or discovered to be effective in treating the diseases and disorders described herein, including those active against another target associated with the disease. For example, compositions and formulations of the description, as well as methods of treatment, can further comprise other drugs or pharmaceuticals, e.g., other active agents useful for treating or palliative for the target diseases or related symptoms or conditions. Such additional agents include, but are not limited to, kinase inhibitors, such as EGFR inhibitors (e.g., erlotinib, gefitinib), Raf inhibitors (e.g., vemurafenib), VEGFR inhibitors (e.g., sunitinib), ALK inhibitors (e.g., crizotinib) standard chemotherapy agents such as alkylating agents, antimetabolites, anti-tumor antibiotics, topoisomerase inhibitors, platinum drugs, mitotic inhibitors, antibodies, hormone therapies, or corticosteroids. For pain indications, suitable combination agents include anti-inflammatories such as NSAIDs. The pharmaceutical compositions of the description may additional comprise one or more of such active agents, and methods of treatment may additionally comprise administering an effective amount of one or more of such active agents.

In some embodiments, the disclosure is directed to a method of treating cancer in a patient comprising, a. administering a therapeutically effective amount of an XPA inhibitor compound as described herein; and b. administering a therapeutically effective amount of at least one additional cancer therapy. In some embodiments, the at least one additional cancer therapy is a platinum drug. In some embodiments, the additional cancer therapy is selected from the group consisting of cisplatin, carboplatin, oxaliplatin, nedaplatin, triplatin tetranitrate, phenanthriplatin, picoplatin, and satraplatin.

In some embodiments, the disclosure is directed to an XPA inhibitor compound as described herein, or a pharmaceutically acceptable salt thereof, in combination with a therapeutically effective amount of at least one additional cancer therapy, or a pharmaceutically acceptable salt thereof, for use in the treatment of cancer in a patient. In some embodiments, the at least one additional cancer therapy is a platinum drug. In some embodiments, the additional cancer therapy is selected from the group consisting of cisplatin, carboplatin, oxaliplatin, nedaplatin, triplatin tetranitrate, phenanthriplatin, picoplatin, and satraplatin.

In some embodiments, the disclosure is directed to use of an XPA inhibitor compound as described herein, or a pharmaceutically acceptable salt thereof, in combination with a therapeutically effective amount of at least one additional cancer therapy for the treatment of cancer in a patient. In some embodiments, the at least one additional cancer therapy is a platinum drug. In some embodiments, the additional cancer therapy is selected from the group consisting of cisplatin, carboplatin, oxaliplatin, nedaplatin, triplatin tetranitrate, phenanthriplatin, picoplatin, and satraplatin.

In some embodiments, the disclosure is directed to use of an XPA inhibitor compound as described herein, or a pharmaceutically acceptable salt thereof, in the preparation of a medicament for the treatment of cancer in a patient in combination with a therapeutically effective amount of at least one additional cancer therapy. In some embodiments, the at least one additional cancer therapy is a platinum drug. In some embodiments, the additional cancer therapy is selected from the group consisting of cisplatin, carboplatin, oxaliplatin, nedaplatin, triplatin tetranitrate, phenanthriplatin, picoplatin, and satraplatin.

In some embodiments, the disclosure is directed to a composition comprising an XPA inhibitor compound as described herein, or a pharmaceutically acceptable salt thereof, in a therapeutically effective amount, for use in the treatment of cancer in a patient. In some embodiments, the at least one additional cancer therapy is a platinum drug. In some embodiments, the additional cancer therapy is selected from the group consisting of cisplatin, carboplatin, oxaliplatin, nedaplatin, triplatin tetranitrate, phenanthriplatin, picoplatin, and satraplatin.

In some embodiments, the disclosure relates to a synergistic composition of an XPA inhibitor compound as described herein, and an addition cancer therapy, where the two components come into contact with each other at a locus. In some embodiments, the at least one additional cancer therapy is a platinum drug. In some embodiments, the additional cancer therapy is selected from the group consisting of cisplatin, carboplatin, oxaliplatin, nedaplatin, triplatin tetranitrate, phenanthriplatin, picoplatin, and satraplatin.

EXAMPLES

Example 1

Chemical Synthesis

All chemicals used for synthesis were purchased from Aldrich, Alfa Aesar, Acros, Fisher Scientific, AK Scientific and Combi-Blocks Chemical Co. (USA) and used without further purification. Anhydrous solvents were obtained from Fisher Scientific or Aldrich and used directly. All reactions involving air- or moisture-sensitive reagents were performed under a nitrogen atmosphere. $^1$H NMR spectra were recorded at 300 MHz and 500 MHz using Bruker AV NMR spectrometer. $^{13}$C NMR spectra were recorded at 75 MHz and 125 MHz using Bruker AV NMR spectrometer. The chemical shifts were reported as δ ppm relative to TMS, using the residual solvent peak as the reference unless otherwise noted. All coupling constants (J) are given in Hertz. Data are reported as follows: chemical shift, multiplicity (s=singlet, d=doublet, t=triplet, q=quartet, br=broad, m=multiplet), number of protons and coupling constants. Thin layer chromatography was performed using Merck silica gel 60 F-254 thin layer plates, which were developed using one of the following techniques: UV fluorescence (254 nm), alkaline potassium permanganate solution (0.5% w/v) or ninhydrin (0.2% w/v) and Iodine vapors. Automated flash column chromatography was carried out on prepacked silica cartridges using the indicated solvent system on Biotage Isolera chromatography system. Target compounds 33a, 34a-k and 39a-d were crystallized in ethanol, solid was collected, washed with EtOAc and then hot solutions of 20-30% EtOAc in hexanes to afford red to orange solids. If necessary, the products were purified with automated flash column chromatography. The chemical purity of target compounds was ≥95% determined by HPLC coupled to electrospray ionization mass spectrometry (LC/ESI-MS) analysis. LC-MS analyses and compounds purity data were obtained using an Agilent 6130 Quadrupole LC-MS connected to an Agilent 1200 HPLC system and both instruments were connected to an Agilent diode array detector. A C-18 reversed phase column (Vydac monomeric/Phenomenex/Kinetex 2.6 μM XB—C18, 50×4.6 mm) was used as stationary phase, water and methanol/acetonitrile (both containing 0.1 to 0.25% TFA) was used as mobile phase (gradient: 0-100% methanol, flow 0.8 mL/min, run time 15 min), and UV absorbance at the fixed wavelength of 254 nm and positive and negative ESI-MS data were recorded. The retention time and corresponding ESI-MS data were used as identity of molecules. HRMS data were obtained using Waters/Macromass LCT electrospray ionization (ESI) on a time of flight (TOF) mass spectrometer at the Mass Spectrometry Facility at Indiana University Chemistry Department (http://msf.chem.indiana.edu).

Figure 2A:
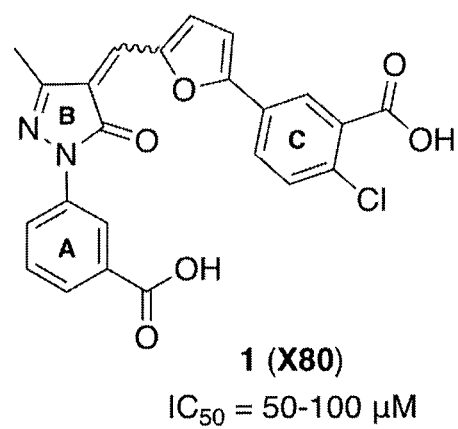
FIG. 2A shows the structure of compound 1 (X80).

Compound X80 (1) (FIG. 2A) and its commercially available analogs 2-24 were purchased from ChemDiv (San Diego, USA) and AKos GmbH (Steinen, Germany) library with highest purity (≥95%) and prepared at 10 mM stock solution in 100% DMSO Scheme 1. Synthesis of Analogs 34a-k[a]

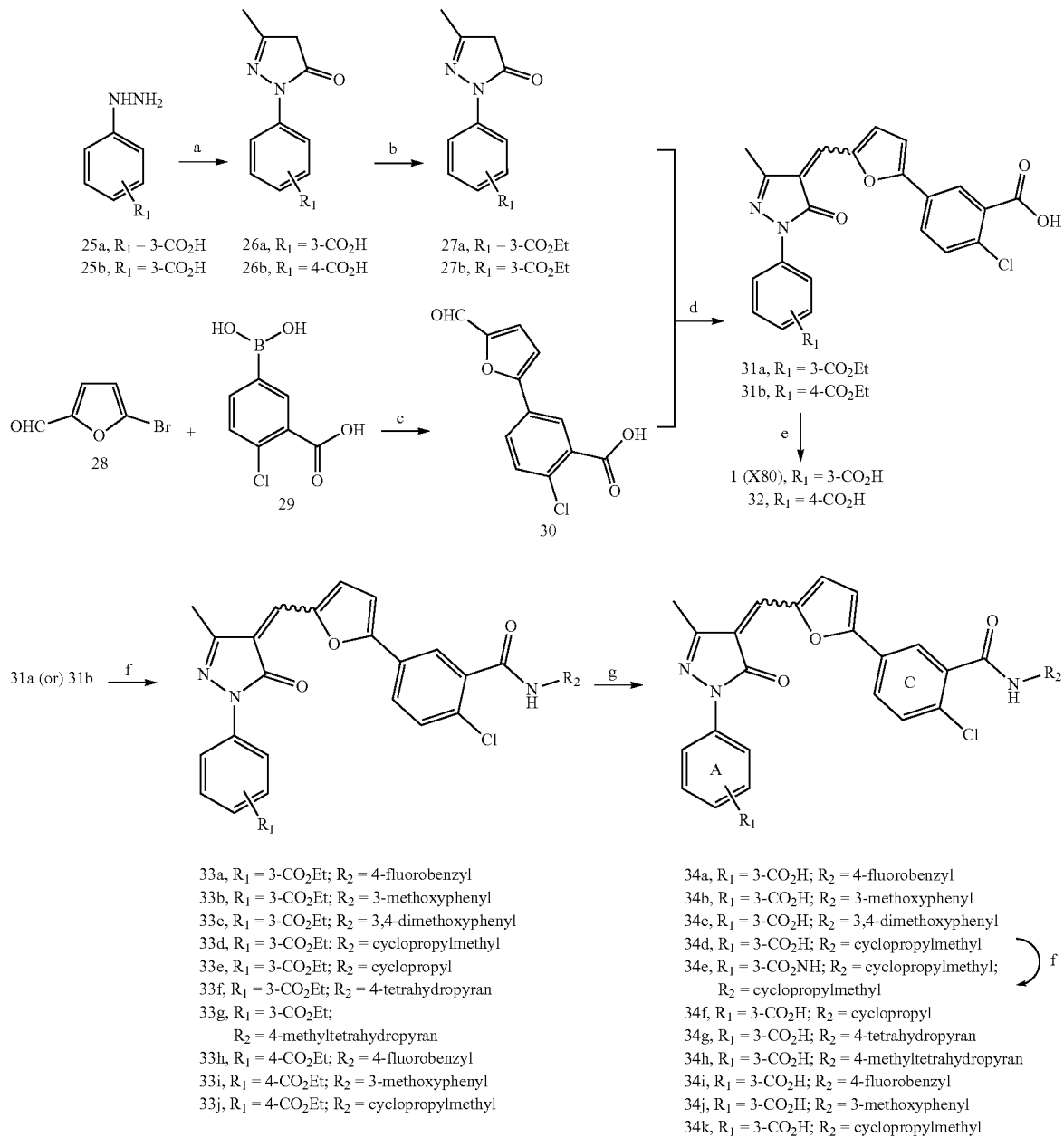

33a, R₁ = 3-CO₂Et; R₂ = 4-fluorobenzyl
33b, R₁ = 3-CO₂Et; R₂ = 3-methoxyphenyl
33c, R₁ = 3-CO₂Et; R₂ = 3,4-dimethoxyphenyl
33d, R₁ = 3-CO₂Et; R₂ = cyclopropylmethyl
33e, R₁ = 3-CO₂Et; R₂ = cyclopropyl
33f, R₁ = 3-CO₂Et; R₂ = 4-tetrahydropyran
33g, R₁ = 3-CO₂Et;
R₂ = 4-methyltetrahydropyran
33h, R₁ = 4-CO₂Et; R₂ = 4-fluorobenzyl
33i, R₁ = 4-CO₂Et; R₂ = 3-methoxyphenyl
33j, R₁ = 4-CO₂Et; R₂ = cyclopropylmethyl 34a, R₁ = 3-CO₂H; R₂ = 4-fluorobenzyl
34b, R₁ = 3-CO₂H; R₂ = 3-methoxyphenyl
34c, R₁ = 3-CO₂H; R₂ = 3,4-dimethoxyphenyl
34d, R₁ = 3-CO₂H; R₂ = cyclopropylmethyl
34e, R₁ = 3-CO₂NH; R₂ = cyclopropylmethyl;
R₂ = cyclopropylmethyl
34f, R₁ = 3-CO₂H; R₂ = cyclopropyl
34g, R₁ = 3-CO₂H; R₂ = 4-tetrahydropyran
34h, R₁ = 3-CO₂H; R₂ = 4-methyltetrahydropyran
34i, R₁ = 3-CO₂H; R₂ = 4-fluorobenzyl
34j, R₁ = 3-CO₂H; R₂ = 3-methoxyphenyl
34k, R₁ = 3-CO₂H; R₂ = cyclopropylmethyl

[a]Reagents and conditions: (a) ethyl acetoacetate, AcOH, reflux for 12 h, 72-76%; (b) H₂SO₄, EtOH, reflux for 12 h, 77-80%; (c) Pd(PPh₃)₄, K₂CO₃, toluene:EtOH:H₂O (1:1:0.3), 90° C. for 15 h, 92%; (d) AcOH, reflux for 3 h, 76-87%; (e) 2N NaOH, THF:MeOH (2:1), rt for 6 h, 82-85%; (f) alkyl or aryl amine, EDCI, HOBt, DIPEA, DMF, rt for 18 h, 62-81%; (g) LiOH, THF:EtOH:H₂O (4:2:1), rt for 12 h, 60-76% (after recrystallization).

Synthesis of 26a and 26b. 3-(3-Methyl-5-oxo-4,5-dihydro-1H-pyrazol-1-yl)benzoic acid (26a)

Ethyl acetoacetate (2.01 mL, 1.2 equiv.) was added to a solution of 3-hydrazinobenzoic acid 25a (2 gm, 1 equiv.) in glacial acetic acid (30 mL) under an argon atmosphere. After addition, the reaction mixture was heated at reflux with stirring for 12 h. Once the reaction was allowed to cool to room temperature, the reaction mixture was concentrated in vacuo resulting in the formation of a precipitate. The solid was filtered and washed with 5% MeOH in DCM (2 times) and then two times with DCM to obtain 26a as an off-white solid (2.06 gm, 72% yield, require no further purification). TLC: 4% MeOH in DCM, $R_f$=0.42; visualized with UV. $^1$H NMR (500 MHz, DMSO): δ 13.22 (brs, 1H, COOH), 8.36 (s, 1H), 8.05 (d, 1H, J=8.5 Hz), 7.94 (d, 1H, J=8.0 Hz), 7.70 (t, 1H, J=8.0 and 16 Hz), 5.97 (s, 1H), 2.45 (s, 3H, CH₃); $^{13}$C NMR (125 MHz, DMSO): δ 166.48, 158.79, 154.09, 150.10, 144.90, 136.81, 132.15, 129.96, 127.57, 124.16, 120.66, 104.64, 102.19, 19.12, 14.25. HRMS (ESI): calcd for $C_{11}H_{11}N_2O_3$ [M+H]⁺ m/z=219.0770, found 219.0764.

4-(3-Methyl-5-oxo-4,5-dihydro-1H-pyrazol-1-yl) benzoic acid (26b)

26b was prepared by an above described procedure using 4-hydrazinobenzoic acid hydrochloride 25b (2 gm) as a starting material. Off-white solid, (1.76 gm, 76% yield, require no further purification). TLC: 4% MeOH in DCM, $R_f$=0.42; visualized with UV. $^1$H NMR (300 MHz, DMSO): δ 12.87 (brs, 1H, COOH), 7.98 (d, 2H, J=8.8 Hz), 7.88 (d, 2H, J=8.4 Hz), 5.38 (s, 1H), 2.12 (s, 3H, CH$_3$). $^{13}$C NMR (125 MHz, DMSO): δ 172.17, 170.56, 167.32, 159.86, 150.25, 142.66, 142.06, 130.80, 126.86, 126.46, 119.33, 117.49, 117.34, 43.61, 14.45. HRMS (ESI): calcd for C$_{11}$H$_9$N$_2$O$_3$ [M−H]$^-$ m/z=217.0613, found 217.0619.

Synthesis of 27a and 27b. Ethyl 3-(3-methyl-5-oxo-4,5-dihydro-1H-pyrazol-1-yl)benzoate (27a)

To a stirred suspension of 3-(3-methyl-5-oxo-4,5-dihydro-1H-pyrazol-1-yl)benzoic acid 26a (1.95 gm) in anhydrous ethanol (30 mL) was added a catalytic amount of concentrated sulfuric acid (1.5 mL) slowly under an argon atmosphere. The reaction mixture was refluxed for 12 h and then it was allowed to cool to room temperature. The solvent was removed under vacuum, the obtained residue was dissolved in ethyl acetate and washed successively with saturated NaHCO$_3$ (2×10 mL), water and brine solution. The organic layer was dried over Na$_2$SO$_4$ and concentrated under reduced pressure. The crude residue was purified by Biotage automated flash column chromatography using 0 to 50% EtOAc in hexanes as the eluent to furnish ethyl 3-(3-methyl-5-oxo-4,5-dihydro-1H-pyrazol-1-yl)benzoate 27a as a red oil (1.69 gm, 77% yield). TLC: 45% EtOAc in hexanes, $R_f$=0.44; visualized with UV. $^1$H NMR (300 MHz, CDCl$_3$): δ 8.41 (s, 1H), 8.05 (d, 1H, J=8.2 Hz), 7.78 (d, 1H, J=8.0 Hz), 7.38 (t, 1H, J=7.95 and 15.99 Hz), 4.35-4.28 (q, 2H, OCH$_2$), 3.37 (s, 2H, CH$_2$), 2.11 (s, 3H, CH$_3$), 1.33 (t, 3H, J=7.11 and 14.25 Hz, CH$_3$); $^{13}$C NMR (75 MHz, CDCl$_3$): δ 170.70, 166.14, 156.84, 138.18, 131.22, 128.82, 125.77, 122.69, 119.46, 61.10, 43.02, 16.93, 14.29. MS (ESI) m/z=247.1 [M+H]$^+$.

Ethyl 4-(3-methyl-5-oxo-4,5-dihydro-1H-pyrazol-1-yl)benzoate (27b)

27b was prepared by an above described procedure using 26b (1.60 gm) as a starting material. White solid, (1.44 gm, 80% yield). TLC: 40% EtOAc in hexanes, $R_f$=0.44; visualized with UV. $^1$H NMR (300 MHz, CDCl$_3$): δ 8.05 (d, 2H, J=8.97 Hz), 8.01 (d, 2H, J=8.94 Hz), 4.40-4.33 (q, 2H, OCH$_2$), 3.46 (s, 2H, CH$_2$), 2.22 (s, 3H, CH$_3$), 1.39 (t, 3H, J=7.11 and 14.25 Hz, CH$_3$); $^{13}$C NMR (75 MHz, CDCl$_3$): δ 170.78, 166.18, 156.89, 141.69, 130.54, 126.42, 117.61, 60.90, 43.17, 17.09, 14.36. MS (ESI) m/z=247.1 [M+H]$^+$.

Synthesis of 2-Chloro-5-(5-formylfuran-2-yl)benzoic acid (30)

A solution of K$_2$CO$_3$ (2.37 gm, 3 equiv.) in water (10 mL) was added to a mixture of 4-chloro-3-carboxyphenylboronic acid 29 (1.37 gm, 1.2 equiv.) and 5-bromo-2-furaldehyde 28 (1 gm, 1 equiv.) in toluene:ethanol (1:1, v/v, 60 mL). The mixture was degassed with argon for 5 minute and then Pd(PPh$_3$)$_4$ (330 mg, 0.05 equiv.) was added. The reaction mixture was stirred at 90° C. for 15 h. The reaction mixture was cooled to room temperature, filtered through Celite and washed with water (2×10 mL). The pH of the solution was adjusted to 1-2 by addition of 6N HCl solution. The precipitated reaction mixture was extracted with dichloromethane (3×100 mL); the combined organic fractions were washed with brine, dried over anhydrous Na$_2$SO$_4$, and concentrated under reduced pressure. The crude product was triturated with 20-30% EtOAc in hexanes (2 times), solid was filtered to afford 2-chloro-5-(5-formylfuran-2-yl)benzoic acid 30 (1.24 gm, 87% yield) as an off-white solid. TLC: 60% EtOAc in hexanes, $R_f$=0.40; visualized with UV and KMnO$_4$ solution. $^1$H NMR (300 MHz, DMSO): δ 13.74 (brs, 1H, COOH), 9.63 (s, 1H, CHO), 8.23 (d, 1H, J=2.22 Hz), 8.01 (dd, 1H, J=2.28 and 8.43 Hz), 7.70 (d, 1H, J=8.34 Hz), 7.67 (d, 1H, J=2.85 Hz), 7.45 (d, 1H, J=3.75 Hz); $^{13}$C NMR (75 MHz, DMSO): δ 178.64, 166.63, 156.44, 152.47, 132.93, 132.78, 132.13, 129.00, 128.10, 127.23, 110.56. MS (ESI) m/z=249.0 [M−H]$^-$.

Synthesis of 31a and 31b. (Z)-2-Chloro-5-(5-((1-(3-(ethoxycarbonyl)phenyl)-3-methyl-5-oxo-1H-pyrazol-4(5H)-ylidene)methyl)furan-2-yl)benzoic acid (31a)

Ethyl 3-(3-methyl-5-oxo-4,5-dihydro-1H-pyrazol-1-yl) benzoate 27a (1 gm, 1 equiv.) and 2-chloro-5-(5-formylfuran-2-yl)benzoic acid 30 (1.01 gm, 1 equiv.) were dissolved in glacial acetic acid (50 mL). The reaction mixture was heated at reflux with stirring for 3 h. Solvent was removed in vacuo, solid was suspended in EtOH, filtered, washed with EtOH, EtOAc and DCM (2 times each) to obtain 31a as a red solid (1.48 gm, 76% yield, require no further purification). TLC: 5% MeOH in DCM, $R_f$=0.45; visualized with UV. Major Z-isomer data: $^1$H NMR (300 MHz, DMSO): δ 13.75 (brs, 1H, COOH), 8.63 (d, 1H, J=3.87 Hz), 8.48 (t, 1H, J=1.86 and 3.69 Hz), 8.27 (d, 1H, J=2.22 Hz), 8.19 (d, 1H, J=7.08 Hz), 8.01 (dd, 1H, J=2.22 and 8.43 Hz), 7.76-7.64 (m, 3H), 7.56-7.51 (m, 2H), 4.36-4.29 (q, 2H, OCH$_2$), 2.64 (s, 0.29H, minor isomer, CH$_3$), 2.32 (s, 2.71H, major isomer, CH$_3$), 1.33 (t, 3H, J=7.08 and 14.16 Hz, CH$_3$); $^{13}$C NMR (75 MHz, DMSO): δ 166.59, 165.88, 162.11, 157.65, 151.64, 150.82, 138.96, 133.15, 132.67, 131.11, 130.91, 130.08, 129.77, 128.96, 127.84, 127.26, 125.17, 122.41, 121.60, 118.43, 112.91, 61.38, 14.65, 13.29. MS (ESI) m/z=477.1 [M−H]$^-$.

(Z)-2-Chloro-5-(5-((1-(4-(ethoxycarbonyl)phenyl)-3-methyl-5-oxo-1H-pyrazol-4(5H)-ylidene)methyl) furan-2-yl)benzoic acid (31b)

31b was prepared by an above described procedure using 27b (1 gm, 1 equiv.) and 30 (1.01 gm, 1 equiv.) as starting materials. Red solid, (1.69 gm, 87% yield). TLC: 5% MeOH in DCM, $R_f$=0.48; visualized with UV. Major Z-isomer data: $^1$H NMR (300 MHz, DMSO): δ 13.72 (brs, 1H, COOH), 8.62 (d, 1H, J=3.84 Hz), 8.33 (d, 1H, J=2.19 Hz), 8.15-7.90 (m, 5H), 7.79 (s, 1H), 7.71 (d, 1H, J=8.49 Hz), 7.58 (d, 1H, J=3.84 Hz), 4.33-4.26 (q, 2H, OCH$_2$), 2.68 (s, 0.51H, minor isomer, CH$_3$), 2.34 (s, 2.49H, major isomer, CH$_3$), 1.32 (t, 3H, J=7.11 and 14.19 Hz, CH$_3$); $^{13}$C NMR (75 MHz, DMSO): δ 166.60, 165.69, 162.41, 157.81, 152.26, 150.83, 142.42, 133.23, 132.70, 132.18, 130.71, 129.03, 127.87, 127.35, 125.42, 121.39, 117.39, 112.97, 61.01, 14.67, 13.35. MS (ESI) m/z=477.1 [M−H]$^-$.

Synthesis of X80 (1) and 32. [(Z)-5-(5-((1-(3-Carboxyphenyl)-3-methyl-5-oxo-1H-pyrazol-4(5H)-ylidene)methyl)furan-2-yl)-2-chlorobenzoic acid] (X80)

To a stirred suspension of compound 31a (150 mg) in THF:MeOH (2:1, v/v, 10 mL) was added 2N NaOH (1 mL)

solution. The reaction mixture was stirred at room temperature for 6 h. Solvent was removed in vacuo and residue was acidified to pH 2-3 using 20% citric acid solution. The product was extracted with EtOAc (3×15 mL). The combined organic extracts were washed with brine, dried over $Na_2SO_4$ and concentrated under reduced pressure. The product was crystallized in EtOAc and triturated with 30% EtOAc in hexanes to afford X80 (120 mg, 85% yield) as an orange solid. Isomer data: $^1$H NMR (300 MHz, DMSO): δ 13.27 (brs, 1H, COOH), 12.88 (brs, 1H, COOH), 8.61 (d, 1H, J=3.7 Hz), 8.50 (t, 1H, J=1.95 and 3.85 Hz), 8.23 (d, 1H, J=1.95 Hz), 8.20 (d, 1H, J=7.35 Hz), 8.01 (m, 1H), 7.76-7.66 (m, 3H), 7.58-7.53 (m, 2H), 2.65 (s, 0.77H; minor isomer, $CH_3$), 2.37 (s, 2.23H; major isomer, $CH_3$). MS (ESI) m/z=473.1 [M+Na]$^+$; HRMS (ESI): calcd for $C_{23}H_{13}N_2O_6Cl$ [M−2H]$^−$ m/z=448.0462, found 448.0469. HPLC purity: 95.36%.

(Z)-5-(5-((1-(4-carboxyphenyl)-3-methyl-5-oxo-1H-pyrazol-4(5H)-ylidene)methyl)furan-2-yl)-2-chlorobenzoic acid (32)

32 was prepared by an above described procedure using 31b (200 mg) as starting material. Orange solid, (154 mg, 82% yield). $^1$H NMR (300 MHz, DMSO): δ 13.19 (brs, 1H, COOH), 12.84 (brs, 1H, COOH), 8.67 (d, 1H, J=3.84 Hz), 8.10-7.91 (m, 6H), 7.80-7.77 (m, 1H), 7.70 (d, 1H, J=8.64 Hz), 7.59-7.53 (m, 1H), 2.68 (s, 0.58H; minor isomer, $CH_3$), 2.34 (s, 2.43H; major isomer, $CH_3$). MS (ESI) m/z=448.1 [M−2H]$^−$; HRMS (ESI): calcd for $C_{23}H_{14}N_2O_6Cl$ [M−H]$^−$ m/z=449.0540, found 449.0547. HPLC purity: 95.13%.

General Synthesis of Amides 33a-j. (Z)-Ethyl 3-(4-((5-(4-chloro-3-((4-fluorobenzyl)carbamoyl)phenyl)furan-2-yl)methylene)-3-methyl-5-oxo-4,5-dihydro-1H-pyrazol-1-yl)benzoate (33a)

To a solution of compound 31a (300 mg, 1 equiv.) in dry DMF (6 mL) was added EDCI.HCl (180 mg, 1.5 equiv), HOBt (127 mg 1.5 equiv.), DIPEA (0.16 mL, 1.5 equiv.) and the mixture was stirred for 30 min at room temperature under an argon atmosphere. 4-Fluorobenzylamine (75 μL, 1.05 equiv.) and DIPEA (0.16 mL, 1.5 equiv.) were added to the reaction mixture. The reaction mixture was stirred at room temperature for 18 h. The reaction mixture was poured into water and extracted with EtOAc (3×20 mL). The combined organic extracts were washed with saturated $NaHCO_3$ (2×10 mL), brine, dried over $Na_2SO_4$ and concentrated under reduced pressure. The product was triturated with mixture of EtOAc in hexanes (2-3 times) to afford 33a (279 mg, 76% yield) as a red solid. TLC: 3% MeOH in DCM, $R_f$=0.45; visualized with UV. Isomer data: $^1$H NMR (300 MHz, DMSO): δ 9.16 (t, 1H, J=5.52 and 11.28 Hz), 8.66 (d, 1H, J=3.72 Hz), 8.53 (t, 1H, J=1.5 and 3.6 Hz, major), 8.23 (d, 1H, J=8.34 Hz), 8.03-7.92 (m, 2H), 7.81-7.74 (m, 2H), 7.72-7.67 (q, 1H), 7.62-7.54 (m, 2H), 7.43 (t, 2H, J=8.43 and 14.07 Hz), 7.24-7.16 (m, 2H), 4.49 (d, 2H, J=5.73 Hz, $NHCH_2$), 4.36-4.30 (q, 2H, $OCH_2$), 2.64 (s, 1.56H, $CH_3$), 2.35 (s, 1.44H, $CH_3$), 1.34 (t, 3H, J=7.08 and 14.16 Hz, $CH_3$); $^{13}$C NMR (75 MHz, DMSO): δ 166.24, 165.92, 162.23, 158.06, 151.81, 150.81, 139.01, 138.22, 135.56, 131.55, 131.33, 131.17, 130.25, 129.84, 129.74, 128.04, 127.85, 127.34, 125.51, 125.33, 122.67, 121.57, 118.62, 115.69, 115.41, 112.91, 61.44, 42.34, 14.67, 13.34. MS (ESI) m/z=586.1 [M+H]$^+$; HRMS (ESI): calcd for $C_{32}H_{26}N_3O_5ClF$ [M+H]$^+$ m/z=586.1545, found 586.1548. HPLC purity: 98.73%.

Compounds 33b-j were synthesized by an above synthetic procedure described for the preparation of amide 33a using appropriate starting materials. Each compound was triturated with the mixture of EtOAc in hexanes (2-3 times) to afford desired compound.

(Z)-Ethyl 3-(4-((5-(4-chloro-3-((3-methoxyphenyl) carbamoyl)phenyl)furan-2-yl)methylene)-3-(33b)

Red solid (226 mg, 62% yield). TLC: 3% MeOH in EtOAc, $R_f$=0.47; visualized with UV. Major Z-isomer data: $^1$H NMR (300 MHz, DMSO): δ 10.64 (s, 1H, NH), 8.65 (d, 1H, J=3.81 Hz), 8.52 (t, 1H, J=1.83 and 3.63 Hz), 8.22-8.14 (m, 2H), 8.06 (dd, 1H, J=2.16 and 8.46 Hz), 7.81-7.70 (m, 3H), 7.64-7.53 (m, 2H), 7.43 (s, 1H), 7.29-7.27 (m, 2H), 6.74-6.70 (m, 1H), 4.37-4.30 (q, 2H, $OCH_2$), 3.75 (s, 3H, $OCH_3$), 2.70 (s, 0.58H; minor isomer, $CH_3$), 2.33 (s, 2.42H; major isomer, $CH_3$), 1.33 (t, 3H, J=7.11 and 14.19 Hz, $CH_3$); $^{13}$C NMR (75 MHz, DMSO): δ 165.91, 164.69, 162.20, 160.01, 157.96, 151.75, 150.82, 140.40, 139.00, 138.22, 131.78, 131.52, 131.21, 130.66, 127.96, 125.69, 125.28, 121.63, 118.58, 112.32, 109.89, 105.83, 61.42, 55.51, 14.66, 13.30. MS (ESI) m/z=584.1 [M+H]$^+$; HRMS (ESI): calcd for $C_{32}H_{26}N_3O_6Cl$ [M]$^+$ m/z=583.1510, found 583.1524.

(Z)-Ethyl 3-(4-((5-(4-chloro-3-((3,4-dimethoxyphenyl)carbamoyl)phenyl)furan-2-yl)methylene)-3-methyl-5-oxo-4,5-dihydro-1H-pyrazol-1-yl)benzoate (33c)

Red solid (261 mg, 68% yield). TLC: 3% MeOH in EtOAc, $R_f$=0.54; visualized with UV. Major Z-isomer data: $^1$H NMR (300 MHz, DMSO): δ 10.52 (s, 1H, NH), 8.67 (d, 1H, J=3.72 Hz), 8.56-8.50 (m, 1H), 8.27-8.14 (m, 2H), 8.06-7.94 (m, 1H), 7.82-7.73 (m, 3H), 7.64-7.54 (m, 2H), 7.48-7.44 (m, 1H), 7.29-7.26 (dd, 1H, J=2.16 and 8.67 Hz), 6.97-6.94 (d, 1H, J=8.82 Hz), 4.38-4.31 (q, 2H, $OCH_2$), 3.75 (s, 6H, di$OCH_3$), 2.72 (s, 0.59H; minor isomer, $CH_3$), 2.34 (s, 2.41H; major isomer, $CH_3$), 1.34 (t, 3H, J=7.08 and 14.16 Hz, $CH_3$); $^{13}$C NMR (75 MHz, DMSO): δ 165.92, 164.21, 162.21, 158.01, 151.75, 150.81, 150.35, 149.00, 148.71, 145.79, 138.01, 138.83, 138.36, 138.22, 132.85, 131.84, 131.59, 131.19, 131.01, 130.18, 129.88, 128.01, 127.92, 127.38, 127.05, 125.72, 125.28, 122.59, 121.60, 118.58, 118.32, 112.93, 112.44, 111.97, 104.97, 61.43, 56.17, 55.84, 55.38, 14.66, 13.30. MS (ESI) m/z=614.1 [M+H]$^+$; HRMS (ESI): calcd for $C_{33}H_{29}N_3O_7Cl$ [M+H]$^+$ m/z=614.1694, found 614.1696.

(Z)-Ethyl 3-(4-((5-(4-chloro-3-((cyclopropylmethyl) carbamoyl)phenyl)furan-2-yl)methylene)-3-methyl-5-oxo-4,5-dihydro-1H-pyrazol-1-yl)benzoate (33d)

Red solid (249 mg, 75% yield). TLC: 3% MeOH in DCM, $R_f$=0.43; visualized with UV. Major Z-isomer data: $^1$H NMR (500 MHz, DMSO): δ 8.68-8.64 (m, 2H), 8.54 (t, 1H, J=1.8 and 3.55 Hz), 8.23-8.20 (m, 1H), 8.01-7.92 (m, 2H), 7.78-7.74 (m, 2H), 7.68 (d, 1H, J=8.3 Hz), 7.60-7.57 (m, 2H), 4.38-4.33 (q, 2H, $OCH_2$), 3.18 (m, 2H, $NHCH_2$), 2.72 (s, 0.64H; minor isomer, $CH_3$), 2.35 (s, 2.36H; major isomer, $CH_3$), 1.35 (t, 3H, J=7.1 and 14.2 Hz, $CH_3$), 1.06-1.0 (m, 1H, CH), 0.49-0.45 (m, 2H, $CH_2$), 0.28-0.25 (m, 2H, $CH_2$); $^{13}$C NMR (125 MHz, DMSO): δ 165.51, 165.44, 161.74, 157.65, 151.27, 150.29, 138.54, 138.14, 131.07, 130.56, 129.68, 129.37, 127.54, 127.29, 126.66, 124.96, 124.80, 112.16, 121.05, 118.16, 112.28, 60.92, 43.24, 14.17, 12.81, 10.65. MS (ESI) m/z=532.1 [M+H]⁺; HRMS (ESI): calcd for $C_{29}H_{27}N_3O_5Cl$ [M+H]⁺ m/z=532.1639, found 532.1640.

(Z)-Ethyl 3-(4-((5-(4-chloro-3-(cyclopropylcarbamoyl)phenyl)furan-2-yl)methylene)-3-methyl-5-oxo-4,5-dihydro-1H-pyrazol-1-yl)benzoate (33e)

Red solid (223 mg, 69% yield). TLC: 3% MeOH in DCM, $R_f$=0.46; visualized with UV. Major Z-isomer data: ¹H NMR (300 MHz, DMSO): δ 8.68 (d, 1H, J=4.26 Hz), 8.63 (d, 1H, J=3.6 Hz), 8.52 (s, 1H), 8.22 (d, 1H, J=7.41 Hz), 7.97-7.88 (m, 2H), 7.79-7.73 (m, 2H), 7.67-7.52 (m, 3H), 4.37-4.30 (q, 2H, OCH₂), 2-88-2.82 (m, 1H, CH) 2.68 (s, 0.46H; minor isomer, CH₃), 2.35 (s, 2.54H; major isomer, CH₃), 1.33 (t, 3H, J=7.08 and 14.13 Hz, CH₃), 0.75-0.69 (m, 2H, CH₂), 0.58-0.53 (m, 2H, CH₂); ¹³C NMR (75 MHz, DMSO): δ 167.19, 165.92, 162.20, 158.09, 151.76, 150.75, 139.02, 138.83, 138.34, 138.06, 131.04, 130.17, 129.88, 128.05, 127.75, 127.16, 125.51, 125.27, 122.59, 121.50, 118.58, 112.83, 61.42, 23.23, 14.67, 13.33, 6.16. MS (ESI) m/z=518.1 [M+H]⁺; HRMS (ESI): calcd for $C_{28}H_{25}N_3O_5Cl$ [M+H]⁺ m/z=518.1483, found 518.1488.

(Z)-Ethyl 3-(4-((5-(4-chloro-3-((tetrahydro-2H-pyran-4-yl)carbamoyl)phenyl)furan-2-yl)methylene)-3-methyl-5-oxo-4,5-dihydro-1H-pyrazol-1-yl)benzoate (33f)

Red solid (246 mg, 70% yield). TLC: 3% MeOH in DCM, $R_f$=0.45; visualized with UV. Major Z-isomer data: ¹H NMR (300 MHz, DMSO): δ 8.69 (m, 2H), 8.53 (t, 1H, J=1.71 and 3.51 Hz), 8.26-8.20 (m, 1H), 8.02-7.87 (m, 2H), 7.79 (s, 1H), 7.75 (d, 1H, J=8.1 Hz), 7.69-7.55 (m, 3H), 4.38-4.31 (q, 2H, OCH₂), 4.04-3.92 (m, 1H, CH), 3.90-3.84 (m, 2H, CH₂), 3.45-3.39 (m, 2H, CH₂), 2.71 (s, 0.58H; minor isomer, CH₃), 2.34 (s, 2.42H; major isomer, CH₃), 1.85-1.75 (m, 2H, CH₂), 1.60-1.45 (m, 2H, CH₂), 1.33 (t, 3H, J=7.08 and 14.01 Hz, CH₃); ¹³C NMR (75 MHz, DMSO): δ 166.29, 165.92, 165.37, 162.21, 158.13, 156.81, 152.40, 151.81, 150.77, 146.86, 141.35, 139.03, 138.55, 138.40, 131.41, 131.02, 130.59, 130.24, 127.93, 127.78, 127.16, 125.33, 124.64, 122.65, 121.49, 118.62, 110.44, 66.29, 61.44, 46.06, 32.62, 14.67, 13.36. MS (ESI) m/z=562.1 [M+H]⁺; HRMS (ESI): calcd for $C_{30}H_{29}N_3O_6Cl$ [M+H]⁺ m/z=562.1745, found 562.1753.

(Z)-Ethyl 3-(4-((5-(4-chloro-3-(((tetrahydro-2H-pyran-4-yl)methyl)carbamoyl)phenyl)furan-2-yl)methylene)-3-methyl-5-oxo-4,5-dihydro-1H-pyrazol-1-yl)benzoate (33g)

Red solid (267 mg, 74% yield). TLC: 3% MeOH in DCM, $R_f$=0.45; visualized with UV. Major Z-isomer data: ¹H NMR (300 MHz, DMSO): δ 8.69-8.63 (m, 2H), 8.53 (s, 1H), 8.22 (d, 1H, J=9.06 Hz), 7.99-7.90 (m, 2H), 7.81-7.74 (m, 1H), 7.77 (s, 1H), 7.67-7.53 (m, 3H), 4.38-4.28 (q, 2H, OCH₂), 3.90-3.81 (m, 2H, CH₂), 3.32-3.22 (m, 2H, CH₂), 3.19-3.13 (m, 2H, NHCH₂), 2.72 (s, 0.58H; minor isomer, CH₃), 2.34 (s, 2.42H; major isomer, CH₃), 1.84-1.71 (m, 1H, CH), 1.69-1.60 (m, 2H, CH₂), 1.33 (t, 3H, J=7.08 and 13.95 Hz, CH₃), 1.26-1.15 (m, 2H, CH₂); ¹³C NMR (75 MHz, DMSO): δ 178.58, 166.65, 166.24, 165.92, 162.22, 158.13, 156.80, 152.40, 151.79, 150.77, 146.85, 141.35, 139.02, 138.68, 138.52, 131.72, 131.02, 130.60, 127.95, 127.88, 127.79, 125.30, 124.65, 122.65, 121.51, 119.60, 112.86, 110.42, 108.52, 67.22, 61.43, 45.27, 36.25, 31.22, 14.69, 13.43. MS (ESI) m/z=576.2 [M+H]⁺; HRMS (ESI): calcd for $C_{31}H_{31}N_3O_6Cl$ [M+H]⁺ m/z=576.1901, found 576.1913.

(Z)-Ethyl 4-(4-((5-(4-chloro-3-((4-fluorobenzyl)carbamoyl)phenyl)furan-2-yl)methylene)-3-methyl-5-oxo-4,5-dihydro-1H-pyrazol-1-yl)benzoate (33h)

Red solid (300 mg, 79% yield). TLC: 3% MeOH in DCM, $R_f$=0.47; visualized with UV. Major Z-isomer data: ¹H NMR (300 MHz, DMSO): δ 9.17 (t, 1H, J=5.88 and 11.76 Hz), 8.62 (s, 1H), 8.16-7.97 (m, 6H), 7.75 (s, 1H), 7.69 (d, 1H, J=8.4 Hz), 7.60 (d, 1H, J=3.33 Hz), 7.45-7.41 (m, 2H), 7.22-7.18 (m, 2H), 4.49 (d, 2H, J=5.76 Hz, NHCH₂), 4.32-4.25 (q, 2H, OCH₂), 2.62 (s, 0.74H; minor isomer, CH₃), 2.33 (s, 2.26H; major isomer, CH₃), 1.31 (t, 3H, J=7.08 and 14.1 Hz, CH₃); ¹³C NMR (75 MHz, DMSO): δ 166.23, 166.07, 165.23, 162.53, 158.66, 158.19, 154.90, 151.00, 150.74, 150.37, 149.06, 144.85, 142.46, 138.22, 138.04, 135.57, 131.61, 131.34, 130.78, 130.35, 129.73, 127.99, 127.83, 126.52, 125.53, 124.10, 121.33, 118.28, 117.52, 115.91, 115.69, 115.41, 112.89, 61.05, 44.84, 14.69, 13.47. MS (ESI) m/z=586.1 [M+H]⁺; HRMS (ESI): calcd for $C_{32}H_{26}N_3O_5ClF$ [M+H]⁺ m/z=586.1545, found 586.1549.

(Z)-Ethyl 4-(4-((5-(4-chloro-3-((3-methoxyphenyl)carbamoyl)phenyl)furan-2-yl)methylene)-3-methyl-5-oxo-4,5-dihydro-1H-pyrazol-1-yl)benzoate (33i)

Dark Red solid (272 mg, 67% yield). TLC: 3% MeOH in EtOAc, $R_f$=0.49; visualized with UV. Major Z-isomer data: ¹H NMR (300 MHz, DMSO): δ 10.66 (s, 1H, NH), 8.60 (d, 1H, J=3.0 Hz), 8.20 (d, 1H, J=1.5 Hz), 8.14-7.94 (m, 5H), 7.82-7.73 (m, 2H), 7.63-7.54 (m, 1H), 7.45-7.39 (m/brs, 1H), 7.29-7.23 (m, 2H), 6.74-6.69 (m, 1H), 4.323-4.26 (q, 2H, OCH₂), 3.75 (s, 3H, OCH₃), 2.70 (s, 072.H; minor isomer, CH₃), 2.32 (s, 2.31H; major isomer, CH₃), 1.32 (t, 3H, J=7.05 and 14.04 Hz, CH₃); ¹³C NMR (75 MHz, DMSO): δ 165.70, 164.69, 162.43, 160.01, 158.07, 152.30, 150.79, 150.44, 142.44, 140.41, 138.20, 131.58, 131.22, 130.74, 130.16, 129.06, 127.92, 125.76, 125.46, 121.36, 117.42, 112.97, 112.31, 109.89, 105.82, 61.04, 55.51, 55.38, 54.95, 14.69, 13.34. MS (ESI) m/z=584.1 [M+H]⁺; HRMS (ESI): calcd for $C_{30}H_{21}N_3O_6Cl$ [M−H]⁻ m/z=584.1588, found 584.1596.

(Z)-Ethyl 4-(4-((5-(4-chloro-3-((cyclopropylmethyl)carbamoyl)phenyl)furan-2-yl)methylene)-3-methyl-5-oxo-4,5-dihydro-1H-pyrazol-1-yl)benzoate (33j)

Red solid (364 mg, 82% yield). TLC: 3% MeOH in DCM, $R_f$=0.44; visualized with UV. Major Z-isomer data: ¹H NMR (300 MHz, DMSO): δ 8.74 (t, 1H, J=5.31 and 10.5 Hz), 8.59 (s, 1H), 8.07 (t, 2H, J=8.73 and 17.7 Hz), 8.0 (d, 4H, J=7.83 Hz), 7.75 (s, 1H), 7.66 (d, 1H, J=8.85 Hz), 7.58 (d, 1H, J=3.96 Hz), 4.32-4.25 (q, 2H, OCH₂), 3.16 (t, 2H, J=6.09 and 12.42 Hz, NHCH₂), 2.68 (s, 0.66H; minor isomer, CH₃), 2.32 (s, 2.34H; major isomer, CH₃), 1.31 (t, 3H, J=7.11 and 14.16 Hz, CH₃), 1.09-0.98 (m, 1H, CH), 0.48-0.42 (m, 2H, CH₂), 0.28-0.23 (m, 2H, CH₂); ¹³C NMR (75 MHz, DMSO): δ 166.00, 166.07, 165.92, 162.49, 158.74, 157.92, 152.39, 150.77, 150.34, 148.97, 142.47, 138.63, 138.42, 131.62, 131.12, 130.77, 127.95, 127.73, 127.20, 125.50, 121.07, 119.60, 117.51, 112.81, 61.06, 43.68, 14.70, 13.39, 11.17, 3.36. MS (ESI) m/z=532.1 [M+H]⁺; HRMS (ESI): calcd for $C_{29}H_{27}N_3O_5Cl$ [M+H]⁺ m/z=532.1639, found 532.1642.

General Synthesis of Target Compounds 34a-d and 34f-k. (Z)-3-(4-((5-(4-Chloro-3-((4-fluorobenzyl) carbamoyl)phenyl)furan-2-yl)methylene)-3-methyl-5-oxo-4,5-dihydro-1H-pyrazol-1-yl)benzoic acid (34a)

To a stirred suspension of ester 33a (80 mg, 1 equiv.) in THF:EtOH:H$_2$O (4:2:1, 7 mL) was added LiOH (32 mg, 10 equiv.). The reaction mixture was stirred at room temperature for 12 h. Solvent was removed in vacuo and residue was acidified to pH 2-3 using 20% citric acid solution. The product was extracted with EtOAc (3×15 mL). The combined organic extracts were washed with brine, dried over Na$_2$SO$_4$ and concentrated under reduced pressure. The product was crystallized in EtOH, solid was collected, washed with EtOAc and then hot solutions of 20-30% EtOAc in hexanes to afford target compound 34a (47 mg, 62% yield) as a red solid. Major Z-isomer data: $^1$H NMR (500 MHz, DMSO): δ 9.15 (t, 1H, J=5.8 and 11.7 Hz), 8.68 (d, 1H, J=3.05 Hz), 8.56 (t, 1H, J=1.7 and 3.85 Hz), 8.20 (d, 1H, J=7.45 Hz), 8.04-7.94 (m, 2H), 7.82-7.69 (m, 2H), 7.71 (t, 1H, J=8.15 and 16.45 Hz), 7.62-7.55 (m, 2H), 7.45-7.42 (m, 2H), 7.22-7.17 (m, 2H), 4.49 (d, 2H, J=5.85 Hz, NHCH$_2$), 2.68 (s, 0.76H; minor isomer, CH$_3$), 2.36 (s, 2.24H; major isomer, CH$_3$). MS (ESI) m/z=556.1 [M−H]$^-$; HRMS (ESI): calcd for C$_{30}$H$_{20}$N$_3$O$_5$ClF [M−H]$^-$ m/z=556.1076, found 556.1079. HPLC purity: 97.24%.

Target Compounds 34b-d and 34f-k were synthesized by an above synthetic procedure described for the preparation of compound 34a using appropriate starting materials. Each compound was crystallized in EtOH, solid was collected, washed with EtOAc and then hot solutions of 20-30% EtOAc in hexanes to afford desired final compound. If necessary, the products were purified using 2-5% MeOH in DCM (1% AcOH in DCM) solvent system on automated flash column chromatography.

(Z)-3-(4-((5-(4-Chloro-3-((3-methoxyphenyl)carbamoyl)phenyl)furan-2-yl)methylene)-3-methyl-5-oxo-4,5-dihydro-1H-pyrazol-1-yl)benzoic acid (34b)

Red solid (111 mg, 69% yield). Major Z-isomer data: $^1$H NMR (300 MHz, DMSO): δ 13.04 (brs, 1H, COOH), 10.65 (s, 1H, NH), 8.69 (d, 1H, J=3.16 Hz), 8.55 (t, 1H, J=1.95 and 3.5 Hz), 8.31-8.19 (m, 2H), 8.08-7.97 (m, 1H), 7.80-7.70 (m, 3H), 7.65-7.55 (m, 2H), 7.43 (s, 1H), 7.29-7.28 (m, 2H), 6.74-6.69 (m, 1H), 3.76 (s, 3H, OCH$_3$), 2.73 (s, 0.51H; minor isomer, CH$_3$), 2.34 (s, 2.49H; major isomer, CH$_3$); $^{13}$C NMR (75 MHz, DMSO): δ 172.50, 167.51, 167.28, 165.08, 164.69, 162.22, 160.01, 157.94, 151.59, 140.41, 138.93, 132.03, 131.93, 131.22, 130.72, 129.72, 129.47, 125.48, 124.69, 122.30, 121.74, 112.32, 109.89, 105.83, 55.52, 13.30. MS (ESI) m/z=554.1 [M−H]$^-$; HRMS (ESI): calcd for C$_{30}$H$_{21}$N$_3$O$_6$Cl [M−H]$^-$ m/z=554.1119, found 554.1124. HPLC purity: 98.63%.

(Z)-3-(4-((5-(4-Chloro-3-((3,4-dimethoxyphenyl) carbamoyl)phenyl)furan-2-yl)methylene)-3-methyl-5-oxo-4,5-dihydro-1H-pyrazol-1-yl)benzoic acid (34c)

Red solid (60 mg, 63% yield). Major Z-isomer data: $^1$H NMR (300 MHz, DMSO): δ 13.14 (brs, 1H, COOH), 10.52 (s, 1H, NH), 8.70 (d, 1H, J=3.75 Hz), 8.56-8.51 (m, 1H), 8.28-8.15 (m, 2H), 8.08-7.95 (m, 1H), 7.80-7.74 (m, 3H), 7.65-7.55 (m, 2H), 7.47-7.43 (m, 1H), 7.30-7.27 (m, 1H), 6.97-6.90 (m, 1H), 3.75 and 3.74 (s, 6H, diOCH$_3$), 2.74 (s, 0.49H; minor isomer, CH$_3$), 2.35 (s, 2.49H; major isomer, CH$_3$); $^{13}$C NMR (75 MHz, DMSO): δ 167.51, 164.22, 164.69, 162.22, 157.99, 151.70, 150.84, 149.00, 145.79, 138.93, 138.37, 131.93, 131.58, 130.46, 129.74, 127.94, 127.39, 125.73, 125.43, 122.30, 121.71, 118.96, 112.44, 111.98, 104.97, 105.83, 56.17, 55.84, 13.30. MS (ESI) m/z=584.1 [M−H]$^-$; HRMS (ESI): calcd for C$_{31}$H$_{23}$N$_3$O$_7$Cl [M−H]$^-$ m/z=584.1225, found 584.1229. HPLC purity: 95.07%.

(Z)-3-(4-((5-(4-Chloro-3-((cyclopropylmethyl)carbamoyl)phenyl)furan-2-yl)methylene)-3-methyl-5-oxo-4,5-dihydro-1H-pyrazol-1-yl)benzoic acid (34d)

Red solid (56 mg, 60% yield). Major Z-isomer data: $^1$H NMR (300 MHz, DMSO): δ 13.10 (brs, 1H, COOH), 8.71-8.65 (m, 2H), 8.55 (s, 1H), 8.20 (d, 1H, J=7.74 Hz), 8.02-7.94 (m, 2H), 7.83-7.66 (m, 3H), 7.62-7.53 (m, 2H), 3.19-3.13 (m, 2H, NHCH$_2$), 2.73 (s, 0.71H; minor isomer, CH$_3$), 2.35 (s, 2.29H; major isomer, CH$_3$), 1.07-0.95 (m, 1H, CH), 0.48-0.42 (m, 2H, CH$_2$), 0.28-0.23 (m, 2H, CH$_2$); $^{13}$C NMR (75 MHz, DMSO): δ 167.50, 166.00, 162.22, 158.11, 151.71, 150.80, 138.94, 138.63, 131.93, 131.54, 130.07, 129.73, 128.01, 127.78, 127.15, 125.49, 122.31, 121.61, 118.97, 112.81, 43.71, 13.32, 11.16, 3.73. MS (ESI) m/z=502.1 [M−H]$^-$; HRMS (ESI): calcd for C$_{27}$H$_{21}$N$_3$O$_5$Cl [M−H]$^-$ m/z=502.1170, found 502.1172. HPLC purity: 97.11%.

(Z)-3-(4-((5-(4-Chloro-3-(cyclopropylcarbamoyl) phenyl)furan-2-yl)methylene)-3-methyl-5-oxo-4,5-dihydro-1H-pyrazol-1-yl)benzoic acid (34f)

Red solid (64 mg, 68% yield). Major Z-isomer data: $^1$H NMR (300 MHz, DMSO): δ 13.12 (brs, 1H, COOH), 8.66-8.63 (m, 2H), 8.54 (t, 1H, J=1.77 and 3.54 Hz), 8.20 (d, 1H, J=8.16 Hz), 8.00-7.94 (m, 2H), 7.82-7.73 (m, 2H), 7.69-7.64 (m, 1H), 7.60-7.53 (m, 2H), 2.89-2.80 (m, 1H, CH), 2.71 (s, 1.10H; minor isomer, CH$_3$), 2.34 (s, 1.90H; major isomer, CH$_3$), 0.77-0.69 (m, 2H, CH$_2$), 0.58-0.53 (m, 2H, CH$_2$); $^{13}$C NMR (75 MHz, DMSO): δ 167.50, 167.19, 162.21, 158.06, 151.69, 150.78, 138.94, 138.38, 131.93, 131.57, 131.06, 130.15, 129.73, 127.99, 127.78, 127.15, 126.49, 122.29, 121.62, 118.95, 112.81, 23.22, 13.32, 6.18. MS (ESI) m/z=488.1 [M−H]$^-$; HRMS (ESI): calcd for C$_{26}$H$_{19}$N$_3$O$_5$Cl [M−H]$^-$ m/z=488.1013, found 488.1017. HPLC purity: 95.74%.

(Z)-3-(4-((5-(4-Chloro-3-((tetrahydro-2H-pyran-4-yl)carbamoyl)phenyl)furan-2-yl)methylene)-3-methyl-5-oxo-4,5-dihydro-1H-pyrazol-1-yl)benzoic acid (34g)

Red solid (72 mg, 76% yield). Major Z-isomer data: $^1$H NMR (300 MHz, DMSO): δ 13.11 (brs, 1H, COOH), 8.65-8.59 (m, 2H), 8.54 (t, 1H, J=1.71 and 3.42 Hz), 8.20 (d, 1H, J=8.16 Hz), 8.01-7.93 (m, 2H), 7.82-7.73 (m, 2H), 7.70-7.65 (m, 1H), 7.61-7.53 (m, 2H), 4.05-3.95 (m, 1H, CH), 3.91-3.84 (m, 2H, CH$_2$), 3.46-3.41 (m, 2H, CH$_2$), 2.72 (s, 0.77H; minor isomer, CH$_3$), 2.34 (s, 2.23H; major isomer, CH$_3$), 1.86-1.79 (m, 2H, CH$_2$), 1.59-1.46 (m, 2H, CH$_2$); $^{13}$C NMR (75 MHz, DMSO): δ 167.50, 165.37, 162.19, 158.07, 151.68, 150.79, 138.94, 138.57, 131.92, 131.56, 131.03, 130.13, 129.71, 128.02, 127.80, 127.14, 125.34, 122.29, 121.60, 118.96, 112.81, 66.28, 46.05, 32.65, 13.32. MS (ESI) m/z=532.1 [M−H]−; HRMS (ESI): calcd for C$_{28}$H$_{23}$N$_3$O$_6$Cl [M−H]− m/z=532.1275, found 532.1281. HPLC purity: 96.33%.

(Z)-3-(4-((5-(4-Chloro-3-(((tetrahydro-2H-pyran-4-yl)methyl)carbamoyl)phenyl)furan-2-yl)methylene)-3-methyl-5-oxo-4,5-dihydro-1H-pyrazol-1-yl)benzoic acid (34h)

Red solid (66 mg, 70% yield). Major Z-isomer data: $^1$H NMR (300 MHz, DMSO): δ 13.12 (brs, 1H, COOH), 8.65-8.59 (m, 2H), 8.54 (s, 1H), 8.19 (d, 1H, J=7.77 Hz), 8.01-7.92 (m, 2H), 7.82-7.73 (m, 2H), 7.69-7.65 (m, 1H), 7.60-7.54 (m, 2H), 3.90-3.81 (m, 2H, CH$_2$), 3.28-3.22 (m, 2H, CH$_2$), 3.19-3.13 (m, 2H, NHCH$_2$), 2.70 (s, 0.67H; minor isomer, CH$_3$), 2.34 (s, 2.33H; major isomer, CH$_3$), 1.84-1.72 (m, 1H, CH), 1.69-1.61 (m, 2H, CH$_2$), 1.30-1.14 (m, 2H, CH$_2$); $^{13}$C NMR (75 MHz, DMSO): δ 167.00, 165.75, 161.70, 157.56, 151.18, 150.29, 138.42, 138.18, 131.41, 130.93, 130.54, 129.66, 129.22, 127.47, 127.31, 126.60, 124.98, 121.79, 121.10, 118.45, 112.32, 66.72, 44.78, 34.77, 30.40, 12.80. MS (ESI) m/z=546.1 [M−H]−; HRMS (ESI): calcd for C$_{29}$H$_{25}$N$_3$O$_6$Cl [M−H]− m/z=546.1432, found 546.1434. HPLC purity: 97.82%.

(Z)-4-(4-((5-(4-Chloro-3-((4-fluorobenzyl)carbamoyl)phenyl)furan-2-yl)methylene)-3-methyl-5-oxo-4,5-dihydro-1H-pyrazol-1-yl)benzoic acid (34i)

Red solid (66 mg, 70% yield). Isomer data: $^1$H NMR (300 MHz, DMSO): δ 12.85 (brs, 1H, COOH), 9.17 (t, 1H, J=5.88 and 11.79 Hz), 8.64 (d, 1H, J=3.66 Hz), 8.10-7.92 (m, 6H), 7.83-7.79 (m, 1H), 7.71 (dd, 1H, J=2.67 and 8.4 Hz), 7.62-7.56 (m, 1H), 7.45-7.40 (m, 2H), 7.23-7.15 (m, 2H), 4.48 (d, 2H, J=5.88 Hz, NHCH$_2$), 2.66 (s, 1.65H, CH$_3$), 2.34 (s, 1.35H, CH$_3$); $^{13}$C NMR (75 MHz, DMSO): δ 167.31, 166.23, 166.11, 165.28, 162.44, 160.10, 159.56, 158.15, 152.22, 150.81, 150.33, 149.13, 142.20, 142.00, 138.22, 138.04, 135.56, 131.83, 131.59, 131.47, 131.17, 131.03, 130.93, 127.83, 127.73, 126.52, 125.90, 125.54, 121.41, 119.71, 117.47, 117.25, 115.69, 115.42, 112.93, 42.32, 13.37. MS (ESI) m/z=556.1 [M−H]−; HRMS (ESI): calcd for C$_{30}$H$_{20}$N$_3$O$_5$ClF [M−H]− m/z=556.1076, found 556.1077. HPLC purity: 98.93%.

(Z)-4-(4-((5-(4-Chloro-3-((3-methoxyphenyl)carbamoyl)phenyl)furan-2-yl)methylene)-3-methyl-5-oxo-4,5-dihydro-1H-pyrazol-1-yl)benzoic acid (34j)

Red solid (60 mg, 63% yield). Major Z-isomer data: $^1$H NMR (300 MHz, DMSO): δ 12.86 (brs, 1H, COOH), 10.55 (s, 1H, NH), 8.14-7.96 (m, 4H), 7.95-7.85 (m, 3H), 7.83-7.75 (m, 1H), 7.73-7.66 (m, 1H), 7.61-7.54 (m, 1H), 7.47-7.40 (m, 1H), 7.32-7.23 (m, 2H), 6.75-6.67 (m, 1H), 3.74 (s, 3H, OCH$_3$), 2.74 (s, 0.24H; minor isomer, CH$_3$), 2.35 (s, 2.87H; major isomer, CH$_3$); $^{13}$C NMR (75 MHz, DMSO): δ 167.21, 165.10, 164.66, 162.20, 159.98, 157.91, 150.39, 140.46, 137.86, 132.01, 131.58, 130.86, 130.07, 129.92, 128.42, 127.51, 125.52, 123.55, 122.26, 119.96, 119.68, 112.32, 109.79, 105.80, 55.47, 13.36. MS (ESI) m/z=554.1 [M−H]−; HRMS (ESI): calcd for C$_{30}$H$_{21}$N$_3$O$_6$Cl [M−H]− m/z=554.1119, found 554.1122. HPLC purity: 96.34%.

(Z)-4-(4-((5-(4-Chloro-3-((cyclopropylmethyl)carbamoyl)phenyl)furan-2-yl)methylene)-3-methyl-5-oxo-4,5-dihydro-1H-pyrazol-1-yl)benzoic acid (34k)

Red solid (89 mg, 63% yield). Major Z-isomer data: $^1$H NMR (300 MHz, DMSO): δ 12.83 (brs, 1H, COOH), 8.67 (t, 1H, J=5.1 and 10.2 Hz), 8.60 (s, 1H), 8.06 (t, 2H, J=8.01 and 14.19 Hz), 8.0 (d, 4H, J=8.55 Hz), 7.76 (s, 1H), 7.67 (d, 1H, J=8.64 Hz), 7.58 (d, 1H, J=3.9 Hz), 3.17 (t, 2H, J=5.7 and 11.4 Hz, NHCH$_2$), 2.70 (s, 0.81H; minor isomer, CH$_3$), 2.33 (s, 2.19H; major isomer, CH$_3$), 1.08-0.94 (m, 1H, CH), 0.49-0.40 (m, 2H, CH$_2$), 0.28-0.22 (m, 2H, CH$_2$); $^{13}$C NMR (75 MHz, DMSO): δ 167.31, 166.01, 165.91, 162.41, 159.64, 158.22, 152.18, 150.76, 150.29, 149.09, 142.21, 138.60, 138.39, 131.83, 131.05, 130.21, 128.18, 127.74, 127.16, 126.44, 125.45, 121.33, 119.62, 117.542, 112.81, 43.71, 13.35, 11.17, 3.73. MS (ESI) m/z=502.1 [M−H]−; HRMS (ESI): calcd for C$_{27}$H$_{21}$N$_3$O$_5$Cl [M−H]− m/z=502.1170, found 502.1171. HPLC purity: 95.18%.

Synthesis of Target Compound 34e. (Z)-2-Chloro-N-(cyclopropylmethyl)-5-(5-((1-(3-((cyclopropylmethyl)carbamoyl)phenyl)-3-methyl-5-oxo-1H-pyrazol-4(5H)-ylidene)methyl)furan-2-yl)benzamide (34e)

34e was synthesized using an above synthetic procedure described for the preparation of compound 33a using 34d as a starting material. Product was crystallized in EtOH, solid was collected, washed with EtOAc and then hot solutions of 20-30% EtOAc in hexanes to afford 34e as a red solid (51 mg, 78% yield). TLC: 4% MeOH in DCM, R$_f$=0.42; visualized with UV. Major Z-isomer data: $^1$H NMR (300 MHz, DMSO): δ 8.70-8.65 (m, 3H), 8.36 (s, 1H), 8.11 (d, 1H, J=7.83 Hz), 7.99-7.91 (m, 2H), 7.77 (s, 1H), 7.68-7.65 (m, 2H), 7.58 (d, 1H, J=3.9 Hz), 7.54-7.48 (m, 1H), 3.19-3.13 (q, 4H, 2NHCH$_2$), 2.72 (s, 0.56H; minor isomer, CH$_3$), 2.34 (s, 2.44H; major isomer, CH$_3$), 1.07-0.95 (m, 2H, 2CH), 0.49-0.41 (m, 4H, 2CH$_2$), 0.27-0.23 (m, 4H, 2CH$_2$); $^{13}$C NMR (75 MHz, DMSO): δ 166.30, 166.01, 162.14, 159.49, 158.05, 151.50, 150.80, 138.76, 138.61, 136.01, 131.51, 131.23, 131.07, 130.05, 129.23, 127.91, 127.78, 125.41, 123.34, 121.66, 120.89, 117.69, 112.76, 44.08, 43.71 13.31, 11.49, 11.16, 3.73 (t). MS (ESI) m/z=557.1 [M+H]+; HRMS (ESI): calcd for C$_{31}$H$_{30}$N$_4$O$_4$Cl [M+H]+ m/z=557.1956, found 557.1957.

Compounds NG-01-70, NG-01-78, NG-02-99, NG-02-100, were synthesized by an above synthetic procedure described for the preparation of compound NG-01-64 using appropriate starting materials. Each compound was crystallized in EtOH, solid was collected, washed with EtOAc and then hot solutions of 20-30% EtOAc in hexanes to afford desired final compound. All synthetic compounds for in vitro studies were ≥95% purity as determined by an absolute quantitative $^1$H NMR spectroscopy (*J. Med. Chem.*, 2014, 57(22), 9219-9219 and *J. Med. Chem.*, 2014, 57(22), 9220-9231).

(Z)-3-(4-((5-(4-Chloro-3-((cyclopropylmethyl)carbamoyl)phenyl)furan-2-yl)methylene)-3-methyl-5-oxo-4,5-dihydro-1H-pyrazol-1-yl)benzoic acid (NG-01-70)

Red solid (56 mg, 60% yield).
Major Z-isomer data: $^1$H NMR (300 MHz, DMSO): δ 13.10 (brs, 1H, COOH), 8.71-8.65 (m, 2H), 8.55 (s, 1H), 8.20 (d, 1H, J=7.74 Hz), 8.02-7.94 (m, 2H), 7.83-7.66 (m, 3H), 7.62-7.53 (m, 2H), 3.19-3.13 (m, 2H, NHCH$_2$), 2.73 (s, 0.71H, minor isomer, CH$_3$), 2.35 (s, 2.29H, major isomer, CH$_3$), 1.07-0.95 (m, 1H, CH), 0.48-0.42 (m, 2H, CH$_2$), 0.28-0.23 (m, 2H, CH$_2$); $^{13}$C NMR (75 MHz, DMSO): δ 167.50, 166.00, 162.22, 158.11, 151.71, 150.80, 138.94, 138.63, 131.93, 131.54, 130.07, 129.73, 128.01, 127.78, 127.15, 125.49, 122.31, 121.61, 118.97, 112.81, 43.71, 13.32, 11.16, 3.73.

(Z)-3-(4-((5-(4-Chloro-3-(cyclopropylcarbamoyl) phenyl)furan-2-yl)methylene)-3-methyl-5-oxo-4,5-dihydro-1H-pyrazol-1-yl)benzoic acid (NG-01-78)

Red solid (64 mg, 68% yield).

Major Z-isomer data: $^1$H NMR (300 MHz, DMSO): δ 13.12 (brs, 1H, COOH), 8.66-8.63 (m, 2H), 8.54 (t, 1H, J=1.77 and 3.54 Hz), 8.20 (d, 1H, J=8.16 Hz), 8.00-7.94 (m, 2H), 7.82-7.73 (m, 2H), 7.69-7.64 (m, 1H), 7.60-7.53 (m, 2H), 2.89-2.80 (m, 1H, CH), 2.71 (s, 1.10H, minor isomer, CH$_3$), 2.34 (s, 1.90H, major isomer, CH$_3$), 0.77-0.69 (m, 2H, CH$_2$), 0.58-0.53 (m, 2H, CH$_2$); $^{13}$C NMR (75 MHz, DMSO): δ 167.50, 167.19, 162.21, 158.06, 151.69, 150.78, 138.94, 138.38, 131.93, 131.57, 131.06, 130.15, 129.73, 127.99, 127.78, 127.15, 126.49, 122.29, 121.62, 118.95, 112.81, 23.22, 13.32, 6.18.

(Z)-3-(4-((5-(4-Chloro-3-((tetrahydro-2H-pyran-4-yl)carbamoyl)phenyl)furan-2-yl)methylene)-3-methyl-5-oxo-4,5-dihydro-1H-pyrazol-1-yl)benzoic acid (NG-02-99)

Red solid (72 mg, 76% yield).

Major Z-isomer data: $^1$H NMR (300 MHz, DMSO): δ 13.11 (brs, 1H, COOH), 8.65-8.59 (m, 2H), 8.54 (t, 1H, J=1.71 and 3.42 Hz), 8.20 (d, 1H, J=8.16 Hz), 8.01-7.93 (m, 2H), 7.82-7.73 (m, 2H), 7.70-7.65 (m, 1H), 7.61-7.53 (m, 2H), 4.05-3.95 (m, 1H, CH), 3.91-3.84 (m, 2H, CH$_2$), 3.46-3.41 (m, 2H, CH$_2$), 2.72 (s, 0.77H, minor isomer, CH$_3$), 2.34 (s, 2.23H, major isomer, CH$_3$), 1.86-1.79 (m, 2H, CH$_2$), 1.59-1.46 (m, 2H, CH$_2$); $^{13}$C NMR (75 MHz, DMSO): δ 167.50, 165.37, 162.19, 158.07, 151.68, 150.79, 138.94, 138.57, 131.92, 131.56, 131.03, 130.13, 129.71, 128.02, 127.80, 127.14, 125.34, 122.29, 121.60, 118.96, 112.81, 66.28, 46.05, 32.65, 13.32.

(Z)-3-(4-((5-(4-Chloro-3-(((tetrahydro-2H-pyran-4-yl)methyl)carbamoyl)phenyl)furan-2-yl)methylene)-3-methyl-5-oxo-4,5-dihydro-1H-pyrazol-1-yl)benzoic acid (NG-02-100)

Red solid (66 mg, 70% yield).

Major Z-isomer data: $^1$H NMR (300 MHz, DMSO): δ 13.12 (brs, 1H, COOH), 8.65-8.59 (m, 2H), 8.54 (s, 1H), 8.19 (d, 1H, J=7.77 Hz), 8.01-7.92 (m, 2H), 7.82-7.73 (m, 2H), 7.69-7.65 (m, 1H), 7.60-7.54 (m, 2H), 3.90-3.81 (m, 2H, CH$_2$), 3.28-3.22 (m, 2H, CH$_2$), 3.19-3.13 (m, 2H, NHCH$_2$), 2.70 (s, 0.67H, minor isomer, CH$_3$), 2.34 (s, 2.33H, major isomer, CH$_3$), 1.84-1.72 (m, 1H, CH), 1.69-1.61 (m, 2H, CH$_2$), 1.30-1.14 (m, 2H, CH$_2$); $^{13}$C NMR (75 MHz, DMSO): δ 167.00, 165.75, 161.70, 157.56, 151.18, 150.29, 138.42, 138.18, 131.41, 130.93, 130.54, 129.66, 129.22, 127.47, 127.31, 126.60, 124.98, 121.79, 121.10, 118.45, 112.32, 66.72, 44.78, 34.77, 30.40, 12.80.

Synthesis of NG-01-72

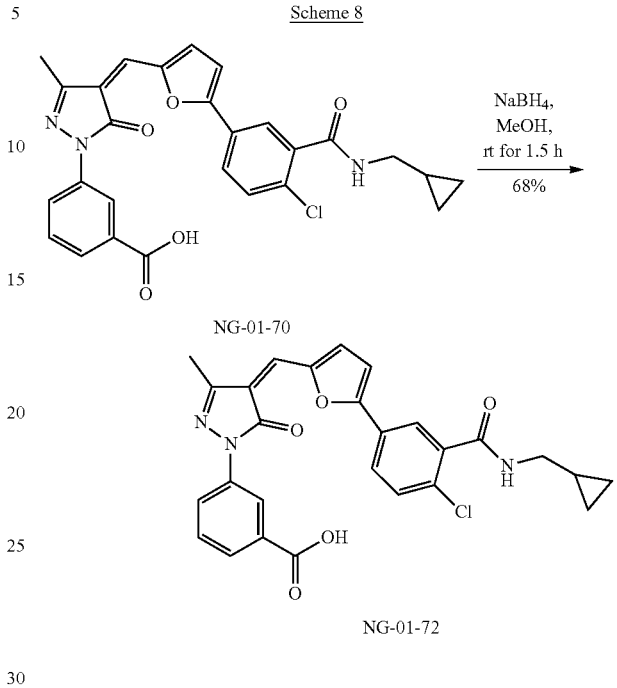

Scheme 8

3-(4-((5-(4-Chloro-3-((cyclopropylmethyl)carbamoyl)phenyl)furan-2-yl)methyl)-3-methyl-5-oxo-4,5-dihydro-1H-pyrazol-1-yl)benzoic acid (NG-01-72)

To a suspension of NG-01-70 (60 mg, 1 equiv.) in anhydrous methanol (5 mL) was added sodium borohydride (13 mg, 3 equiv.) in portions. During addition gas evolution was observed, and the color of the solution changed from dark red to yellowish orange. The resulting solution was stirred at room temperature for 1.5 h. Solvent was removed in vacuo and residue was acidified to pH 2-3 using 20% citric acid solution. The product was extracted with EtOAc (3×15 mL). The combined organic extracts was washed with brine, dried over Na$_2$SO$_4$ and concentrated under reduced pressure. The product was crystallized in EtOAc, solid was collected, washed with cold EtOAc and then hot solutions of 20-30% EtOAc in hexanes to afford NG-01-72 (41 mg, 68% yield) as a red solid.

3-(4-((5-(4-Chloro-3-((4-fluorobenzyl)carbamoyl) phenyl)furan-2-yl)methyl)-3-methyl-5-oxo-4,5-dihydro-1H-pyrazol-1-yl)benzoic acid (NG-01-65)

NG-01-65 was prepared from NG-01-64 according to the method described for preparing NG-01-72.

$^1$H NMR (500 MHz, DMSO): δ 8.95 (m, 1H), 8.56 (t, 1H), 8.17 (d, 1H), 8.02-7.95 (m, 2H), 7.73-7.69 (m, 2H), 7.65 (t, 1H), 7.52-7.49 (m, 2H), 7.41-7.38 (m, 2H), 7.17-7.13 (m, 2H), 4.47 (d, 2H, NHCH$_2$), 2.21 (brs, 3H).

3-(4-((5-(4-Chloro-3-((3-methoxyphenyl)carbamoyl) phenyl)furan-2-yl)methyl)-3-methyl-5-oxo-4,5-dihydro-1H-pyrazol-1-yl)benzoic acid (NG-02-132)

$^1$H NMR (300 MHz, DMSO): δ 13.12 (brs, 1H, COOH), 10.65.97 (s, 1H, NH), 8.69, 8.68 and 8.55 (m, 1H), 8.32 (s, 1H), 8.23-8.19 (m, 1H), 8.06-8.00 (m, 1H), 7.84-7.74 (m, 3H), 7.65-7.55 (m, 2H), 7.43 (brs, 1H), 7.29-7.27 (t, 2H), 6.75-6.71 (m, 1H), 3.76 (s, 3H), 2.12 (s, 3H).

(Z)-3-(4-((5-(((3-methoxyphenyl)carbamoyl)furan-2-yl)methylene)-3-methyl-5-oxo-4,5-dihydro-1H-pyrazol-1-yl)benzoic acid (NG-02-162)

NG-02-162 was made in a similar manner to procedure described in Example 1, except that 3-methoxyphenylboronic acid was used. $^1$H NMR (300 MHz, DMSO): δ 9.97 (brs, 1H, NH), 8.35 (s, 1H), 8.04-8.02 (s, 1H), 7.77-7.74 (m, 1H), 7.60-7.54 (t, 1H), 7.37-7.21 (m, 5H), 6.66-6.64 (m, 1H), 3.72 (s, 3H), 2.33 (s, 2.37H; major isomer, CH$_3$).

Preparation of Compounds NG-02-112 and NG-02-113

Compounds NG-02-112 and NG-02-113 were prepared using synthetic procedure described for the preparation of compound NG-01-64 using appropriate starting materials. Each compound was crystallized in EtOH, solid was collected, washed with EtOAc and then hot solutions of 20-30% EtOAc in hexanes to afford desired final compound.

(Z)-4-(4-((5-(4-(((Cyclopropylmethyl)carbamoyl)phenyl)furan-2-yl)methylene)-3-methyl-5-oxo-4,5-dihydro-1H-pyrazol-1-yl)benzoic acid (NG-02-112)

Red solid (94 mg, 67% yield).
Major Z-isomer data: $^1$H NMR (300 MHz, DMSO): δ 12.82 (s, 1H, COOH), 8.70-8.64 (m, 2H,), 8.09-7.79 (m, 8H), 7.73 (s, 1H), 7.57-7.53 (m, 1H), 3.15 (t, 2H, J=6.0 and 12.0 Hz, NHCH$_2$), 2.72 (s, 0.45H, minor isomer, CH$_3$), 2.33 (s, 2.55H, major isomer, CH$_3$), 1.09-0.97 (m, 1H, CH), 0.46-0.40 (m, 2H, CH$_2$), 0.26-0.21 (m, 2H, CH$_2$); $^{13}$C NMR (75 MHz, DMSO): δ 166.76, 165.09, 161.86, 158.55, 151.59, 150.27, 141.65, 135.21, 130.85, 130.44, 128.03, 125.87, 124.73, 120.71, 116.86, 112.45, 43.56, 12.79, 10.90, 3.27.

(Z)-4-(4-((5-(4-((4-Fluorobenzyl)carbamoyl)phenyl)furan-2-yl)methylene)-3-methyl-5-oxo-4,5-dihydro-1H-pyrazol-1-yl)benzoic acid (NG-02-113)

Red solid (109 mg, 77% yield).
Major Z-isomer data: $^1$H NMR (300 MHz, DMSO): δ 12.82 (s, 1H, COOH), 9.18 (t, 1H, J=5.7 and 11.64 Hz), 8.65 (d, 1H, J=3.45 Hz), 8.10-7.94 (m, 8H), 7.74 (s, 1H), 7.59-7.54 (m, 1H), 7.40-7.32 (m, 2H), 7.16 (t, 2H, J=8.85 and 17.67 Hz), 4.48 (d, 2H, J=5.55, NHCH$_2$), 2.73 (s, 0.64H, minor isomer, CH$_3$), 2.34 (s, 2.36H, major isomer, CH$_3$); $^{13}$C NMR (75 MHz, DMSO): 166.65, 165.14, 161.76, 158.36, 151.51, 150.21, 141.54, 135.53, 135.49, 130.56, 130.26, 129.14, 129.03, 128.00, 125.78, 124.70, 120.68, 116.77, 114.97, 114.68, 112.44, 41.83, 12.69.

(Z)-4-(4-((5-(4-Chloro-3-((3-methoxyphenyl)carbamoyl)phenyl)furan-2-yl)methylene)-3-methyl-5-oxo-4,5-dihydro-1H-pyrazol-1-yl)benzoic acid (NG-03-185)

Major Z-isomer data: $^1$H NMR (300 MHz, DMSO): δ 12.91 (brs, 1H, COOH), 10.55 (s, 1H, NH), 8.62 (brs, 1H), 8.10-7.87 (m, 7H), 7.81-7.78 (m, 1H), 7.70-7.68 (m, 1H), 7.60-7.56 (m, 1H), 7.45-7.41 (m, 1H), 7.28-7.24 (m, 2H), 6.72-6.69 (m, 1H). 3.74 (s, 3H), 2.74 (s, 0.22H; minor isomer, CH$_3$), 2.35 (s, 2.84H; major isomer, CH$_3$).

4-(4-((5-(4-Chloro-3-((3-methoxyphenyl)carbamoyl)phenyl)furan-2-yl)methyl)-3-methyl-5-oxo-4,5-dihydro-1H-pyrazol-1-yl)benzoic acid (NG-03-188)

$^1$H NMR (300 MHz, DMSO): δ 12.15 (brs, 1H, COOH), 10.67 (s, 1H, NH), 8.22-7.89 (m, 8H), 7.82-7.76 (m, 1H), 7.44 (brs, 1H), 7.30-7.26 (m, 2H), 6.74-6.71 (t, 1H), 3.78 (s, 3H), 2.10 (brs, 3H).

4-dimethoxyphenyl)carbamoyl)phenyl)furan-2-yl)methylene)-3-acid (NG-03-189)

Red solid (60 mg, 63% yield).
Major Z-isomer data: $^1$H NMR (300 MHz, DMSO): δ 13.14 (brs, 1H, COOH), 10.52 (s, 1H, NH), 8.70 (d, 1H, J=3.75 Hz), 8.56-8.51 (m, 1H), 8.28-8.18 (m, 2H), 8.08-8.04 (m, 1H), 7.80-7.74 (m, 3H), 7.65-7.55 (m, 2H), 7.45 (m, 1H), 7.30-7.27 (m, 2H), 6.97-6.90 (m, 1H), 3.75 and 3.74 (s, 3H, OCH$_3$), 2.74 (s, 0.49H; minor isomer, CH$_3$), 2.35 (s, 2.49H; major isomer, CH$_3$); $^{13}$C NMR (75 MHz, DMSO): δ 167.51, 164.22, 164.69, 162.22, 157.99, 151.70, 150.84, 149.00, 145.79, 138.93, 138.37, 131.93, 131.58, 130.46, 129.74, 127.94, 127.39, 125.73, 125.43, 122.30, 121.71, 118.96, 112.44, 111.98, 104.97, 105.83, 56.17, 55.84, 13.30. MS (ESI) m/z=584.1 [M–H]$^-$; HRMS (ESI): calcd for C$_{31}$H$_{23}$N$_3$O$_7$Cl [M–H]$^-$ m/z=584.1225, found 584.1236. HPLC purity: 95.07%.

(Z)-2-chloro-5-(5-(((1-(3-cyanophenyl)-3-methyl-5-oxo-1,5-dihydro-4H-pyrazol-4-ylidene)methyl)furan-2-yl)-N-(3-methoxyphenyl)benzamide (NG-03-193)

Major Z-isomer data: $^1$H NMR (300 MHz, DMSO): δ 10.65 (s, 1H, NH), 8.62 (brs, 1H), 8.30-8.16 (m, 2H), 7.74 (s, 1H), 7.31-7.25 (m, 2H), 6.72 (brs, 1H), 3.72 (s, 3H), 2.77 (s, 0.92H; minor isomer, CH$_3$), 2.32 (s, 2.08H; major isomer, CH$_3$).

(Z)-3-(4-((5-(4-chloro-3-((3-methoxyphenyl)carbamoyl)phenyl)thiophen-2-yl)methylene)-3-methyl-5-oxo-4,5-dihydro-1H-pyrazol-1-yl)benzoic acid (NG-03-203)

100% Z-isomer data: $^1$H NMR (300 MHz, DMSO): δ 10.63 (s, 1H, NH), 8.58 (t, 1H), 8.19-8.15 (m, 3H), 8.07-8.06 (d, 1H), 7.97-7.92 (m, 2H), 7.66-7.66 (dd, 2H), 7.58-7.53 (t, 1H), 7.44-7.43 (m, 1H), 7.29-7.27 (m, 2H), 6.74-6.70 (m, 1H), 3.75 (s, 3H), 2.34 (s, 3H); $^{13}$C NMR (75 MHz, DMSO): δ 168.61, 165.75, 163.60, 161.04, 154.90, 152.92, 146.05, 141.45, 139.91, 139.76, 139.21, 137.74, 133.33, 132.93, 132.34, 131.19, 130.86, 130.04, 127.75, 126.55, 123.25, 122.33, 119.76, 113.46, 110.99, 106.93, 56.56, 14.37.

3-(4-((5-(4-Chloro-3-((3,4-dimethoxyphenyl)carbamoyl)phenyl)furan-2-yl)methyl)-3-methyl-5-oxo-4,5-dihydro-1H-pyrazol-1-yl)benzoic acid (NG-03-206)

$^1$H NMR (300 MHz, DMSO): δ 10.43 (s, 1H, NH), 8.33-8.31 (m, 1H), 8.05-7.98 (m, 1H), 8.82-7.74 (m, 2H), 7.59-7.55 (m, 2H), 7.44-7.40 (m, 2H), 7.27-7.21 (m, 2H), 6.97-6.91 (m, 2H), 3.76 (s, 6H), 2.17 (s, 3H).

3-(4-((5-(4-chloro-3-((3-Methoxyphenyl)carbamoyl)phenyl)thiophen-2-yl)methyl)-3-methyl-5-oxo-4,5-dihydro-1H-pyrazol-1-yl)benzoic acid (NG-03-207)

$^1$H NMR (300 MHz, DMSO): δ 10.51 (s, 1H, NH), 8.33-8.30 (m, 1H), 8.04-7.98 (m, 1H), 8.77-7.73 (m, 2H), 7.66-7.64 (m, 1H), 7.56-7.51 (m, 3H), 7.45-7.39 (m, 2H), 7.26-7.23 (m, 2H), 6.72-6.69 (m, 1H), 3.74 (s, 3H), 2.15 (s, 3H).

(Z)-5-(5-(((1-(3-Carboxyphenyl)-3-methyl-5-oxo-1,5-dihydro-4H-pyrazol-4-ylidene)methyl)thiophen-2-yl)-2-chlorobenzoic acid (NG-03-224)

100% Z-isomer data: $^1$H NMR (300 MHz, DMSO): δ 14.15 (brs, 1H, COOH), 13.29 (brs, 1H, COOH), 8.33 (brs, 1H), 8.04-8.01 (d, 2H), 7.91-7.89 (m, 1H), 7.82-7.69 (m, 2H), 7.60-7.42 (m, 3H), 6.79 (brs, 1H), 2.36 (s, 3H, major isomer, CH$_3$).

(Z)-3-(4-((5-(4-Chloro-3-((cyclopropylmethyl)carbamoyl)phenyl)thiophen-2-yl)methylene)-3-methyl-5-oxo-4,5-dihydro-1H-pyrazol-1-yl)benzoic acid (NG-03-226)

100% Z-isomer data: $^1$H NMR (300 MHz, DMSO): δ 13.11 (brs, 1H, COOH), 8.63-8.54 (m, 1H), 8.39 (brs, 1H), 8.09-8.06 (d, 1H), 7.80-7.72 (m, 2H), 7.64-7.37 (m, 5H), 6.76-6.75 (brs, 1H), 3.16-3.09 (m, 2H, NHCH$_2$), 2.31 (s, 3H, major isomer, CH$_3$), 1.04-0.96 (m, 1H, CH), 0.45-0.40 (m, 2H, CH$_2$), 0.24-0.20 (m, 2H, CH$_2$).

(Z)-3-(4-((5-(4-Chloro-3-((4-fluorobenzyl)carbamoyl)phenyl)thiophen-2-yl)methylene)-3-methyl-5-oxo-4,5-dihydro-1H-pyrazol-1-yl)benzoic acid (NG-03-227)

100% Z-isomer data: $^1$H NMR (300 MHz, DMSO): δ 13.14 (brs, 1H, COOH), 9.18-9.14 (t, 1H), 8.59 (brs, 1H), 8.23-8.19 (m, 3H), 7.94-7.90 (m, 3H), 7.80-7.75 (d, 1H), 7.65-7.55 (m, 2H), 7.46-7.41 (m, 2H), 7.22-7.16 (t, 2H), 4.49-4.47 (d, 2H, NHCH$_2$), 2.36 (s, 3H, major isomer, CH$_3$).

3-(4-((5-(4-Chloro-3-((cyclopropylmethyl)carbamoyl)phenyl)thiophen-2-yl)methyl)-3-methyl-5-oxo-4,5-dihydro-1H-pyrazol-1-yl)benzoic acid (NG-03-231)

MS (ESI) m/z=520.1 [M–H]$^-$

3-(4-((5-(4-Chloro-3-((4-fluorobenzyl)carbamoyl)phenyl)thiophen-2-yl)methyl)-3-methyl-5-oxo-4,5-dihydro-1H-pyrazol-1-yl)benzoic acid (NG-03-232)

MS (ESI) m/z=574.1 [M–H]$^-$

(Z)-5-(5-(((1-(4-Carboxyphenyl)-3-methyl-5-oxo-1,5-dihydro-4H-pyrazol-4-ylidene)methyl)thiophen-2-yl)-2-chlorobenzoic acid (NG-03-234)

100% Z-isomer data: $^1$H NMR (300 MHz, DMSO): δ 14.11 (brs, 1H, COOH), 13.23 (brs, 1H, COOH), 8.20-8.00 (m, 3H), 7.95-7.88 (m, 3H), 7.74-7.70 (m, 1H), 7.53-7.42 (m, 2H), 2.35 (s, 3H, major isomer, CH$_3$).

(Z)-4-(4-((5-(4-Chloro-3-((3-methoxyphenyl)carbamoyl)phenyl)thiophen-2-yl)methylene)-3-methyl-5-oxo-4,5-dihydro-1H-pyrazol-1-yl)benzoic acid (NG-03-236)

100% Z-isomer data: $^1$H NMR (300 MHz, DMSO): δ 12.87 (brs, 1H, COOH), 10.64 (brs, 1H, NH), 8.21-8.16 (m, 2H), 8.14-7.90 (m, 7H), 7.74-7.68 (d, 1H), 7.46-7.41 (m, 1H), 7.29-7.24 (m, 2H), 6.74-6.70 (m, 1H), 3.76 (s, 3H), 2.35 (s, 3H, major isomer, CH$_3$).

(Z)-3-(4-((5-(3-(Benzylcarbamoyl)-4-chlorophenyl)furan-2-yl)methylene)-3-methyl-5-oxo-4,5-dihydro-1H-pyrazol-1-yl)benzoic acid (NG-03-270)

Major Z-isomer data: $^1$H NMR (300 MHz, DMSO): δ 13.17 (brs, 1H, COOH), 9.07 (t, 1H), 8.33 (brs, 1H), 8.04-8.01 (d, 1H), 7.80-7.25 (m, 12H), 6.99-6.98 (d, 1H), 4.45-4.43 (d, 2H), 2.70 (s, 0.70H; minor isomer, CH$_3$), 2.29 (s, 2.43H; major isomer, CH$_3$).

(Z)-3-(4-((5-(4-chloro-3-((2-chlorobenzyl)carbamoyl)phenyl)furan-2-yl)methylene)-3-methyl-5-oxo-4,5-dihydro-1H-pyrazol-1-yl)benzoic acid (NG-03-271)

Major Z-isomer data: $^1$H NMR (300 MHz, DMSO): δ 13.14 (brs, 1H, COOH), 9.12-9.09 (m, 1H), 8.32 (brs, 1H), 8.03-8.00 (d, 1H), 7.95-7.78 (m, 2H), 7.70-7.30 (m, 9H), 7.06-6.99 (m, 1H), 4.51-4.49 (d, 2H), 2.71 (s, 0.52H; minor isomer, CH$_3$), 2.36 (s, 2.49H; major isomer, CH$_3$).

(Z)-4-(4-((5-(4-Chloro-3-((3-methoxybenzyl)carbamoyl)phenyl)furan-2-yl)methylene)-3-methyl-5-oxo-4,5-dihydro-1H-pyrazol-1-yl)benzoic acid (NG-04-286)

Major Z-isomer data: $^1$H NMR (300 MHz, DMSO): δ 12.87 (brs, 1H, COOH), 9.16-9.12 (t, 1H), 8.64 and 8.63 (d, 1H), 8.14-7.92 (m, 5H), 7.82-7.78 (m, 1H), 7.71-7.68 (d, 1H), 7.68-7.53 (m, 2H), 7.35-7.24 (m, 1H), 6.97-6.96 (brs, 2H), 6.88-6.82 (m, 1H), 4.49-4.47 (d, 2H), 3.75 (s, 3H), 2.67 (s, 0.77H; minor isomer, CH$_3$), 2.34 (s, 2.26H; major isomer, CH$_3$).

Scheme 7

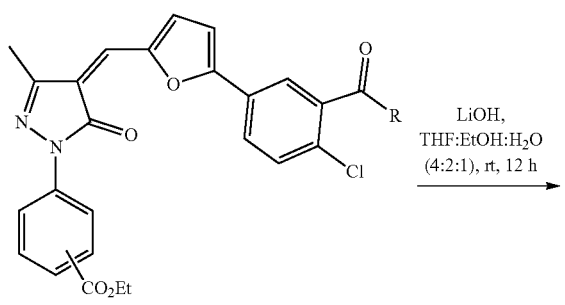

10-19

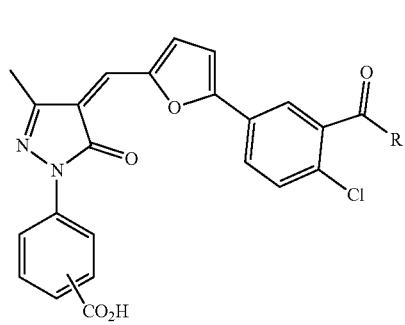

m-COOH = NG-01-64, NG-01-68,
NG-01-70, NG-01-78, NG-01-81,
NG-01-82, NG-01-99, NG-01-100
p-COOH = NG-01-91, NG-01-92,

Synthesis of (Z)-3-(4-((5-(4-Chloro-3-((4-fluorobenzyl)carbamoyl)phenyl)furan-2-yl)methylene)-3-methyl-5-oxo-4,5-dihydro-1H-pyrazol-1-yl)benzoic acid (NG-01-64)

To a stirred suspension of ester 10 (80 mg, 1 equiv.) in THF:EtOH:H₂O (4:2:1, 7 mL) was added LiOH (32 mg, 10 equiv.). The reaction mixture was stirred at room temperature for 12 h. Solvent was removed in vacuo and residue was acidified to pH 2-3 using 20% citric acid solution. The product was extracted with EtOAc (3×15 mL). The combined organic extracts was washed with brine, dried over Na₂SO₄ and concentrated under reduced pressure. The product was crystallized in EtOH, solid was collected, washed with EtOAc and then hot solutions of 20-30% EtOAc in hexanes to afford NG-01-64 (47 mg, 62% yield) as a red solid.

Major Z-isomer data: ¹H NMR (500 MHz, DMSO): δ 9.15 (t, 1H, J=5.8 and 11.7 Hz), 8.68 (d, 1H, J=3.05 Hz), 8.56 (t, 1H, J=1.7 and 3.85 Hz), 8.20 (d, 1H, J=7.45 Hz), 8.04-7.94 (m, 2H), 7.82-7.69 (m, 2H), 7.71 (t, 1H, J=8.15 and 16.45 Hz), 7.62-7.55 (m, 2H), 7.45-7.42 (m, 2H), 7.22-7.17 (m, 2H), 4.49 (d, 2H, J=5.85 Hz, NHCH₂), 2.68 (s, 0.76H, CH₃), 2.36 (s, 2.24H, CH₃).

Compounds NG-01-68, was synthesized by an above synthetic procedure described for the preparation of compound NG-01-64 using appropriate starting materials.

(Z)-3-(4-((5-(4-Chloro-3-((3-methoxyphenyl)carbamoyl)phenyl)furan-2-yl)methylene)-3-methyl-5-oxo-4,5-dihydro-1H-pyrazol-1-yl)benzoic acid (NG-01-68)

Red solid (111 mg, 69% yield). Major Z-isomer data: ¹H NMR (300 MHz, DMSO): δ 13.04 (brs, 1H, COOH), 10.65 (s, 1H, NH), 8.69 (d, 1H, J=3.16 Hz), 8.55 (t, 1H, J=1.95 and 3.5 Hz), 8.31-8.19 (m, 2H), 8.08-7.97 (m, 1H), 7.80-7.70 (m, 3H), 7.65-7.55 (m, 2H), 7.43 (s, 1H), 7.29-7.28 (m, 2H), 6.74-6.69 (m, 1H), 3.76 (s, 3H, OCH₃), 2.73 (s, 0.51H, minor isomer, CH₃), 2.34 (s, 2.49H, major isomer, CH₃); ¹³C NMR (75 MHz, DMSO): δ 172.50, 167.51, 167.28, 165.08, 164.69, 162.22, 160.01, 157.94, 151.59, 140.41, 138.93, 123.24, 132.03, 131.93, 131.22, 130.72, 129.72, 129.47, 125.48, 124.69, 122.30, 121.74, 112.32, 109.89, 105.83, 55.52, 13.30.

Scheme 2. Synthesis of Analogs 39a-dᵃ

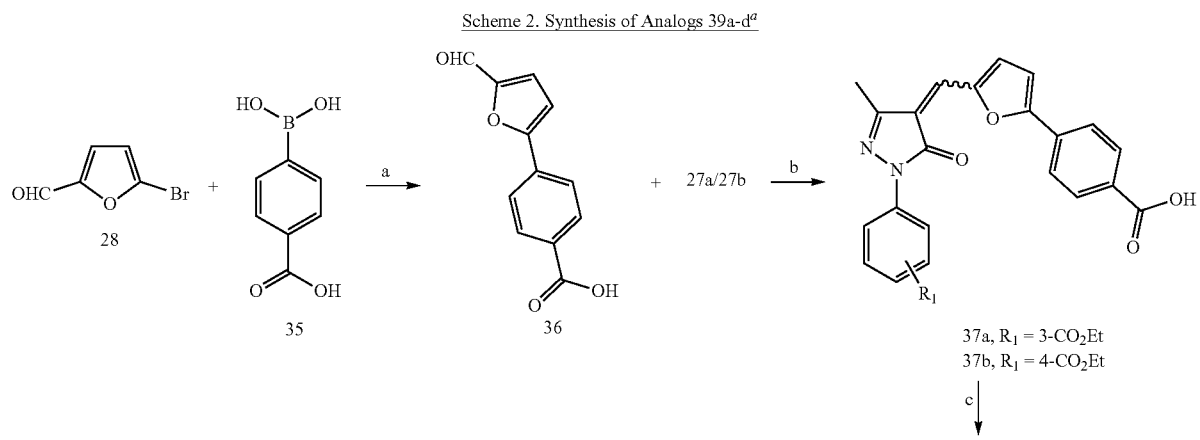

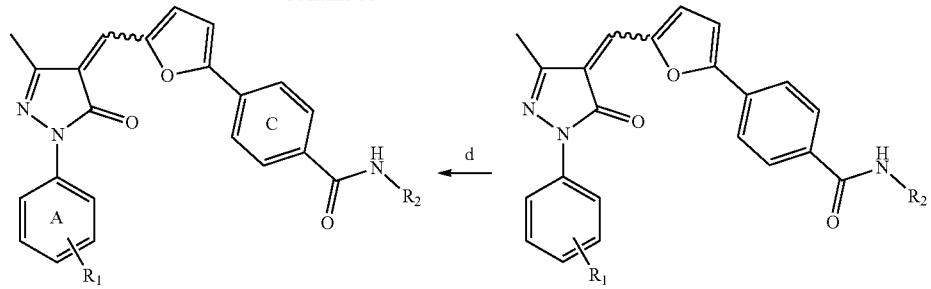

39a, $R_1$ = 3-$CO_2H$; $R_2$ = 4-fluorobenzyl
39b, $R_1$ = 3-$CO_2H$; $R_2$ = cyclopropylmethyl
39c, $R_1$ = 4-$CO_2H$; $R_2$ = 4-fluorobenzyl
39d, $R_1$ = 4-$CO_2H$; $R_2$ = cyclopropylmethyl 38a, $R_1$ = 3-$CO_2Et$; $R_2$ = 4-fluorobenzyl
38b, $R_1$ = 3-$CO_2Et$; $R_2$ = cyclopropylmethyl
38c, $R_1$ = 4-$CO_2Et$; $R_2$ = 4-fluorobenzyl
38d, $R_1$ = 4-$CO_2Et$; $R_2$ = cyclopropylmethyl

[a]Reagents and conditions: (a) Pd(PPh$_3$)$_4$, K$_2$CO$_3$, toluene:EtOH:H$_2$O (1:1:0.3), 90° C. for 15 h, 90%; (b) AcOH, reflux for 3 h, 78-85%; (c) alkyl or aryl amine, EDCI, HOBt, DIPEA, DMF, rt for 18 h, 74-80%; (d) LiOH, THF:EtOH:H$_2$O (4:2:1), rt for 12 h, 64-77% (after recrystallization).

Synthesis of 4-(5-Formylfuran-2-yl)benzoic acid (36)

Aldehyde 36 was synthesized using the Suzuki coupling reaction described for the preparation of compound 30 using 4-carboxyphenylboronic acid 35 as a starting material. The workup of this reaction was different from previous reaction as the product was insoluble in organic solvents after acidification. The reaction mixture was cooled to room temperature and the solvent was removed under reduced pressure. The pH of the suspension was adjusted to 1-2 by the addition of 6N HCl solution. The precipitated product was filtered, washed successively with water (3×15 mL), EtOAc (2×10 mL), DCM and dried under high vacuum overnight to get 4-(5-formylfuran-2-yl)benzoic acid 36 (1.11 gm, 90% yield) as a white solid. $^1$H NMR (500 MHz, DMSO): δ 13.16 (s, 1H, COOH), 9.66 (s, 1H, CHO), 8.05 (dd, 2H, J=1.5 and 6.5 Hz), 8.00 (dd, 2H, J=2.0 and 7.0 Hz), 7.70 (d, 1H, J=3.5 Hz), 7.46 (d, 1H, J=4.0 Hz); $^{13}$C NMR (125 MHz, DMSO): δ 178.70, 167.17, 157.36, 152.66, 132.78, 131.73, 130.61, 125.47, 111.05. MS (ESI) m/z=215.1 [M−H]$^−$. HRMS (ESI): calcd for $C_{12}H_7O_4$ [M−H]$^−$ m/z=215.0344, found 215.0351.

Synthesis of compounds 37a and 37b. 37a and 37b were prepared using an above Knoevenagel condensation reaction procedure described for the preparation of compound 31a using 4-(5-formylfuran-2-yl)benzoic acid 28 and 27a (600 mg) and 27b (600 mg), respectively as starting materials.

(Z)-4-(5-((1-(3-(Ethoxycarbonyl)phenyl)-3-methyl-5-oxo-1H-pyrazol-4(5H)-ylidene)methyl)furan-2-yl)benzoic acid (37a)

Red solid (844 mg, 78% yield). Major Z-isomer data: $^1$H NMR (500 MHz, DMSO): δ 13.14 (s, 1H, COOH), 8.63 (d, 1H, J=3.5 Hz); 8.49 (t, 1H, J=1.5 and 3.5 Hz), 8.20 (d, 1H, J=8.5 Hz), 8.03-7.90 (m, 4H), 7.76-7.71 (m, 1H), 7.65 (s, 1H), 7.56-7.51 (m, 2H), 4.35-4.29 (q, 2H, OCH$_2$), 2.67 (s, 0.68H; minor isomer, CH$_3$), 2.32 (s, 2.32H; major isomer, CH$_3$), 1.34 (t, 3H, J=7.5 and 14.5 Hz, CH$_3$); $^{13}$C NMR (125 MHz, DMSO): 166.62, 165.40, 161.60, 158.05, 151.10, 150.51, 138.48, 133.15, 131.98, 131.25, 130.09, 129.45, 129.29, 127.32, 124.91, 124.70, 121.27, 118.02, 112.91, 60.88, 14.15, 12.78. MS (ESI) m/z=443.1 [M−H]$^−$; HRMS (ESI): calcd for $C_{25}H_{19}N_2O_6$ [M−H]$^−$ m/z=443.1243, found 443.1254.

(Z)-4-(5-((1-(4-(Ethoxycarbonyl)phenyl)-3-methyl-5-oxo-1H-pyrazol-4(5H)-ylidene)methyl)furan-2-yl)benzoic acid (37b)

Red solid (920 mg, 85% yield). Major Z-isomer data: $^1$H NMR (300 MHz, DMSO): δ 13.08 (brs, 1H, COOH), 8.56 (s, 1H), 7.98-7.81 (m, 7H), 7.62-7.39 (m, 3H), 4.27-4.20 (q, 2H, OCH$_2$), 2.59 (s, 0.68H; minor isomer, CH$_3$), 2.28 (s, 2.32H; major isomer, CH$_3$), 1.28 (t, 3H, J=6.63 and 12.57 Hz, CH$_3$). MS (ESI) m/z=443.1 [M−H]$^−$; HRMS (ESI): calcd for $C_{25}H_{19}N_2O_6$ [M−H]$^−$ m/z=443.1243, found 443.1249.

Synthesis of Amides 38a-d

Compounds 38a-b and 38c-d were prepared using an above synthetic procedure described for the preparation of compound 33a using 37a (300 mg) and 37b (300 mg), respectively and corresponding amines as a starting material.

(Z)-Ethyl 3-(4-((5-(4-((4-fluorobenzyl)carbamoyl)phenyl)furan-2-yl)methylene)-3-methyl-5-oxo-4,5-dihydro-1H-pyrazol-1-yl)benzoate (38a)

Red solid (294 mg, 79% yield). Major Z-isomer data: $^1$H NMR (300 MHz, DMSO): δ 9.29 (t, 1H, J=5.7 and 11.7 Hz), 8.64 (d, 1H, J=3.72 Hz), 8.56-8.47 (m, 1H), 8.21 (d, 1H, J=8.1 Hz), 8.06-7.86 (m, 4H), 7.76-7.61 (m, 2H), 7.57-7.44 (m, 2H), 7.42-7.32 (m, 2H), 7.20-7.12 (m, 2H), 4.45 (d, 2H, J=5.67 Hz, NHCH$_2$), 4.36-4.27 (q, 2H, OCH$_2$), 2.67 (s, 0.49H; minor isomer, CH$_3$), 2.32 (s, 2.51H; major isomer, CH$_3$), 1.35-1.29 (m, 3H, CH$_3$); $^{13}$C NMR (75 MHz, DMSO): δ 166.59, 166.05, 162.49, 159.25, 158.43, 151.15, 150.67, 147.18, 139.31, 136.55, 135.55, 132.60, 131.50, 131.28, 130.89, 130.04 129.94, 129.01, 128.69, 128.34, 125.75, 125.61, 122.86, 121.76, 119.92, 118.85, 115.84, 115.75, 113.36, 61.70 (d), 42.74, 14.99, 13.76 (d). MS (ESI) m/z=552.1 [M+H]$^+$; HRMS (ESI): calcd for $C_{32}H_{27}N_3O_5F$ [M+H]$^+$ m/z=552.1935, found 552.1939.

(Z)-Ethyl 3-(4-((5-(4-((cyclopropylmethyl)carbamoyl)phenyl)furan-2-yl)methylene)-3-methyl-5-oxo-4,5-dihydro-1H-pyrazol-1-yl)benzoate (38b)

Red solid (248 mg, 74% yield). Major Z-isomer data: $^1$H NMR (300 MHz, DMSO): δ 8.71-8.64 (m, 2H), 8.52 (t, 1H, J=1.8 and 3.6 Hz), 8.21 (d, 1H, J=8.22 Hz), 8.03-7.91 (m, 4H), 7.78-7.70 (m, 2H), 7.59-7.50 (m, 2H), 4.37-4.28 (q, 2H, OCH$_2$), 3.16 (t, 2H, J=6.21 and 12.36 Hz, NHCH$_2$), 2.70 (s, 0.71H; minor isomer, CH$_3$), 2.34 (s, 2.29H; major isomer, CH$_3$), 1.36-1.30 (m, 3H, CH$_3$), 1.08-0.98 (m, 1H, CH), 0.47-0.41 (m, 2H, CH$_2$), 0.26-0.21 (m, 2H, CH$_2$); $^{13}$C NMR (75 MHz, DMSO): δ 165.91, 165.64, 165.01, 162.18, 159.00, 151.69, 150.82, 139.02, 138.84, 135.64, 131.01, 130.97, 130.09, 129.83, 128.56, 128.04, 127.00, 125.25, 122.53, 121.43, 118.53, 112.96, 61.40, 44.11, 14.66, 13.31, 11.46, 3.83. MS (ESI) m/z=498.1 [M+]$^+$; HRMS (ESI): calcd for C$_{29}$H$_{28}$N$_3$O$_5$ [M+H]$^+$ m/z=498.2029, found 498.2030.

(Z)-Ethyl 4-(4-((5-(4-((4-fluorobenzyl)carbamoyl)phenyl)furan-2-yl)methylene)-3-methyl-5-oxo-4,5-dihydro-1H-pyrazol-1-yl)benzoate (38c)

Red solid (297 mg, 80% yield). Major Z-isomer data: $^1$H NMR (300 MHz, DMSO): δ 9.20 (m, 1H), 8.64 (d, 1H, J=3.84 Hz), 8.11-7.92 (m, 8H), 7.73 (d, 1H, J=11.7 Hz), 7.58-7.49 (m, 1H), 7.40-7.31 (m, 2H), 7.19-7.09 (m, 2H), 4.48-4.42 (q, 2H, NHCH$_2$), 4.32-4.21 (m, 2H, OCH$_2$), 2.66 (s, 0.56H; minor isomer, CH$_3$), 2.34 (s, 2.44H; major isomer, CH$_3$), 1.33-1.25 (m, 3H, CH$_3$). MS (ESI) m/z=552.1 [M+H]$^+$; HRMS (ESI): calcd for C$_{32}$H$_{27}$N$_3$O$_5$F [M+H]$^+$ m/z=552.1935, found 552.1943.

(Z)-Ethyl 4-(4-((5-(4-((cyclopropylmethyl)carbamoyl)phenyl)furan-2-yl)methylene)-3-methyl-5-oxo-4,5-dihydro-1H-pyrazol-1-yl)benzoate (38d)

Red solid (251 mg, 75% yield). Major Z-isomer data: $^1$H NMR (300 MHz, DMSO): δ 8.69 (t, 1H, J=5.58 and 11.55 Hz), 8.63 (d, 1H, J=3.66 Hz), 8.09-7.90 (m, 8H), 7.70 (s, 1H), 7.56-7.50 (m, 1H), 4.31-4.22 (q, 2H, OCH$_2$), 3.15 (t, 2H, J=5.7 and 12.0 Hz, NHCH$_2$), 2.68 (s, 0.70H; minor isomer, CH$_3$), 2.33 (s, 2.30H; major isomer, CH$_3$), 1.33-127 (m, 3H, CH$_3$), 1.08-0.99 (m, 1H, CH), 0.47-0.41 (m, 2H, CH$_2$), 0.26-0.21 (m, 2H, CH$_2$). MS (ESI) m/z=498.1 [M+H]$^+$; HRMS (ESI): calcd for C$_{29}$H$_{28}$N$_3$O$_5$ [M+H]$^+$ m/z=498.2029, found 498.2034.

Synthesis of Target Compounds 39a-d

Target Compounds 39a-d were synthesized by an above synthetic procedure described for the preparation of compound 34a using appropriate starting materials. Each compound was crystallized in EtOH, solid was collected, washed with EtOAc and then hot solutions of 20-30% EtOAc in hexanes to afford the desired final compound. If necessary, the products were purified using 2-5% MeOH in DCM (1% AcOH in DCM) solvent system on automated flash column chromatography.

(Z)-3-(4-((5-(4-((4-Fluorobenzyl)carbamoyl)phenyl)furan-2-yl)methylene)-3-methyl-5-oxo-4,5-dihydro-1H-pyrazol-1-yl)benzoic acid (39a)

Red solid (103 mg, 73% yield). Major Z-isomer data: $^1$H NMR (300 MHz, DMSO): δ 13.12 (s, 1H, COOH), 9.20-9.16 (m, 1H), 8.69 (d, 1H, J=3.84 Hz), 8.55 (t, 1H, J=1.83 and 3.6 Hz, major isomer), 8.21 (d, 1H, J=8.16 Hz), 8.08-7.98 (m, 4H), 7.83-7.73 (m, 2H), 7.60-7.53 (m, 2H), 7.40-7.35 (m, 2H), 7.16 (t, 2H, J=8.94 and 17.82 Hz), 4.48 (d, 2H, J=5.79 Hz, NHCH$_2$), 2.75 (s, 1.06H; minor isomer, CH$_3$), 2.35 (s, 1.94H; major isomer, CH$_3$); $^{13}$C NMR (75 MHz, DMSO): δ 167.03, 165.34, 162.76, 161.74, 159.56, 158.43, 149.97, 148.23, 138.46, 135.68, 134.79, 131.44, 130.79, 129.32, 129.22, 128.19, 127.51, 125.04, 124.87, 121.82, 121.13, 119.46, 118.47, 115.15, 114.87, 112.60, 42.01, 12.84. MS (ESI) m/z=522.1 [M−H]$^-$; HRMS (ESI): calcd for C$_{30}$H$_{21}$N$_3$O$_5$F [M−H]$^-$ m/z=522.1465, found 522.1467. HPLC purity: 97.73%.

(Z)-3-(4-((5-(4-((Cyclopropylmethyl)carbamoyl)phenyl)furan-2-yl)methylene)-3-methyl-5-oxo-4,5-dihydro-1H-pyrazol-1-yl)benzoic acid (39b)

Red solid (90 mg, 64% yield). Isomer data: $^1$H NMR (300 MHz, DMSO): δ 13.11 (s, 1H, COOH), 8.72-8.65 (m, 2H), 8.55 (d, 1H, J=14.52 Hz), 8.19 (d, 1H, J=6.15 Hz), 8.05-7.92 (m, 4H), 7.82-7.70 (m, 2H), 7.59-7.51 (m, 2H), 3.16 (t, 2H, J=6.35 and 12.28 Hz, NHCH$_2$), 2.73 (s, 1.65H, CH$_3$), 2.34 (s, 1.35H, CH$_3$), 1.09-0.97 (m, 1H, CH), 0.48-0.40 (m, 2H, CH$_2$), 0.27-0.20 (m, 2H, CH$_2$); $^{13}$C NMR (75 MHz, DMSO): 167.07, 165.22, 161.75, 159.93, 158.54, 151.20, 150.41, 138.49, 138.33, 135.20, 131.45, 130.77, 130.60, 129.65, 129.25, 128.14, 127.56, 124.99, 124.82, 121.82, 121.09, 118.48, 112.52, 112.29, 43.67, 12.87, 11.02, 3.39. MS (ESI) m/z=568.1 [M−H]$^-$; HRMS (ESI): calcd for C$_{27}$H$_{22}$N$_3$O$_5$ [M−H]$^-$ m/z=468.1559, found 468.1561. HPLC purity: 96.48%.

(Z)-4-(4-((5-(4-((4-Fluorobenzyl)carbamoyl)phenyl)furan-2-yl)methylene)-3-methyl-5-oxo-4,5-dihydro-1H-pyrazol-1-yl)benzoic acid (39c)

Red solid (109 mg, 77% yield). Major Z-isomer data: $^1$H NMR (300 MHz, DMSO): δ 12.82 (s, 1H, COOH), 9.18 (t, 1H, J=5.7 and 11.64 Hz), 8.65 (d, 1H, J=3.45 Hz), 8.10-7.94 (m, 8H), 7.74 (s, 1H), 7.59-7.54 (m, 1H), 7.40-7.32 (m, 2H), 7.16 (t, 2H, J=8.85 and 17.67 Hz), 4.48 (d, 2H, J=5.55, NHCH$_2$), 2.73 (s, 0.64H; minor isomer, CH$_3$), 2.34 (s, 2.36H; major isomer, CH$_3$); $^{13}$C NMR (75 MHz, DMSO): δ 166.65, 165.14, 161.76, 158.36, 151.51, 150.21, 141.54, 135.53, 135.49, 130.56, 130.26, 129.14, 129.03, 128.00, 125.78, 124.70, 120.68, 116.77, 114.97, 114.68, 112.44, 41.83, 12.69. MS (ESI) m/z=522.1 [M−H]$^-$; HRMS (ESI): calcd for C$_{30}$H$_{21}$N$_3$O$_5$F [M−H]$^-$ m/z=522.1465, found 522.1465. HPLC purity: 98.52%.

(Z)-4-(4-((5-(4-((Cyclopropylmethyl)carbamoyl)phenyl)furan-2-yl)methylene)-3-methyl-5-oxo-4,5-dihydro-1H-pyrazol-1-yl)benzoic acid (39d)

Red solid (94 mg, 67% yield). Major Z-isomer data: $^1$H NMR (300 MHz, DMSO): δ 12.82 (s, 1H, COOH), 8.70-8.64 (m, 2H,), 8.09-7.79 (m, 8H), 7.73 (s, 1H), 7.57-7.53 (m, 1H), 3.15 (t, 2H, J=6.0 and 12.0 Hz, NHCH$_2$), 2.72 (s, 0.45H; minor isomer, CH$_3$), 2.33 (s, 2.55H; major isomer, CH$_3$), 1.09-0.97 (m, 1H, CH), 0.46-0.40 (m, 2H, CH$_2$), 0.26-0.21 (m, 2H, CH$_2$); $^{13}$C NMR (75 MHz, DMSO): δ 166.76, 165.09, 161.86, 158.55, 151.59, 150.27, 141.65, 135.21, 130.85, 130.44, 128.03, 125.87, 124.73, 120.71, 116.86, 112.45, 43.56, 12.79, 10.90, 3.27 MS (ESI) m/z=568.1 [M−H]$^-$; HRMS (ESI): calcd for C$_{27}$H$_{22}$N$_3$O$_5$ [M−H]$^-$ m/z=468.1559, found 468.1557. HPLC purity: 95.37%.

Synthesis of 5-((1-(3-(ethoxycarbonyl)phenyl)-3-methyl-5-oxo-1,5-dihydro-4H-pyrazol-4-ylidene)methyl)furan-2-carboxylic acid (NG-02-154)

Compound NG-02-154 were synthesized by an above synthetic procedure described for the preparation of compound 31a using ethyl 3-(3-methyl-5-oxo-4,5-dihydro-1H-pyrazol-1-yl)benzoate 27a (500 mg) and 5-formylfuran-2-carboxylic acid starting materials. Red solid, (658 mg, 88% yield). Major isomer data: $^1$H NMR (300 MHz, DMSO): δ 13.83 (brs, 1H, COOH), 8.58 (d, 1H, J=3.9 Hz), 8.50 (t, 1H, J=1.8 and 3.6 Hz), 8.19 (d, 1H, J=7.2 Hz), 7.79-7.75 (m, 2H), 7.58 (t, 1H, J=8.1 and 15.9 Hz), 7.49 (d, 1H, J=4.5 Hz), 4.38-4.30 (q, 2H, OCH$_2$), 2.62 (s, 0.19H; minor isomer, CH$_3$), 2.34 (s, 2.81H; major isomer, CH$_3$), 1.36 (t, 3H, J=7.17 and 13.92 Hz).

Synthesis of compound 3-(4-((5-(4-chloro-3-((cyclohexylmethyl)carbamoyl)phenyl)furan-2-yl)methylene)-3-methyl-5-oxo-4,5-dihydro-1H-pyrazol-1-yl)benzoic acid (NG-04-274)

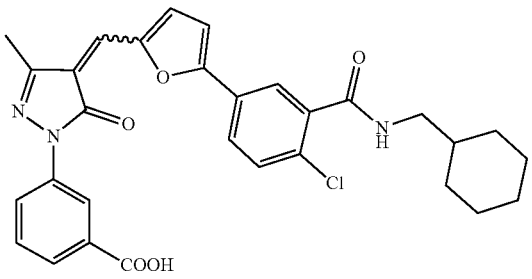

NG-04-274

Compound NG-04-274 was synthesized by an above hydrolysis protocol described for the preparation of compound 34a using corresponding ester (60 mg) as a starting material. Red solid, (40 mg, 70% yield). Major isomer data: $^1$H NMR (300 MHz, DMSO): δ 13.13 (brs, 1H, COOH), 8.67 (s, 1H), 8.59-8.47 (m, 2H), 8.21 (d, 1H, J=8.16 Hz), 8.04-7.92 (m, 2H), 7.83-7.74 (m, 2H), 7.71-7.66 (m, 1H), 7.62-7.54 (m, 2H), 3.10 (t, 2H, J=6.24 and 12.42 Hz), 2.72 (s, 0.61H; minor isomer, CH$_3$), 2.35 (s, 2.39H; major isomer, CH$_3$), 1.79-1.63 (m, 5H), 1.23-1.18 (m, 3H), 1.01-0.93 (m, 2H); $^{13}$C NMR (75 MHz, DMSO): δ 167.50, 166.12, 162.22, 158.11, 151.71, 150.79, 138.93, 138.81, 131.92, 131.47, 131.03, 129.74, 127.79, 127.04, 125.43, 122.31, 121.60, 118.96, 112.83, 45.84, 45.74, 37.83, 30.92, 26.51, 25.89, 13.33.

Synthesis of Compounds NG-02-150, NG-02-151, NG-03-238 and NG-03-294

Compounds NG-02-150, NG-02-151, NG-03-238 and NG-03-294 were synthesized by an above synthetic procedure described for the preparation of compound NG-01-72 using corresponding starting material.

4-(4-((5-(4-Chloro-3-((cyclopropylmethyl)carbamoyl)phenyl)furan-2-yl)methyl)-3-methyl-5-oxo-4,5-dihydro-1H-pyrazol-1-yl)benzoic acid (NG-02-150)

Red solid (80 mg, 81% yield). $^1$H NMR (300 MHz, DMSO): δ 12.85 (brs, 1H, COOH), 8.69 (t, 1H, J=5.2 and 10.4 Hz), 8.06-8.03 (m, 2H), 7.98 (d, 4H, J=8.4 Hz), 7.73 (s, 1H), 7.69-7.65 (m, 1H), 7.55 (d, 1H, J=3.9 Hz), 3.19 (t, 2H, NHCH$_2$), 2-75-2.64 (q, 2H), 1.06-0.91 (m, 1H, CH), 0.46-0.39 (m, 2H, CH$_2$), 0.30-0.25 (m, 2H, CH$_2$).

4-(4-((5-(4-Chloro-3-((4-fluorobenzyl)carbamoyl)phenyl)furan-2-yl)methyl)-3-methyl-5-oxo-4,5-dihydro-1H-pyrazol-1-yl)benzoic acid (NG-02-151)

Red solid (74 mg, 75% yield). $^1$H NMR (300 MHz, DMSO): δ 12.81 (brs, 1H, COOH), 9.14 (s, 1H), 8.08-7.95 (m, 5H), 7.80-7.77 (m, 1H), 7.70-7.66 (m, 1H), 7.60-7.55 (m, 2H), 7.43-7.39 (m, 2H), 7.19-7.16 (m, 2H), 4.47 (s, 2H, NHCH$_2$), 2-79-2.63 (q, 2H).

4-(4-((5-(4-Chloro-3-((3-methoxyphenyl)carbamoyl)phenyl)thiophen-2-yl)methyl)-3-methyl-5-oxo-4,5-dihydro-1H-pyrazol-1-yl)benzoic acid (NG-03-238)

Red solid (68 mg, 69% yield). $^1$H NMR (300 MHz, DMSO): δ 12.88 (brs, 1H, COOH), 10.53 (brs, 1H, NH), 8.03-7.98 (m, 2H), 7.95-7.89 (t, 2H), 7.76 (s, 1H), 7.68-7.64 (m, 1H), 7.54-7.51 (d, 1H), 7.47-7.46 (dd, 1H), 7.41 (brs, 1H), 7.26-7.21 (m, 2H), 6.91-6.90 (d, 1H), 6.71-6.67 (m, 1H), 3.74 (s, 3H), 2-76-2.65 (q, 2H).

4-(4-((5-(4-chloro-3-((3-methoxybenzyl)carbamoyl)phenyl)furan-2-yl)methyl)-3-methyl-5-oxo-4,5-dihydro-1H-pyrazol-1-yl)benzoic acid (NG-04-294)

Red solid (41 mg, 68% yield). $^1$H NMR (300 MHz, DMSO): δ 12.80 (brs, 1H, COOH), 9.14 (t, 1H), 8.16-7.85 (m, 5H), 7.68-7.53 (m, 2H), 7.32-7.25 (m, 2H), 6.97-6.95-6.83 (m, 4H), 4.47 (s, 2H), 3.75 (s, 3H), 2-72-2.69 (q, 2H).

Scheme X$^a$. Synthesis of compound NG-03-201/244 and NG-03-205/245.

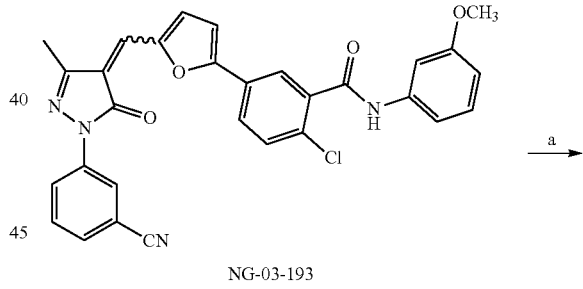

NG-03-193

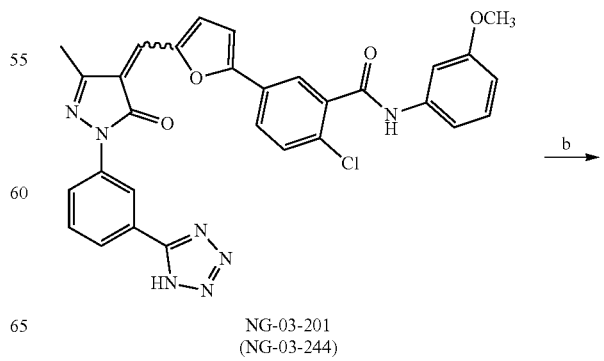

NG-03-201
(NG-03-244)

-continued

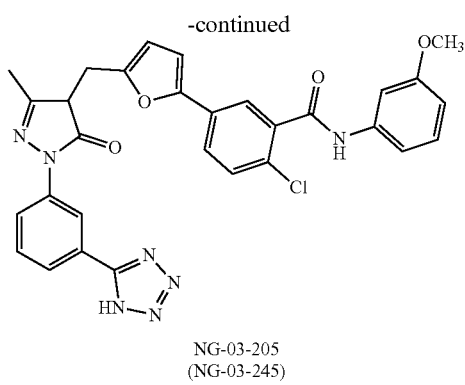

NG-03-205
(NG-03-245)

<sup>a</sup>Reagents and conditions: (a) NaN₃, NH₄Cl, DMF, 130° C. for 24 h, 64%; (b) NaBH₄, MeOH, 0° C. to rt for 1.5 h, 70%.

(Z)-5-(5-((1-(3-(1H-Tetrazol-5-yl)phenyl)-3-methyl-5-oxo-1,5-dihydro-4H-pyrazol-4-ylidene)methyl)furan-2-yl)-2-chloro-N-(3-methoxyphenyl)benzamide (NG-03-201/244)

To a solution of nitrile NG-03-193 (200 mg, 1 equiv.) in anhydrous DMF (10 mL) was added sodium azide (72 mg, 3 equiv.) and then NH₄Cl (60 mg, 3 equiv.). The reaction mixture was heated at 130° C. for 24 h. After cooling the reaction mixture, it was poured into 50-60 mL cold water and then acidified with 1N HCl to pH ~2. The precipitated solid was collected by filtration, washed with water 2-3 times. The crude product was crystallized in EtOH/EtOAc mixture (1:9), solid was collected, washed with EtOAc and then hot solutions of 20-30% EtOAc in hexanes to afford tetrazole NG-03-201/244 (138 mg, 64% yield) as a red solid. Major Z-isomer data: ¹H NMR (300 MHz, DMSO): δ 10.66 (s, 1H, NH), 8.64 and 8.62 (d, 1H), 8.32 (s, 1H), 8.28-8.21 (m, 2H), 8.08-8.02 (m, 1H), 7.84 (s, 1H), 7.77-7.74 (d, 1H), 7.65-7.62 (m, 3H), 7.44-7.41 (m, 1H), 7.29-7.25 (m, 2H), 6.74-6.70 (m, 1H), 3.75 (s, 3H), 2.71 (s, 0.64H; minor isomer, CH₃), 2.33 (s, 2.36H; major isomer, CH₃).

5-(5-((1-(3-(1H-Tetrazol-5-yl)phenyl)-3-methyl-5-oxo-4,5-dihydro-1H-pyrazol-4-yl)methyl)furan-2-yl)-2-chloro-N-(3-methoxyphenyl)benzamide (NG-03-205/245)

Compound NG-03-205/245 was synthesized by an above synthetic procedure described for the preparation of compound NG-01-72 using compound NG-03-201/244 (100 mg) as a starting material. Red solid, (69 mg, 70% yield). ¹H NMR (300 MHz, DMSO): δ 10.62 (s, 1H, NH), 8.32 (s, 1H), 8.21-8.17 (m, 2H), 8.08-8.02 (s, 1H), 7.8s-7.77 (m, 2H), 7.69-7.65 (m, 3H), 7.53-7.44 (m, 1H), 7.29-7.26 (brs, 2H), 6.74-6.70 (brs, 1H), 3.75 (s, 3H), 1.98 (s, 3H).

Scheme X<sup>a</sup>. Synthesis of compound NG-04-300, NG-04-303, NG-04-304, NG-04-308, NG-04-309, NG-04-311, NG-04-312/352, NG-04-314, NG-04-322.

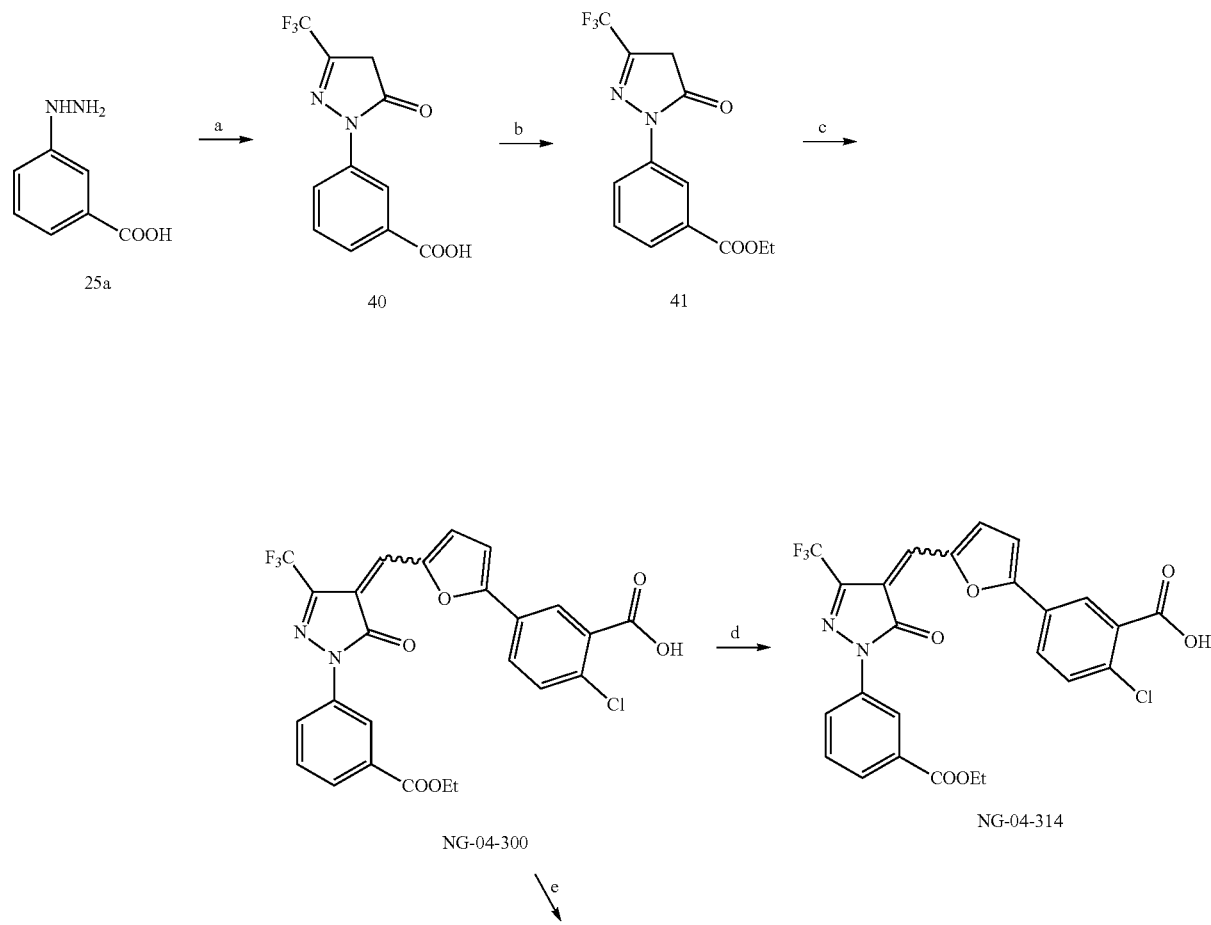

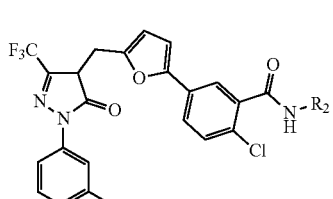
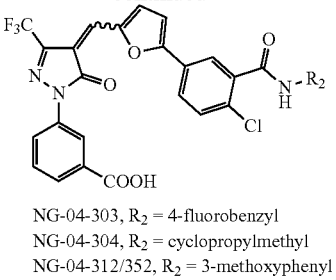
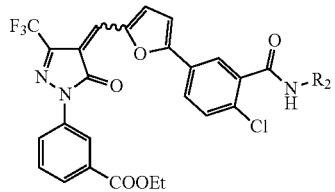

NG-04-308, R₂ = 4-fluorobenzyl
NG-04-309, R₂ = cyclopropylmethyl
NG-04-322, R₂ = 3-methoxyphenyl NG-04-303, R₂ = 4-fluorobenzyl
NG-04-304, R₂ = cyclopropylmethyl
NG-04-312/352, R₂ = 3-methoxyphenyl 42, R₂ = 4-fluorobenzyl
43, R₂ = cyclopropylmethyl
NG-04-311, R₂ = 3-methoxyphenyl

[a]Reagents and Conditions: (a) ethyl 4,4,4-trifluoroacetoacetate, AcOH, reflux for 12 h, 78%; (b) H$_2$SO$_4$, EtOH, reflux for 12 h, 81%; (c) compound 30, AcOH, reflux for 3 h, 86%; (d) LiOH, THF:EtOH:H$_2$O (4:2:1), rt for 12 h, 78%; (e) alkyl or aryl amine, EDCI, HOBt, DIPEA, DMF, rt for 18 h, 84-87%; (f) LiOH, THF:EtOH:H$_2$O (4:2:1), rt for 12 h, 64-72% (after recrystallization); (g) NaBH$_4$, MeOH, 0° C. to rt for 1.5 h, 64-69%.

Synthesis of 3-(5-Oxo-3-(Trifluoromethyl)-4,5-Dihydro-1H-Pyrazol-1-Yl)Benzoic Acid (40)

Compound 40 was synthesized by an above synthetic procedure described for the preparation of compound 26a using 3-hydrazinobenzoic acid (1 gm) and ethyl 4,4,4-trifluoroacetoacetate. Brown solid, (1.39 gm, 78% yield, require no further purification). TLC: 4% MeOH in DCM, R$_f$=0.46; visualized with UV. $^1$H NMR (300 MHz, DMSO): δ 13.03 (brs, 1H, COOH), 8.30 (s, 1H), 8.02 (d, 1H, J=8.1 Hz), 7.94 (d, 1H, J=7.89 Hz), 7.64 (t, 1H, J=7.95 and 15.87 Hz), 5.96 (s, 1H); $^{13}$C NMR (75 MHz, DMSO): δ 167.06, 154.56, 141.54, 141.05, 138.44, 132.23, 130.09, 128.15, 126.35, 122.72, 119.91, 86.27.

Synthesis of ethyl 3-(5-oxo-3-(trifluoromethyl)-4,5-dihydro-1H-pyrazol-1-yl)benzoate (41)

Compound 41 was synthesized by an above synthetic procedure described for the preparation of compound 27a using 40 (1 gm) as a starting material. Off-white solid, (893 mg, 81% yield). TLC: 50% EtOAc in hexanes, R$_f$=0.48; visualized with UV. $^1$H NMR (300 MHz, CDCl$_3$): δ 10.26 (brs, 1H), 8.49 (s, 1H), 8.03-7.99 (m, 2H), 7.55 (t, 1H, J=8.01 and 15.99 Hz), 5.87 (s, 1H), 4.53-4.45 (q, 2H, OCH$_2$), 1.47 (t, 3H, J=7.14 and 14.28 Hz, CH$_3$); $^{13}$C NMR (75 MHz, CDCl$_3$): δ 167.90, 152.81, 142.65, 142.14, 138.30, 130.37, 129.52, 128.23, 127.38, 122.76, 120.27, 86.75, 62.41, 14.29.

Synthesis of 2-chloro-5-(5-((1-(3-(ethoxycarbonyl)phenyl)-5-oxo-3-(trifluoromethyl)-1,5-dihydro-4H-pyrazol-4-ylidene)methyl)furan-2-yl)benzoic acid (NG-04-300)

Compound NG-04-300 was synthesized by an above synthetic procedure described for the preparation of compound 31a using 41 (800 mg) as a starting material. Red solid, (1.22 gm, 86% yield). TLC: 5% MeOH in DCM, R$_f$=0.48; visualized with UV. Major isomer data: $^1$H NMR (300 MHz, DMSO): δ 13.73 (brs, 1H), 8.73 (s, 1H), 8.38 (s, 1H), 8.31 (s, 1H), 8.08 (t, 2H, J=9.0 and 17.7 Hz), 7.82 (d, 1H, J=7.77 Hz), 7.74 (s, 1H), 7.69-7.57 (m, 3H), 4.36-4.29 (q, 2H, OCH$_2$), 1.33 (t, 3H, J=7.08 and 14.19 Hz, CH$_3$). $^{13}$C NMR (75 MHz, DMSO): δ 166.56, 165.58, 161.24, 160.38, 150.71, 138.10, 133.96, 132.98, 132.11, 131.73, 130.49, 130.02, 129.46, 127.88, 127.29, 126.76, 123.83, 119.75, 114.40, 114.08, 61.52, 14.60.

Synthesis of 5-(5-((1-(3-carboxyphenyl)-5-oxo-3-(trifluoromethyl)-1,5-dihydro-4H-pyrazol-4-ylidene)methyl)furan-2-yl)-2-chlorobenzoic acid (NG-04-314)

Compound NG-04-314 was synthesized by an above hydrolysis protocol described for the preparation of compound 34a using NG-04-300 (100 mg) as a starting material. Red solid, (73 mg, 78% yield). Major isomer data: $^1$H NMR (300 MHz, DMSO): δ 13.44 (brs, 1H, COOH), 8.73 (s, 1H), 8.38 (s, 1H), 8.29 (s, 1H), 8.04 (t, 2H, J=7.05 and 13.5 Hz), 7.81 (d, 1H, J=7.65 Hz), 7.72 (s, 1H), 7.66-7.53 (m, 3H); $^{13}$C NMR (75 MHz, DMSO): δ 167.18, 166.52, 161.19, 160.32, 150.69, 139.93, 139.44, 138.00, 133.98, 132.88, 132.09, 131.57, 130.38, 129.80, 127.88, 127.24, 126.93, 123.43, 122.04, 120.03, 114.42, 114.03.

Synthesis of ethyl 3-(4-((5-(4-chloro-3-((4-fluorobenzyl)carbamoyl)phenyl)furan-2-yl)methylene)-5-oxo-3-(trifluoromethyl)-4,5-dihydro-1H-pyrazol-1-yl)benzoate (42)

Compound 42 was synthesized by an above synthetic procedure described for the preparation of compound 33a using NG-04-300 (300 mg) as a starting material. Red solid, (300 mg, 84% yield). TLC: 3% MeOH in DCM, R$_f$=0.49; visualized with UV. Major isomer data: $^1$H NMR (300 MHz, DMSO): δ 9.20 (t, 1H, J=5.84 and 11.64 Hz), 8.80 (s, 1H), 8.46 (s, 1H), 8.16-8.01 (m, 3H), 7.90-7.85 (m, 2H), 7.79-7.70 (m, 2H), 7.63 (t, 1H, J=7.95 and 15.9 Hz), 7.47-7.41 (m, 2H), 7.24-7.14 (m, 2H), 4.49 (d, 2H, J=5.87 Hz, NHCH$_2$), 4.34-4.30 (q, 2H, OCH$_2$), 1.34 (t, 3H, J=7.10 and 14.16 Hz, CH$_3$).

Synthesis of ethyl 3-(4-((5-(4-chloro-3-((cyclopropylmethyl)carbamoyl)phenyl)furan-2-yl)methylene)-5-oxo-3-(trifluoromethyl)-4,5-dihydro-1H-pyrazol-1-yl)benzoate (43)

Compound 43 was synthesized by an above synthetic procedure described for the preparation of compound 33a using NG-04-300 (300 mg) as a starting material. Brown solid, (287 mg, 87% yield). TLC: 3% MeOH in DCM, R$_f$=0.46; visualized with UV. Major isomer data: $^1$H NMR (300 MHz, DMSO): δ 8.80 (s, 1H), 8.69 (t, 1H, J=4.60 and 11.06 Hz), 8.45 (s, 1H), 8.22-8.08 (m, 3H), 7.87 (s, 1H), 7.81-7.48 (m, 4H), 4.36-4.31 (q, 2H, OCH$_2$), 3.14 (t, 2H, J=6.16 and 12.24 Hz, NHCH$_2$), 1.06-1.0 (m, 1H, CH), 0.49-0.45 (m, 2H, CH$_2$), 0.28-0.24 (m, 2H, CH$_2$).

Synthesis of ethyl 3-(4-((5-(4-chloro-3-((3-methoxyphenyl)carbamoyl)phenyl)furan-2-yl)methylene)-5-oxo-3-(trifluoromethyl)-4,5-dihydro-1H-pyrazol-1-yl)benzoate (NG-04-311)

Compound NG-04-311 was synthesized by an above synthetic procedure described for the preparation of compound 33a using NG-04-300 (300 mg) as a starting material. Red solid, (308 mg, 86% yield). TLC: 3% MeOH in DCM, $R_f$=0.52; visualized with UV. Major isomer data: $^1$H NMR (300 MHz, DMSO): δ 10.53 (s, 1H, NH), 8.48 (t, 1H, J=1.83 and 3.66 Hz), 8.22 (d, 1H, J=7.14 Hz), 7.84 (d, 2H, J=7.77 Hz), 7.75 (s, 1H), 7.66-7.53 (m, 3H), 7.40 (s, 1H), 7.28-7.25 (m, 2H), 7.03 (d, 1H, J=3.33 Hz), 6.71-6.67 (m, 1H), 6.49 (d, 1H, J=6.0 Hz), 4.38-4.30 (q, 2H, OCH$_2$), 3.74 (s, 3H, OCH$_3$), 1.32 (t, 3H, J=7.11 and 14.19 Hz, CH$_3$); $^{13}$C NMR (75 MHz, DMSO): δ 165.83, 165.07, 159.97, 158.76, 157.58, 155.94, 15010, 150.02, 140.48, 139.86 137.78, 130.94, 130.06, 129.96, 129.80, 126.56, 125.51, 123.51, 121.30, 112.32, 109.83, 108.68, 105.81, 98.53, 61.46, 55.46, 14.64.

Synthesis of 3-(4-((5-(4-chloro-3-((4-fluorobenzyl)carbamoyl)phenyl)furan-2-yl)methylene)-5-oxo-3-(trifluoromethyl)-4,5-dihydro-1H-pyrazol-1-yl)benzoic acid (NG-04-303)

Compound NG-04-303 was synthesized by an above hydrolysis protocol described for the preparation of compound 34a using compound 42 (200 mg) as a starting material. Red solid, (137 mg, 72% yield). Major isomer data: $^1$H NMR (300 MHz, DMSO): δ 13.23 (brs, 1H, COOH), 9.18 (t, 1H, J=5.85 and 11.64 Hz), 8.82 (s, 1H), 8.48 (s, 1H), 8.16-8.03 (m, 3H), 7.88-7.84 (m, 2H), 7.79-7.70 (m, 2H), 7.65 (t, 1H, J=7.95 and 15.9 Hz), 7.45-7.40 (m, 2H), 7.21-7.13 (m, 2H), 4.49 (d, 2H, J=5.91 Hz, NHCH$_2$); $^{13}$C NMR (75 MHz, DMSO): δ 167.22, 166.14, 163.31, 161.38, 160.72, 160.10, 150.75, 138.30, 138.08, 135.48, 132.52, 132.11, 130.51, 129.97, 129.85, 129.62, 128.66, 127.99, 127.10, 123.84, 120.37, 115.66, 115.38, 114.47, 114.05, 42.36.

Synthesis of 3-(4-((5-(4-chloro-3-((cyclopropylmethyl)carbamoyl)phenyl)furan-2-yl)methylene)-5-oxo-3-(trifluoromethyl)-4,5-dihydro-1H-pyrazol-1-yl)benzoic acid (NG-04-304)

Compound NG-04-304 was synthesized by an above hydrolysis protocol described for the preparation of compound 34a using compound 43 (200 mg) as a starting material. Brown solid, (127 mg, 67% yield). Major isomer data: $^1$H NMR (300 MHz, DMSO): δ 13.21 (brs, 1H, COOH), 8.80 (s, 1H), 8.71 (t, 1H, J=5.55 and 11.10 Hz), 8.46 (s, 1H), 8.26-8.06 (m, 3H), 7.87 (s, 1H), 7.80-7.50 (m, 4H), 3.16 (t, 2H, J=6.12 and 12.24 Hz, NHCH$_2$), 1.05-0.99 (m, 1H, CH), 0.48-0.43 (m, 2H, CH$_2$), 0.26-0.21 (m, 2H, CH$_2$); $^{13}$C NMR (75 MHz, DMSO): δ 167.39, 165.90, 161.42, 160.82, 150.76, 140.11, 138.75, 138.10, 132.52, 132.12, 131.12, 130.55, 129.99, 127.81, 127.27, 126.15, 123.92, 120.44, 114.43, 113.99, 43.72, 11.14, 3.74.

Synthesis of 3-(4-((5-(4-chloro-3-((3-methoxyphenyl)carbamoyl)phenyl)furan-2-yl)methylene)-5-oxo-3-(trifluoromethyl)-4,5-dihydro-1H-pyrazol-1-yl)benzoic acid (NG-04-312/352)

Compound NG-04-312/352 was synthesized by an above hydrolysis protocol described for the preparation of compound 34a using compound NG-04-311 (200 mg) as a starting material. Red solid, (122 mg, 64% yield). Major isomer data: $^1$H NMR (300 MHz, DMSO): δ 13.23 (brs, 1H, COOH), 10.55 (s, 1H, NH), 8.49 (s, 1H), 8.20 (d, 1H, J=7.5 Hz), 7.84-7.73 (m, 3H), 7.64-7.51 (m, 3H), 7.41 (s, 1H), 7.28-7.23 (m, 2H), 7.03 (d, 1H, J=3.33 Hz), 6.71-6.68 (m, 1H), 6.33 (d, 1H, J=3.06 Hz), 3.74 (s, 3H, OCH$_3$); $^{13}$C NMR (75 MHz, DMSO): 175.00, 171.76, 167.39, 165.08, 159.97, 158.74, 156.00, 149.48, 140.49, 139.80, 137.78, 131.82, 130.06, 129.97, 129.62, 127.99, 126.69, 125.26, 123.51, 121.57, 112.32, 109.84, 108.78, 105.75, 98.53, 55.46.

Synthesis of 3-(4-((5-(4-chloro-3-((4-fluorobenzyl)carbamoyl)phenyl)furan-2-yl)methylene)-5-oxo-3-(trifluoromethyl)-4,5-dihydro-1H-pyrazol-1-yl)benzoic acid (NG-04-308)

Compound NG-04-308 was synthesized by an above synthetic procedure described for the preparation of compound NG-01-72 using compound NG-04-303 (80 mg) as a starting material. Red solid, (55 mg, 69% yield). $^1$H NMR (300 MHz, DMSO): δ 12.77 (brs, 1H, COOH), 9.18 (t, 1H, J=5.64 and 11.76 Hz), 8.49 (s, 1H), 8.19-8.03 (m, 2H), 7.95-7.86 (m, 2H), 7.80-7.51 (m, 4H), 7.45-7.37 (m, 2H), 7.20-7.14 (m, 2H), 4.49 (d, 2H, J=6.09 Hz, NHCH$_2$), 2-78-2.62 (q, 2H); $^{13}$C NMR (75 MHz, DMSO): δ 174.99, 171.76, 167.23, 166.14, 163.35, 161.43, 160.73, 160.10, 150.78, 138.34, 138.10, 135.48, 132.52, 132.13, 131.21, 130.02, 129.86, 129.61, 128.00, 127.36, 127.16, 123.98, 120.47, 115.66, 115.38, 114.52, 114.06, 72.89, 43.13, 42.35.

Synthesis of 3-(4-((5-(4-chloro-3-((cyclopropylmethyl)carbamoyl)phenyl)furan-2-yl)methyl)-5-oxo-3-(trifluoromethyl)-4,5-dihydro-1H-pyrazol-1-yl)benzoic acid (NG-04-309)

Compound NG-04-309 was synthesized by an above synthetic procedure described for the preparation of compound NG-01-72 using compound NG-04-304 (80 mg) as a starting material. Dark brown solid, (52 mg, 65% yield). $^1$H NMR (300 MHz, DMSO): δ 12.78 (brs, 1H, COOH), 8.71 (t, 1H, J=5.61 and 11.19 Hz), 8.47 (s, 1H), 8.20-8.09 (m, 2H), 8.02-7.86 (m, 2H), 7.80-7.49 (m, 4H), 3.19 (t, 2H, J=6.12 and 12.45 Hz, NHCH$_2$), 2-78-2.62 (q, 2H), 1.03-0.98 (m, 1H, CH), 0.48-0.42 (m, 2H, CH$_2$), 0.27-0.22 (m, 2H, CH$_2$); $^{13}$C NMR (75 MHz, DMSO): δ 175.00, 171.76, 167.39, 167.23, 165.91, 161.46, 160.83, 150.77, 138.77, 138.11, 132.52, 132.13, 131.13, 130.01, 129.99, 127.82, 127.28, 126.17, 123.97, 120.47, 114.45, 114.00, 72.89, 43.72, 43.13, 11.14, 3.74.

Synthesis of 3-(4-((5-(4-chloro-3-((3-methoxyphenyl)carbamoyl)phenyl)furan-2-yl)methyl)-5-oxo-3-(trifluoromethyl)-4,5-dihydro-1H-pyrazol-1-yl)benzoic acid (NG-04-322)

Compound NG-04-322 was synthesized by an above synthetic procedure described for the preparation of compound NG-01-72 using compound NG-04-312 (80 mg) as a starting material. Brown solid, (51 mg, 64% yield). $^1$H NMR (300 MHz, DMSO): δ 12.82 (brs, 1H, COOH), 10.54 (s, 1H, NH), 8.49 (s, 1H), 8.20 (d, 1H, J=8.34 Hz), 7.88-7.75 (m, 3H), 7.64-7.51 (m, 3H), 7.41 (s, 1H), 7.26-7.22 (m, 2H), 6.70-6.67 (m, 1H), 6.32 (s, 1H), 3.74 (s, 3H, OCH$_3$), 2-79-2.62 (q, 2H); $^{13}$C NMR (75 MHz, DMSO): δ 175.00, 171.76, 167.39, 165.08, 159.96, 158.74, 156.00, 149.48, 140.49, 139.79, 137.78, 131.82, 130.05, 129.97, 129.62, 128.36, 126.68, 125.09, 123.51, 121.57, 112.32, 109.83, 108.78, 105.75, 98.53, 72.90, 55.46, 43.13, 31.16.

Example 2

Overexpression and Purification of Full Length Human XPA

Sf9 cells were infected with XPA virus, and the cellular pellet was lysed by dounce homogenization in buffer A containing 50 mM Tris, 100 mM NaCl, 0.1% (v/v) Triton X-100, 10% (v/v) glycerol, and 10 mM BME, along with a protease inhibitor cocktail. Following sonication, imidazole was added to 1 mM to the cellular extract, which was then loaded onto a 2 mL nickel-NTA agarose column Bound protein was eluted in buffer A with 80 mM imidazole and protein containing fractions identified using Bradford analysis. Protein containing fractions were then pooled and loaded directly onto a 2 mL heparin-Sepharose column Protein was eluted using a gradient from 100 mM to 1 M NaCl in heparin buffer (50 mM Tris, pH 7.5, 1 mM EDTA, 10% (v/v) glycerol, and 1 mM DTT with protease inhibitor mix). Fractions containing XPA were identified using Bradford and SDS-PAGE analysis, pooled and dialyzed overnight in heparin buffer and stored at −80° C.

Example 3

Overexpression and Purification of $XPA_{98-239}$ MBD (DBD)

The XPA minimal binding domain was expressed in *E. coli.* B1-21(DE3) from a plasmid driving expression of an N-terminal 6-histidine tagged fragment corresponding to amino acids 98-239. The recombinant protein was purified by a two-step column chromatography procedure similar to the methodology used for full length XPA.

Example 4

Electrophoretic Mobility Shift Assay (EMSA)

Figure 3:
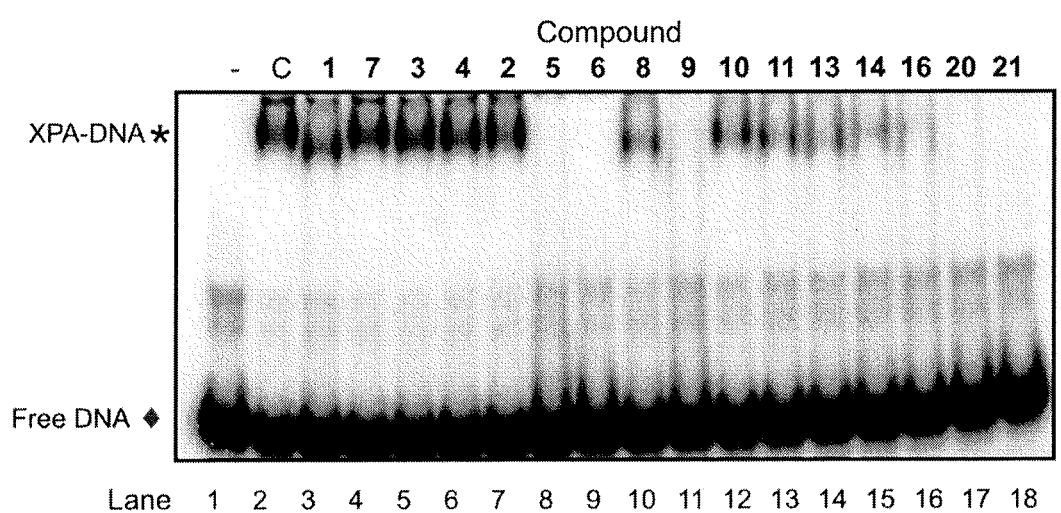
FIG. 3 shows EMSA analysis of XPA-DNA binding. Purified XPA (lanes 2-18) was mixed with DMSO (Lane 2, C) control or the indicated compound at a concentration of 50 µM (Lanes 3-18). $^{32}$P labeled ds-platinum damaged DNA was added and incubation continued for 30 minutes on ice. The products were separated on a 6% native gel by electrophoresis at 4° C. Products were detected and quantified by PhosphorImager analysis. The free DNA is indicated by the diamond and the XPA-DNA complex by the asterisk.
Figure 4A:
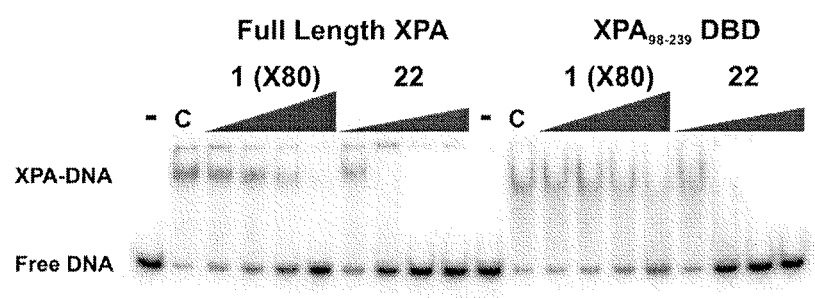
FIGS. 4A-B show the effects of increasing concentrations of compounds 1 (X80) and 22.
Figure 4B:
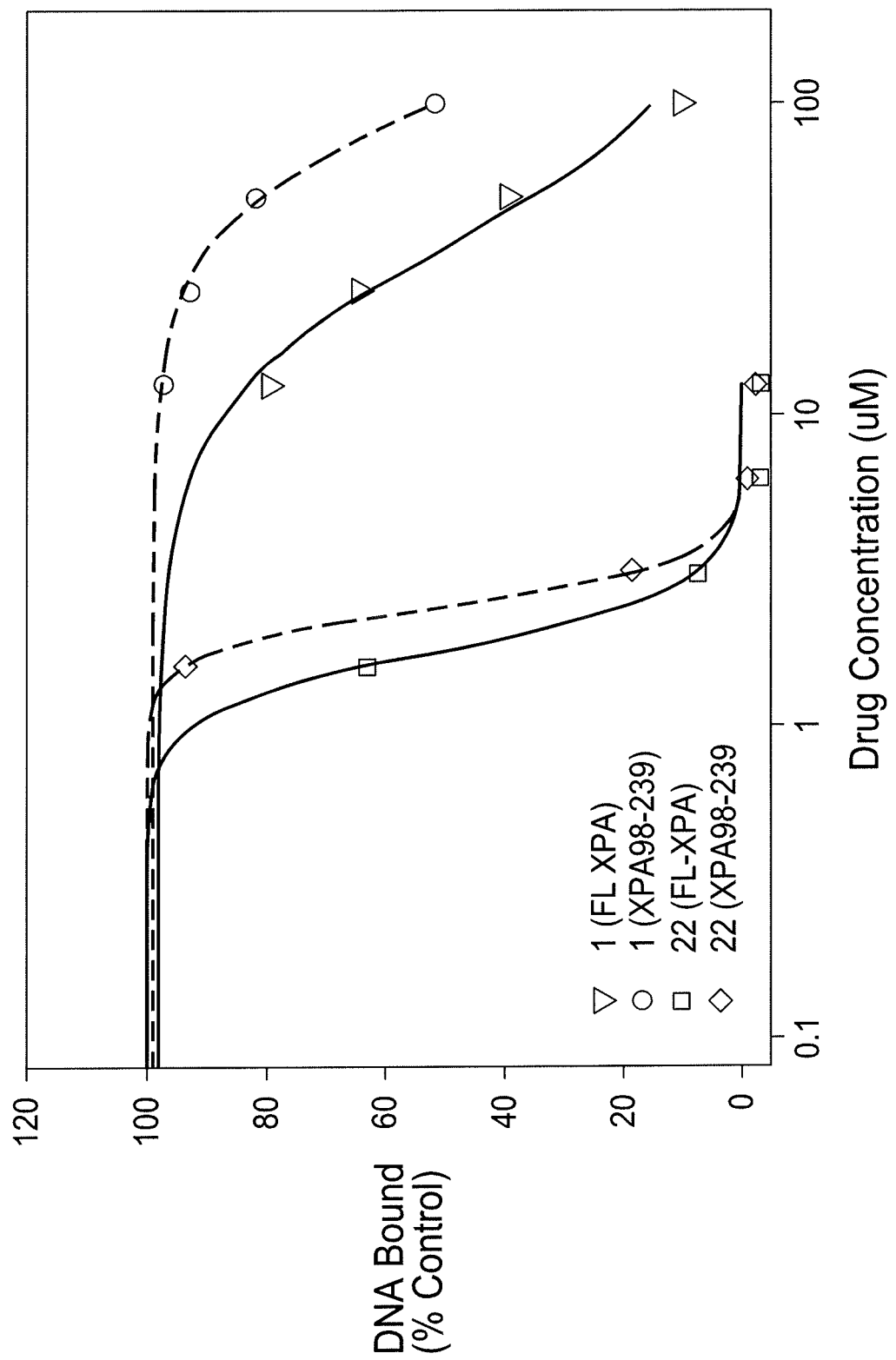

EMSA was carried out using previously described procedure with the following modification. Reactions were performed in volume of 20 µL, containing a $^{32}P$ labeled 30 bp duplex DNA containing a single 1,2 dGpG cisplatin adduct. Compounds were pre-incubated on ice with the indicated amount of XPA and products separated by electrophoresis on a non-denaturing 6% polyacrylamide gel. Gels were cooled, loaded and electrophoresis performed at 4° C. Gels were used to expose a PhosphorImager screen and band intensity determined and % binding and inhibition calculated as we have previously described. The results of these assays using full length XPA protein can be seen in FIG. 3 and Table 1. The results of the assays using compounds 1 and 22 with the minimal DNA-binding domain (DBD) consisting of amino acids 98-239 ($XPA_{98-239}$) are shown in FIGS. 4A and 4B.

Example 5

DNA Intercalation Fluorescence Displacement Assay

Figure 6:
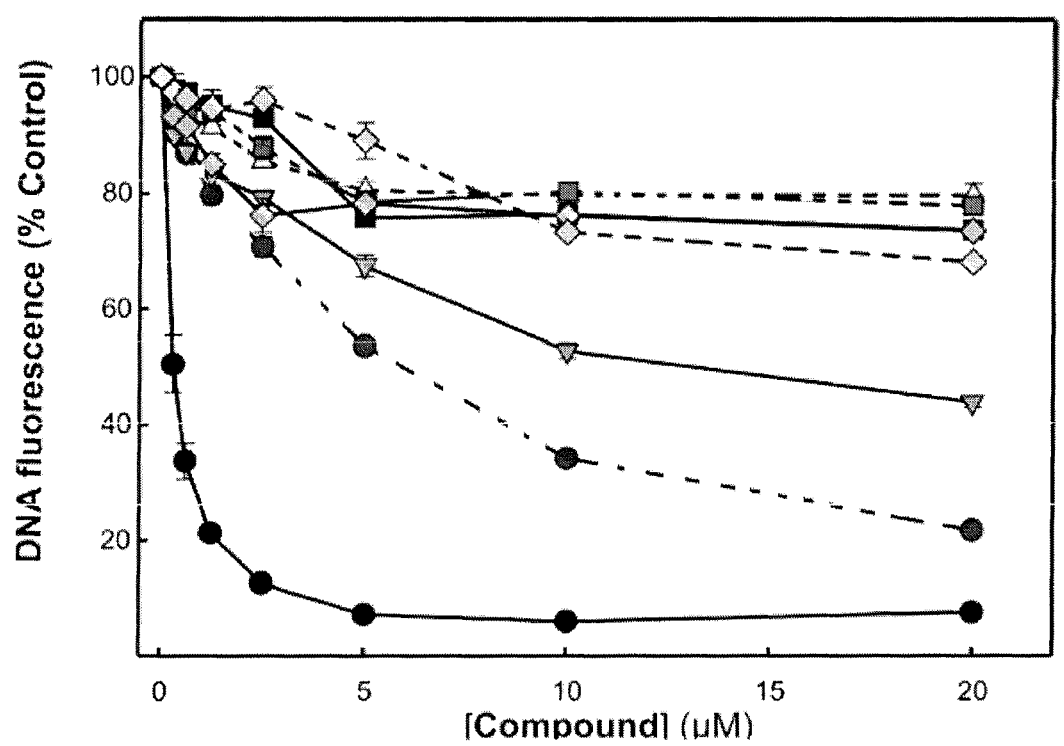
FIG. 6 shows the analysis of compound interactions with DNA. The indicated concentrations of doxorubicin (●, solid line), compound 22 (●, broken line), 24 (▼, solid line), 34a (♦, broken line), 34d (■, solid line), 34i (♦, solid line), 34k (■, broken line), and 39c (♦, broken line), were analyzed for the ability to displace a fluorescent Sybr-green DNA intercalator as a measure of compound DNA interactions. The assay was performed and fluorescence measured as described herein. The data represent the average and SD of three independent experimental determinations performed in duplicates.

A competitive DNA intercalation assay was performed using SYBR-Green (Sigma) and salmon sperm DNA (Fisher). Reactions were carried out in 25 mM MOPS (pH 6.5) containing sonicated salmon sperm DNA (8.29 ng/µL), SYBR-Green and varying concentrations of XPA inhibitors. Reactions were performed in a black 96-well plate in a final volume of 110 mL. Doxorubicin, a known non-covalent DNA binding chemotherapeutic, was used as a positive control. Fluorescence was measured using a BioTek® Synergy™ H1 hybrid multi-mode microplate reader with an excitation wavelength of 485 nm, emission wavelength of 528 nm and a read height of 7 mm Data were collected using BioTek® Gen5™ reader software. Reactions were incubated a maximum of 5 min before measurements were collected. The results of this assay with doxorubicin and compounds 22, 24, 34a, 34d, 34i, 34k and 39c are shown in FIG. 6. These results are consistent with our XPA compounds that specifically inhibit protein-DNA interaction by binding to the XPA protein and not via binding to the DNA.

Example 6

Molecular Docking

Docking studies were performed using a solution NMR structure, PDB: 1XPA obtained from the Protein Data Bank (PDB) and prepared using the Protein Preparation Wizard. In this step, force field atom types and bond orders are assigned, missing atoms are added, tautomer/ionization states are assigned, water orientations are sampled, Asn, Gln, and His residues are flipped to optimize the hydrogen bond network, and a constrained energy minimization is performed. XPA inhibitors were drawn in ChemDraw as MDL molfiles and prepared for docking using LigPrep including a minimization with the OPLS3 force field. All chiral centers were retained as specified in the literature. One low energy ring conformation per compound was generated. Ionization states and tautomer forms were enumerated at pH 7.0±2.0 with Epik.

XPA inhibitors were flexibly docked into the cleft defined by residues 138-142, 165-171, 174, and 177-181 using the Glide SP protocol with default settings. Docking poses were evaluated based on visual interrogation and calculated docking score. Potential amino acid interactions were determined based on proximity to each compound as revealed by docking analysis. XPA interactions with small molecules were viewed using Pymol using cartoon, surface and compounds interaction views. All the molecular modeling within this study was performed using Maestro software v11 (Schrödinger) operating in a Linux environment.

Figure 2B:
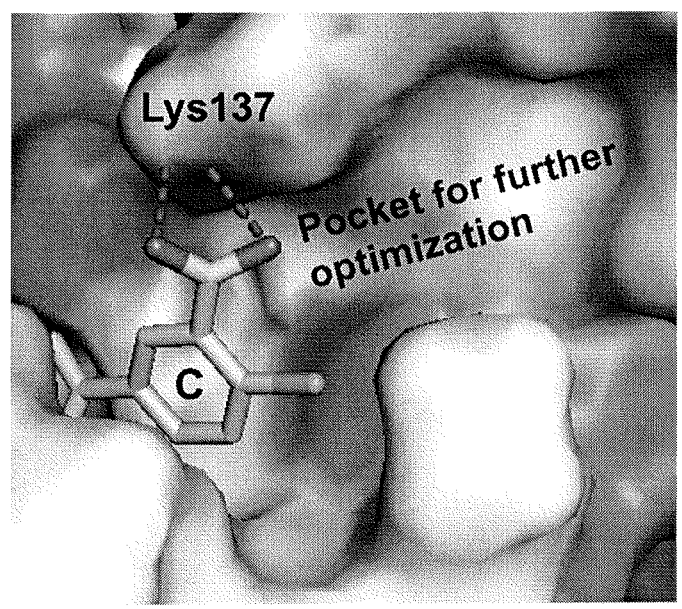
FIG. 2B shows a schematic representation of SAR exploration rationale: A pocket surrounding Ring C of compound 1 (X80) for further structural optimization. Potential hydrogen bond contacts shown in dashed lines.

Using the 3D structure of XPA determined by solution NMR (PDB: 1XPA), the coordinates of the C-terminal subdomain (residues 131-210) were found to have direct contact with a DNA ligand. Therefore, during our previous studies and also in these studies, we have targeted the cleft consisting of amino acid residues 138-142, 165-171, 174, and 177-181 for small molecule docking. Initial molecular docking studies with the compound 1 (X80) revealed that the interaction of compound 1 carboxylic acid (Ring C) with the cleft contacting Lys137 is critical for inhibitory activity, and there is a large space-filling pocket around aromatic Ring C that can be exploited for further structural optimization (FIG. 2B). To further investigate the feasibility of targeting drug-like binding pockets and identify inhibitors with improved potency, we first searched the virtual Chemdiv (San Diego, USA) and AKos GmbH (Steinen, Germany) library for X80 analogs with a criterion of 85-95% structural similarity. Approximately 30 commercially available analogs (Table 1) were acquired and tested for their activity in inhibiting the XPA-DNA interaction.

Figure 5A:
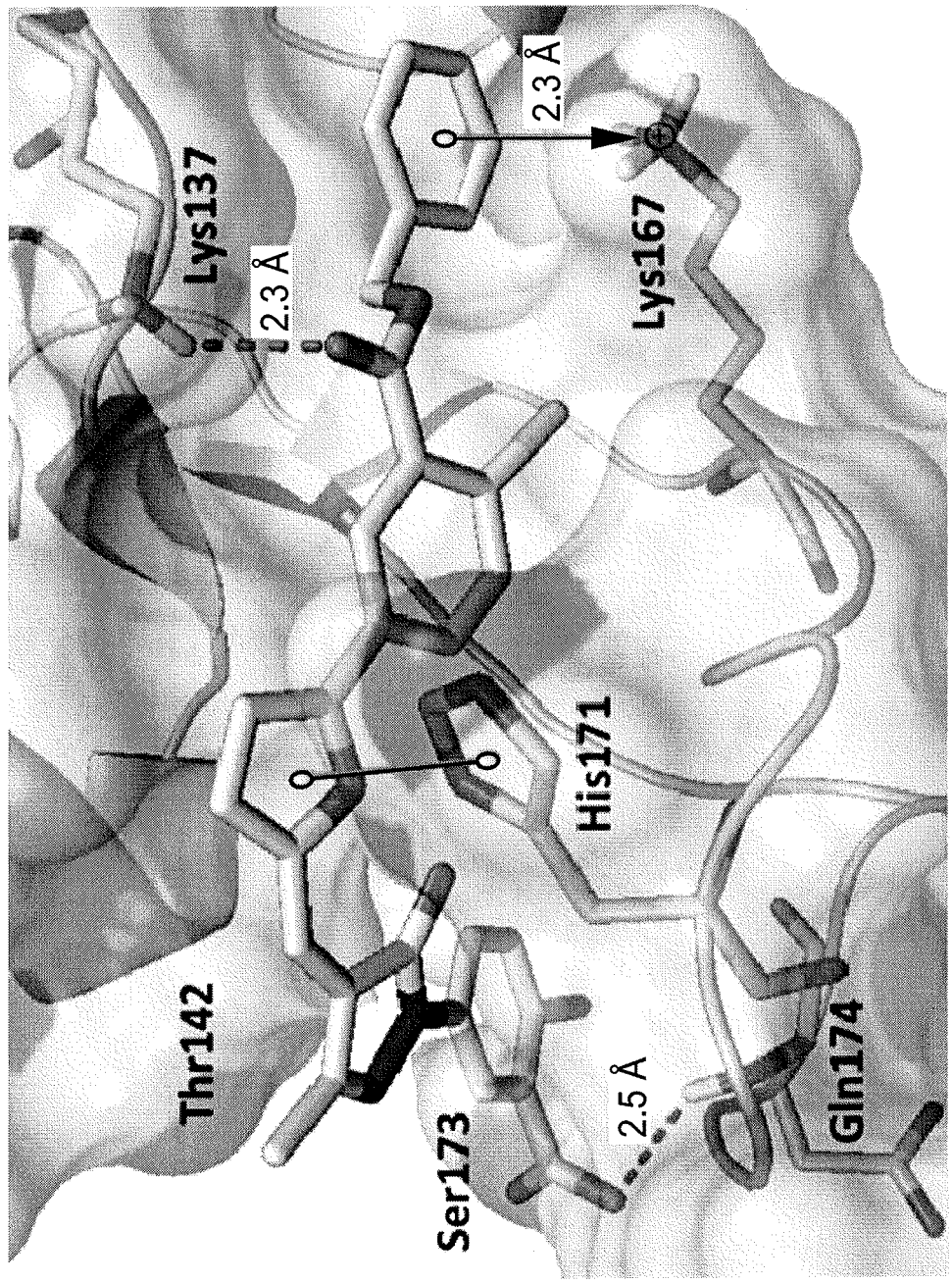
FIGS. 5A-B show molecular docking studies (PDB code: 1XPA).
Figure 5B:
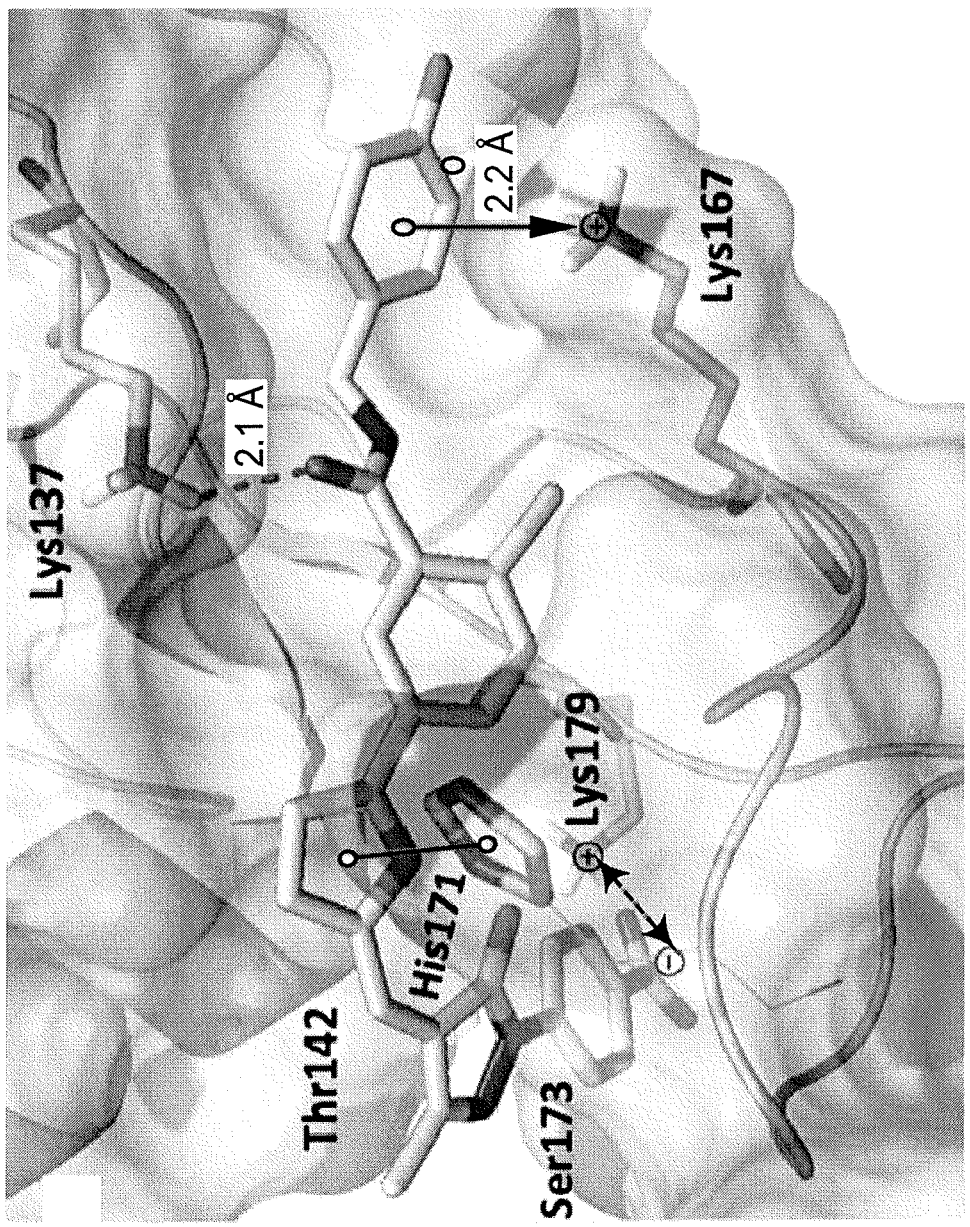

FIGS. 5A and 5B show the binding and molecular interactions of compound 22 and 34i Z-isomers within XPA MBD. The molecular interaction of 22 (FIG. 5A) and 34i (FIG. 5B). Z-isomer is largely ascribed to various electrostatic interactions, including, i) compound 22 ester carbonyl and compound 34i amide carbonyl make hydrogen bond contacts with the amine of Lys137; ii) 3'-COOH (Ring A) of compound 22 shows hydrogen bond contacts with the backbone amine of Gln174, 4'-COOH of compound 34i does not interact with Gln174 but makes salt-bridge interactions with cleft amino acid, Lys179; and iii) the π-π stacking interactions between the furan moiety and the aromatic ring of His171 in both compounds.

TABLE 1

| Example | Compound Name | Structure | IC$_{50}$ (μM) |
|---------|---------------|-----------|----------------|
| | X80 | | >50 |
| | 0277 | | 18 |
| | 2138 | | 12 |
| | 0530 | | 10 |

TABLE 1-continued

| Example | Compound Name | Structure | IC$_{50}$ (μM) |
|---|---|---|---|
| | 2727 | | 8, 14 |
| | 0529 | | 8.5 |
| | 2249 | | 2.5 |
| | 2922 | | 3 |
| | 5135 | | 1.5 |

TABLE 1-continued

| Example | Compound Name | Structure | $IC_{50}$ (µM) |
|---|---|---|---|
| | 7997 | | 25 |
| | 2849 | | 9 |
| | 2777 | | 15 |
| | 3125 | | 3 |
| | 3315 | | 8 |

TABLE 1-continued

| Example | Compound Name | Structure | IC$_{50}$ (µM) |
|---|---|---|---|
| | 3278 | | 7 |
| | 5102 | | 0.6 |
| | 2733 | | 5 |
| 31a | NG-01-43 | 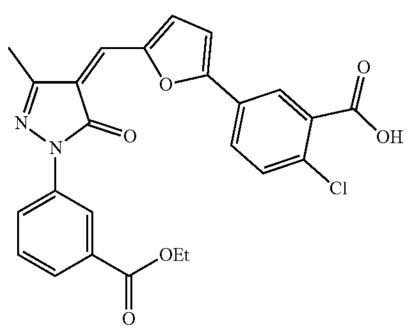 [SMILES: CCOC(=O)c1cccc(N2N=C(C)/C(=C/c3ccc(-c4ccc(Cl)c(C(=O)O)c4)o3)C2=O)c1] | >25 |
| 33a | NG-01-44 | 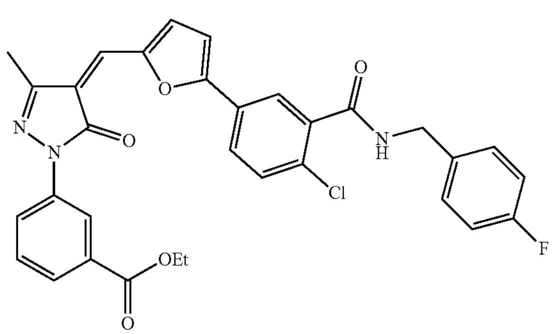 [SMILES: CCOC(=O)c1cccc(N2N=C(C)/C(=C/c3ccc(-c4ccc(Cl)c(C(=O)NCc5ccc(F)cc5)c4)o3)C2=O)c1] | >25 |

TABLE 1-continued

| Example | Compound Name | Structure | IC$_{50}$ (µM) |
|---|---|---|---|
| 34a | NG-01-54/01-64 | 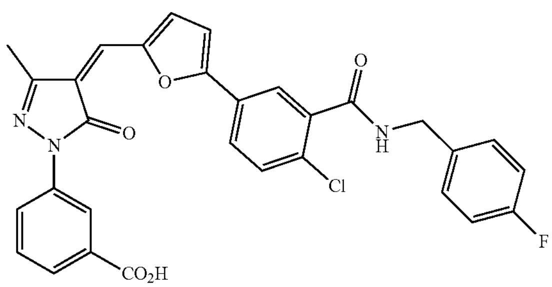 [SMILES: CC1=NN(c2cccc(C(=O)O)c2)C(=O)/C1=C\c1ccc(-c2ccc(Cl)c(C(=O)NCc3ccc(F)cc3)c2)o1] | 12,15,13, 15,20,17, 23,19 |
| | NG-01-65 | | >25 |
| 34b | NG-01-68/2-140/3-180 | 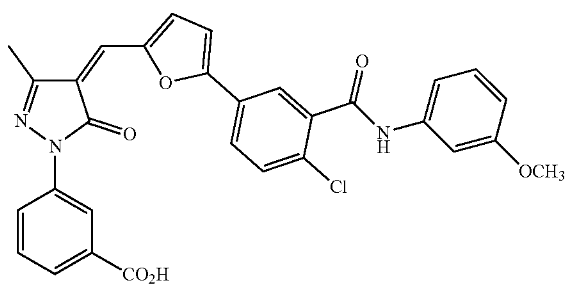 | 18,20,20 |
| 34d | NG-01-70 | 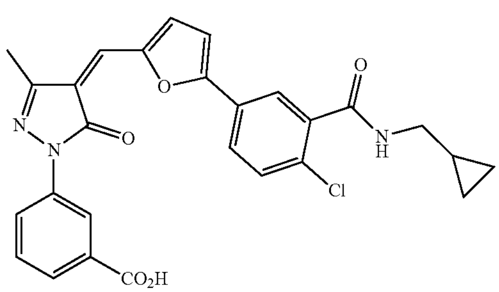 [SMILES: CC1=NN(c2cccc(C(=O)O)c2)C(=O)/C1=C\c1ccc(-c2ccc(Cl)c(C(=O)NCC3CC3)c2)o1] | 10,15, 16,16 |
| | NG-01-72R | | 42 |

TABLE 1-continued

| Example | Compound Name | Structure | IC$_{50}$ (μM) |
|---|---|---|---|
| 34f | NG-01-78 | 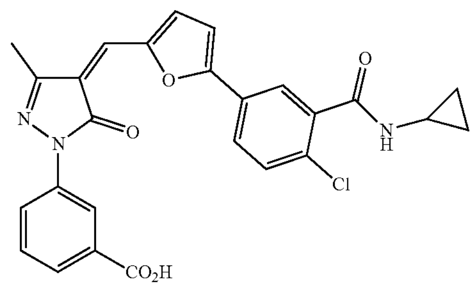 [SMILES: CC1=NN(c2cccc(C(=O)O)c2)C(=O)/C1=C\c1ccc(-c2ccc(Cl)c(C(=O)NC3CC3)c2)o1] | 32 |
| 34k | NG-01-91 | 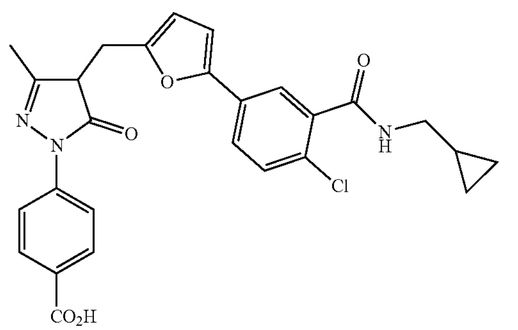 [SMILES: CC1=NN(c2ccc(C(=O)O)cc2)C(=O)C1Cc1ccc(-c2ccc(Cl)c(C(=O)NCC3CC3)c2)o1] | 7,9, 10,25 |
| 34i | NG-01-92 | 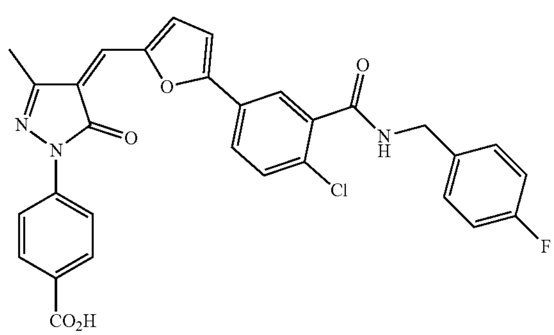 [SMILES: CC1=NN(c2ccc(C(=O)O)cc2)C(=O)/C1=C\c1ccc(-c2ccc(Cl)c(C(=O)NCc3ccc(F)cc3)c2)o1] | 12,14,9,7, 12,15 |
| 34g | NG-02-99 | 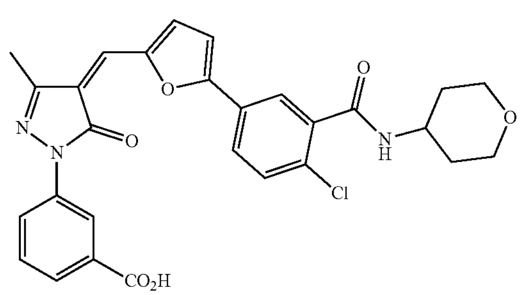 [SMILES: CC1=NN(c2cccc(C(=O)O)c2)C(=O)/C1=C\c1ccc(-c2ccc(Cl)c(C(=O)NC3CCOCC3)c2)o1] | 40 |
| 34h | NG-02-100 | 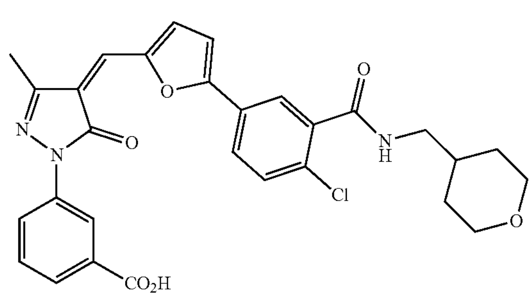 [SMILES: CC1=NN(c2cccc(C(=O)O)c2)C(=O)/C1=C\c1ccc(-c2ccc(Cl)c(C(=O)NCC3CCOCC3)c2)o1] | 15 |

TABLE 1-continued

| Example | Compound Name | Structure | IC$_{50}$ (μM) |
|---|---|---|---|
| 39d | NG-02-112 | 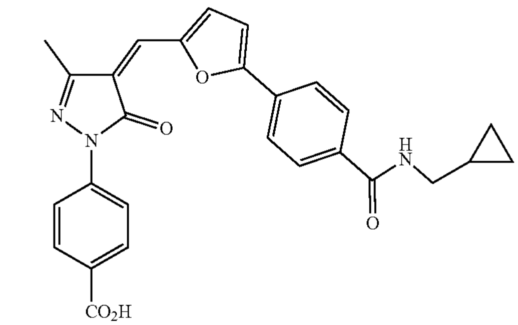 [SMILES: CC1=NN(c2ccc(C(=O)O)cc2)C(=O)/C1=C\c1ccc(-c2ccc(C(=O)NCC3CC3)cc2)o1] | 12,35,30 |
| 39c | NG-02-113 | 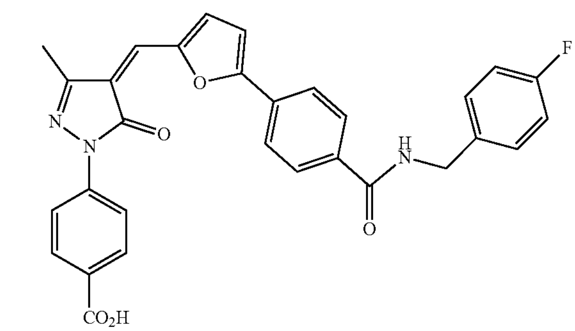 [SMILES: CC1=NN(c2ccc(C(=O)O)cc2)C(=O)/C1=C\c1ccc(-c2ccc(C(=O)NCc3ccc(F)cc3)cc2)o1] | 8,10,19 |
| | NG-02-132/ NG-02-149 | | 9,5 |
| | NG-02-150 | | 40 |

TABLE 1-continued

| Example | Compound Name | Structure | IC$_{50}$ (μM) |
|---|---|---|---|
| | NG-02-151 | | 15, 35 |
| | NG-02-154 | | 45 |
| | NG-02-162/ NG-02-162C | | 35, 35 |
| | NG-03-185 | | 2, 20, 22 |
| | NG-03-188 | | 2, 30, 15 |

TABLE 1-continued

| Example | Compound Name | Structure | IC$_{50}$ (μM) |
|---|---|---|---|
| | NG-03-189 | | 12 |
| | NG-03-193 | | >25 |
| | NG-03-201/244 | | 50 |
| | NG-03-203 | | 3, 7.5, 11 |
| | NG-03-205 | | |

TABLE 1-continued

| Example | Compound Name | Structure | IC$_{50}$ (μM) |
|---|---|---|---|
| | NG-03-206 | | 11 |
| | NG-03-207 | | 12.5 |
| | NG-03-224 | | 30 |
| | NG-03-226 | | 20, 15 |
| | NG-03-227 | | 7 |

TABLE 1-continued

| Example | Compound Name | Structure | IC$_{50}$ (µM) |
|---|---|---|---|
| | NG-03-231 | | 40 |
| | NG-03-232 | | 20 |
| | NG-03-234 | | 12 |
| | NG-03-236 | | 12 |
| | NG-03-238 | | 45 |

TABLE 1-continued
| Example | Compound Name | Structure | IC$_{50}$ (μM) |
|---|---|---|---|
| | NG-03-270 | 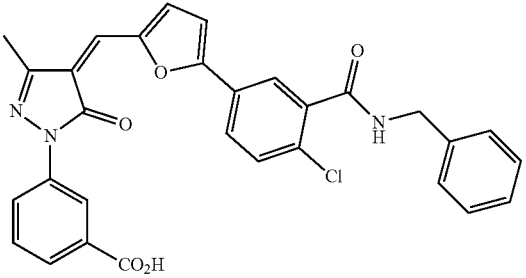 [SMILES: CC1=NN(c2cccc(C(=O)O)c2)C(=O)/C1=C\c1ccc(-c2ccc(Cl)c(C(=O)NCc3ccccc3)c2)o1] | 36 |
| | NG-03-271 | 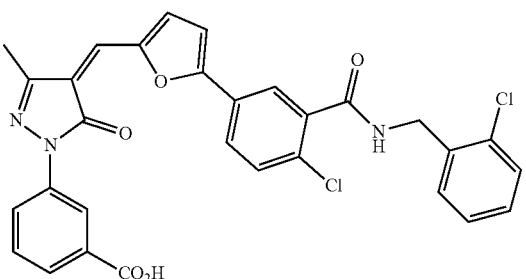 | 40 |
| | NG-04-274 | 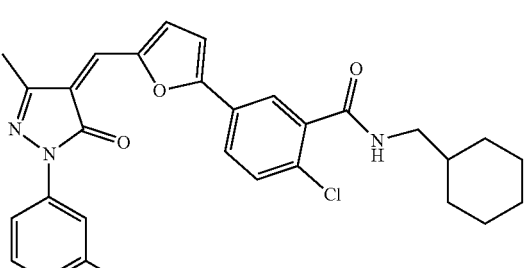 | 35 |
| | NG-03-286 | 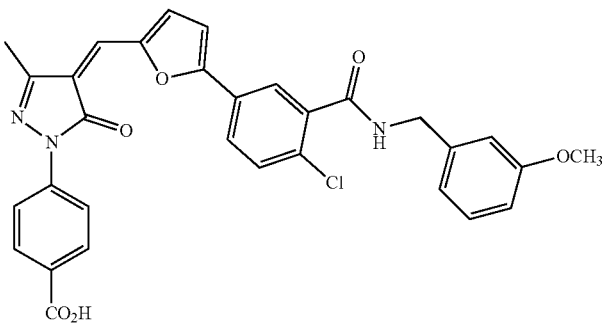 [SMILES: COc1cccc(CNC(=O)c2cc(-c3ccc(/C=C4\C(=O)N(c5ccc(C(=O)O)cc5)N=C4C)o3)ccc2Cl)c1] | 38 |
| | NG-04-294 | 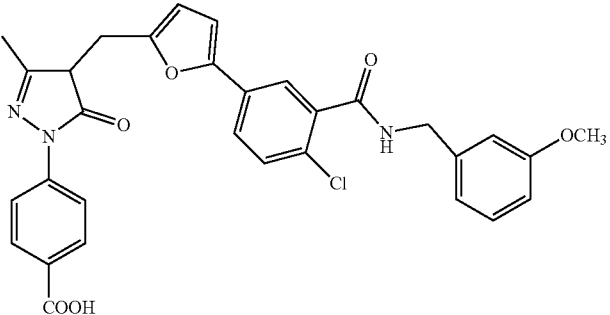 [SMILES: COc1cccc(CNC(=O)c2cc(-c3ccc(CC4C(=O)N(c5ccc(C(=O)O)cc5)N=C4C)o3)ccc2Cl)c1] | 40 |

TABLE 1-continued

| Example | Compound Name | Structure | IC$_{50}$ (μM) |
|---|---|---|---|
| | NG-04-300 | | 40 |
| | NG-04-303 | | 25 |
| | NG-04-304 | | >50 |
| | NG-04-308 | | 22 |
| | NG-04-309 | | 40 |

TABLE 1-continued

| Example | Compound Name | Structure | IC$_{50}$ (μM) |
|---|---|---|---|
| | NG-04-311 | | >50 |
| | NG-04-312 | | >50 |
| | NG-04-314 | | 15 |
| | NG-04-322 | | 30 |

We claim:
1. A method of treating cancer in a patient comprising
a. administering a therapeutically effective amount of a compound of the formula II, or a pharmaceutically acceptable salt thereof,

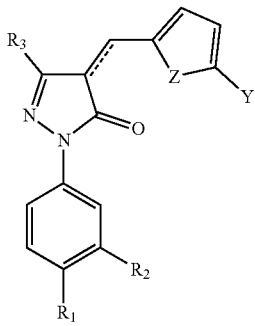

wherein
Z is O or S;
$R^1$ is H and $R^2$ is —$CO_2R^6$ or $R^1$ is —$CO_2R^6$ and $R^2$ is H;
$R^3$ is H, halogen, or $C_1$-$C_6$ alkyl, wherein each hydrogen atom in $C_1$-$C_6$ alkyl, $C_2$-$C_6$ alkenyl, $C_2$-$C_6$ alkynyl or $C_3$-$C_6$ cycloalkyl is independently optionally substituted with halogen;
Y is —$C(O)NR^4R^5$ or phenyl, wherein each hydrogen atom in phenyl is optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^4$, —CN, —$NO_2$, —$C(O)R^4$, —$CO_2R^4$, —$C(O)NR^4R^5$, —$OS(O)R^4$, —$OS(O)_2R^4$, —$SR^4$, —$S(O)R^4$, —$S(O)_2R^4$, —$S(O)NR^4R^5$, —$S(O)_2NR^4R^5$, —$OS(O)NR^4R^5$, —$OS(O)_2NR^4R^5$, and —$NR^4R^5$, or two adjacent hydrogen atoms on phenyl are optionally substituted with a group that combines with the carbon atoms to which they are attached to form a 5- to 7-membered heterocycloalkyl ring;
$R^4$ and $R^5$ are each independently selected from the group consisting of H, $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl), —$C_1$-$C_6$ alkyl-($C_6$—$C_{10}$ aryl), 3- to 7-membered heterocycloalkyl, $C_6$-$C_{10}$ aryl and 5- to 7-membered heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl) or —$C_1$-$C_6$ alkyl-($C_6$-$C_{10}$ aryl) is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —$C(O)R^8$, —$CO_2R^8$, —$C(O)NR^8R^9$, —$OS(O)R^8$, —$OS(O)_2R^8$, —$SR^8$, —$S(O)R^8$, —$S(O)_2R^8$, —$S(O)NR^8R^9$, —$S(O)_2NR^8R^9$, —$OS(O)NR^8R^9$, —$OS(O)_2NR^8R^9$, and —$NR^8R^9$;
$R^6$ is H;
each $R^8$ and $R^9$ is independently selected from the group consisting of H, $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl), —$C_1$-$C_6$ alkyl-($C_6$-$C_{10}$ aryl), 3- to 7-membered heterocycloalkyl and $C_6$-$C_{10}$ aryl; $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl) or —$C_1$-$C_6$ alkyl-($C_6$-$C_{10}$ aryl) is independently optionally substituted with halogen, and ===== is either a single bond or a pi-bond; and the compound is not of the formula

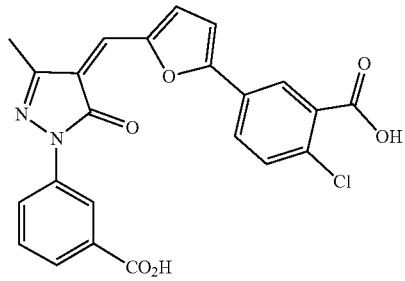 [SMILES: CC1=NN(c2cccc(C(=O)O)c2)C(=O)/C1=C\c1ccc(-c2ccc(Cl)c(C(=O)O)c2)o1]

b. administering a therapeutically effective amount of an additional cancer therapy, wherein the cancer is esophageal cancer, colon cancer, bladder cancer, ovarian cancer, testicular cancer, head & neck cancer, or lung cancer.

2. The method of claim 1, wherein the compound is of the formula I, or a pharmaceutically acceptable salt thereof,

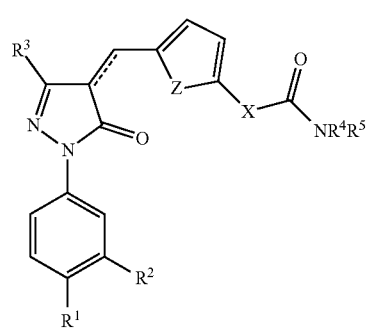

wherein
X is absent or $C_6$-$C_{10}$ aryl, wherein each hydrogen in $C_6$-$C_{10}$ aryl is optionally substituted with an $R^{10}$;
Z is O or S;
is H and $R^2$ is —$CO_2R^6$ or $R^1$ is —$CO_2R^6$ and $R^2$ is H;
$R^3$ is H, halogen, or $C_1$-$C_6$ alkyl, wherein each hydrogen atom in $C_1$-$C_6$ alkyl, $C_2$-$C_6$ alkenyl, $C_2$-$C_6$ alkynyl or $C_3$-$C_6$ cycloalkyl is independently optionally substituted with halogen;
$R^4$ and $R^5$ are each independently selected from the group consisting of H, $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$—$C_6$ cycloalkyl), —$C_1$-$C_6$ alkyl-($C_6$-$C_{10}$ aryl), 3- to 7-membered heterocycloalkyl, $C_6$-$C_{10}$ aryl and 5- to 7-membered heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl), —$C_1$-$C_6$ alkyl-($C_6$-$C_{10}$ aryl) or $C_6$-$C_{10}$ aryl is independently optionally substituted with halogen, $C_1$-$C_6$ alkyl, $C_2$-$C_6$ alkenyl, $C_2$-$C_6$ alkynyl, $C_3$—$C_6$ cycloalkyl, 3- to 7-membered heterocycloalkyl, 5- to 7-membered heteroaryl, —$OR^8$, —CN, —$NO_2$, —$C(O)R^8$, —$CO_2R^8$, —$C(O)NR^8R^9$, —$OS(O)R^8$, —$OS(O)_2R^8$, —$SR^8$, —$S(O)R^8$, —$S(O)_2R^8$, —$S(O)NR^8R^9$, —$S(O)_2NR^8R^9$, —$OS(O)NR^8R^9$, —$OS(O)_2NR^8R^9$, and —$NR^8R^9$, provided that one of $R^4$ or $R^5$ is not H;

$R^6$ is H;

$R^8$, $R^9$, $R^{11}$ and $R^{12}$ are each independently selected from the group consisting of H, $C_1$-$C_6$ alkyl, $C_2$-$C_6$ alkenyl, $C_2$-$C_6$ alkynyl, $C_3$-$C_6$ cycloalkyl, —$C_1$-$C_6$ alkyl-($C_3$-$C_6$ cycloalkyl), —$C_1$-$C_6$ alkyl-($C_6$-$C_{10}$ aryl), 3- to 7-membered heterocycloalkyl and $C_6$-$C_{10}$ aryl; and $R^{10}$ is selected from the group consisting of halogen, $C_1$-$C_6$ alkyl, $C_2$-$C_6$ alkenyl, $C_2$-$C_6$ alkynyl, $C_3$_$C_6$ cycloalkyl, 3- to 7-membered heterocycloalkyl, 5- to 7-membered heteroaryl, —$OR^{11}$, —CN, —$NO_2$, —$C(O)R^{11}$, —$CO_2R^{11}$, —$C(O)NR^{11}R^{12}$, —$OS(O)R^{11}$, —$OS(O)_2R^{11}$, —$SR^{11}$, —$S(O)R^{11}$, —$S(O)_2R^{11}$, —$S(O)NR^{11}R^{12}$, —$S(O)_2NR^{11}R^{12}$, —$OS(O)NR^{11}R^{12}$, —$OS(O)_2NR^{11}R^{12}$, and —$NR^{11}R^{12}$;

===== is either a single bond or a pi-bond.

3. The method of claim 1, wherein the compound is of the formula Ia,

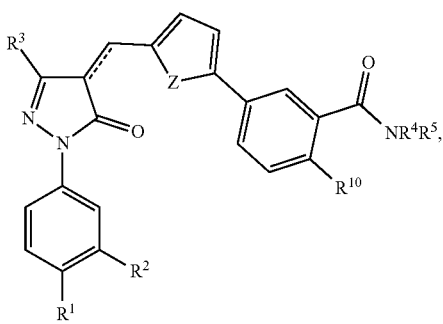

Ia or a pharmaceutically acceptable salt thereof.

4. The method of claim 3, wherein $R^{10}$ is chloro.

5. The method of claim 1, wherein the compound is of formula Ib

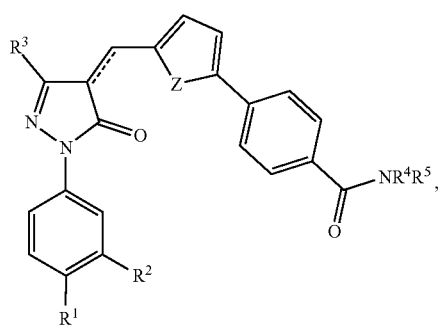

Ib or a pharmaceutically acceptable salt thereof.

6. The method of claim 2, wherein $R^4$ is $C_6$-$C_{10}$ aryl, wherein each hydrogen atom in $C_6$-$C_{10}$ aryl is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —$C(O)R^8$, —$CO_2R^8$, —$C(O)NR^8R^9$, —$OS(O)R^8$, —$OS(O)_2R^8$, —$SR^8$, —$S(O)R^8$, —$S(O)_2R^8$, —$S(O)NR^8R^9$, —$S(O)_2NR^8R^9$, —$OS(O)NR^8R^9$, —$OS(O)_2NR^8R^9$, or —$NR^8R^9$.

7. The method of claim 6, wherein $R^4$ is phenyl substituted with at least one halogen or —$OR^8$.

8. The method of claim 2, wherein $R^4$ is —$C_1$-$C_6$ alkyl-($C_3$-$C_6$ cycloalkyl).

9. The method of claim 2, wherein $R^4$ is —$C_1$-$C_6$ alkyl-($C_6$-$C_{10}$ aryl), and each hydrogen atom in $C_6$-$C_{10}$ aryl is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —$C(O)R^8$, —$CO_2R^8$, —$C(O)NR^8R^9$, —$OS(O)R^8$, —$OS(O)_2R^8$, —$SR^8$, —$S(O)R^8$, —$S(O)_2R^8$, —$S(O)NR^8R^9$, —$S(O)_2NR^8R^9$, —$OS(O)NR^8R^9$, —$OS(O)_2NR^8R^9$, or —$NR^8R^9$.

10. The method of claim 2, wherein $R^4$ is benzyl, wherein each hydrogen atom in benzyl is independently optionally substituted with halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, 5- to 7-membered heteroaryl, —$OR^8$, —CN, —$NO_2$, —$C(O)R^8$, —$CO_2R^8$, —$C(O)NR^8R^9$, —$OS(O)R^8$, —$OS(O)_2R^8$, —$SR^8$, —$S(O)R^8$, —$S(O)_2R^8$, —$S(O)NR^8R^9$, —$S(O)_2NR^8R^9$, —$OS(O)NR^8R^9$, —$OS(O)_2NR^8R^9$, or —$NR^8R^9$.

11. The method of claim 2, wherein $R^4$ selected from the group consisting of

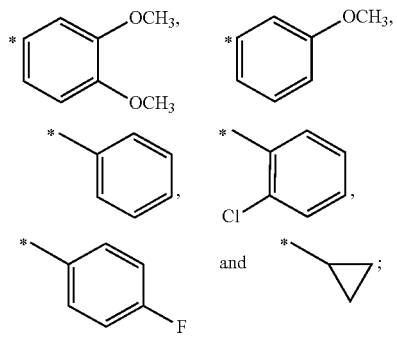

wherein * represent the point of attachment of $R^4$ to the amide nitrogen.

12. The method of claim 11, wherein $R^5$ is H.

13. The method of claim 1, wherein $R^3$ is $C_1$-$C_6$ alkyl.

14. The method of claim 13, wherein $R^3$ is methyl.

15. The method of claim 2, wherein $R^1$ is H and $R^2$ is —$CO_2R^6$, and wherein $R^6$ is H.

16. The method of claim 2, wherein $R^1$ is —$CO_2R^6$, and $R^2$ is H, and wherein $R^6$ is H.

17. The method of claim 1, wherein ===== is a pi-bond.

18. The method of claim 1, wherein the compound is of a formula selected from the group consisting of

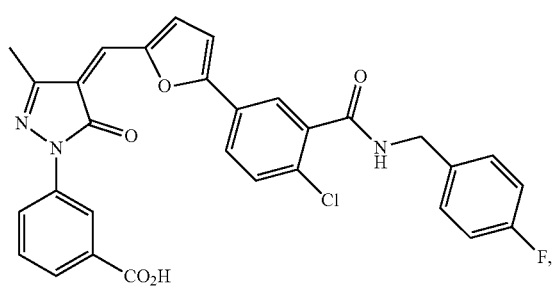

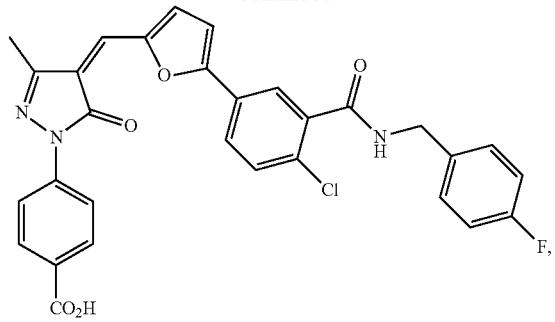

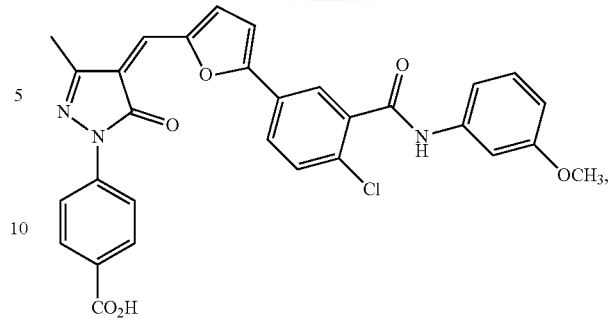

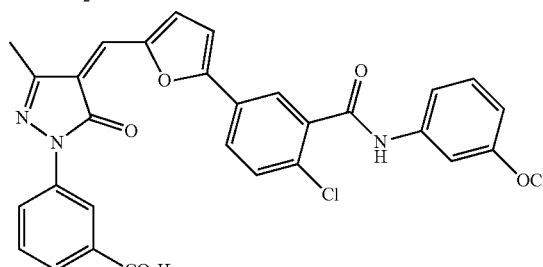

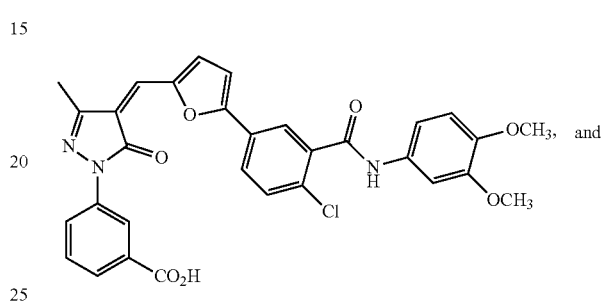

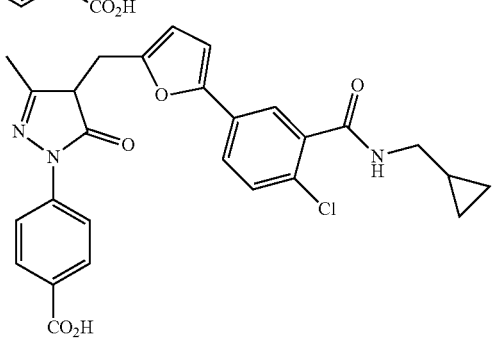

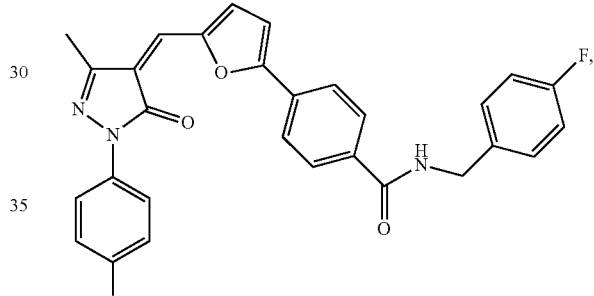

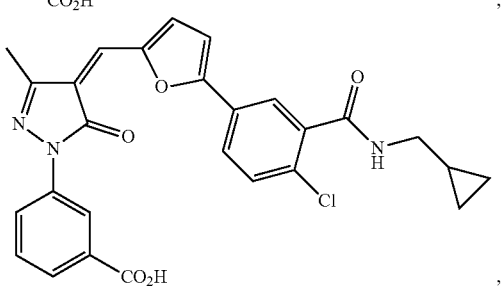

or a pharmaceutically acceptable salt thereof.

19. The method of claim 1, wherein the additional cancer therapy is a platinum drug.

20. The method of claim 19, wherein the platinum drug is selected from the group consisting of cisplatin, carboplatin, oxaliplatin, nedaplatin, triplatin tetranitrate, phenanthriplatin, picoplatin, and satraplatin.

21. The method of claim 1, wherein the patient was previously administered a cancer therapy.

22. The method of claim 21, wherein the additional cancer therapy is a platinum drug.

23. The method of claim 22, wherein the platinum drug is selected from the group consisting of cisplatin, carboplatin, oxaliplatin, nedaplatin, triplatin tetranitrate, phenanthriplatin, picoplatin, and satraplatin.

* * * * *

UNITED STATES PATENT AND TRADEMARK OFFICE
CERTIFICATE OF CORRECTION

| | |
|---|---|
| PATENT NO. | : 11,207,296 B2 |
| APPLICATION NO. | : 16/647746 |
| DATED | : December 28, 2021 |
| INVENTOR(S) | : John J. Turchi |

It is certified that error appears in the above-identified patent and that said Letters Patent is hereby corrected as shown below:

In the Specification

Column 1, The Statement of Governmental Rights, Lines 16-19 should read:
This invention was made with government support under CA180710, CA195926, TR000006, and CA247370 awarded by the National Institutes of Health. The government has certain rights in the invention.

In the Claims

Column 102, Claim 2, Line 46 should read:
$R^1$ is H and $R^2$ is -$CO_2R^6$ or $R^1$ is -$CO_2R^6$ and $R^2$ is H;

Signed and Sealed this
Twentieth Day of June, 2023

Katherine Kelly Vidal
*Director of the United States Patent and Trademark Office*